(12) United States Patent
Schroder et al.

(10) Patent No.: US 9,593,132 B2
(45) Date of Patent: Mar. 14, 2017

(54) METAL-ORGANIC FRAMEWORKS (MOF) FOR GAS CAPTURE

(71) Applicant: The University of Nottingham, Nottingham (GB)

(72) Inventors: Martin Schroder, Nottingham (GB); Sihai Yang, Nottingham (GB)

(73) Assignee: The University of Nottingham, Nottingham (GB)

(*) Notice: Subject to any disclaimer, the term of this patent is extended or adjusted under 35 U.S.C. 154(b) by 0 days.

(21) Appl. No.: 14/388,466

(22) PCT Filed: Mar. 27, 2013

(86) PCT No.: PCT/GB2013/050811
§ 371 (c)(1),
(2) Date: Sep. 26, 2014

(87) PCT Pub. No.: WO2013/144628
PCT Pub. Date: Oct. 3, 2013

(65) Prior Publication Data
US 2015/0047505 A1 Feb. 19, 2015

(30) Foreign Application Priority Data
Mar. 27, 2012 (GB) .................... 1205365.8

(51) Int. Cl.
*B01D 53/02* (2006.01)
*C07F 5/00* (2006.01)
(Continued)

(52) U.S. Cl.
CPC .............. *C07F 5/003* (2013.01); *B01D 53/02* (2013.01); *B01D 53/0407* (2013.01);
(Continued)

(58) Field of Classification Search
CPC ................ B01D 53/02; B01D 53/0407; B01D 2253/204; B01D 2257/302;
(Continued)

(56) References Cited

U.S. PATENT DOCUMENTS 7,556,673 B2 7/2009 Schubert et al.
7,799,120 B2 9/2010 Yaghi et al.
(Continued)

FOREIGN PATENT DOCUMENTS

WO WO-2010/148276 A2 12/2010

OTHER PUBLICATIONS

Finsy, V., et al., "of CO2/CH4 mixtures with the MIL-53 (Al) metal-organic framework," *Microporous and Mesoporous Materials*, 2009, vol. 120(3), pp. 221-227.
(Continued)

*Primary Examiner* — Frank Lawrence
(74) *Attorney, Agent, or Firm* — Alston & Bird LLP

(57) ABSTRACT

The present invention relates to a metal organic framework comprising of a metal ion (M) and an organic ligand wherein more than one hydroxy ligand are present about the metal ion. Also provided is a method for synthesizing the metal-organic frameworks and their application in areas including scrubbing exhaust gas streams of acidic gases, scrubbing natural gas of acidic gases by separation or sequestration and separating $C_2H_a$ or other VOC gases from other gas mixtures.

20 Claims, 73 Drawing Sheets

(51) Int. Cl.
*B01J 20/22* (2006.01)
*C07F 9/90* (2006.01)
*C07F 11/00* (2006.01)
*C07F 15/02* (2006.01)
*C07F 5/06* (2006.01)
*B01D 53/04* (2006.01)
*C07F 9/92* (2006.01)
*F17C 11/00* (2006.01)

(52) U.S. Cl.
CPC ............ *B01J 20/226* (2013.01); *C07F 5/069* (2013.01); *C07F 9/902* (2013.01); *C07F 9/92* (2013.01); *C07F 11/005* (2013.01); *C07F 15/025* (2013.01); *F17C 11/00* (2013.01); B01D 2253/204 (2013.01); B01D 2256/24 (2013.01); B01D 2257/302 (2013.01); B01D 2257/404 (2013.01); B01D 2257/504 (2013.01); B01D 2257/7022 (2013.01); Y02C 10/08 (2013.01); Y02P 20/152 (2015.11)

(58) Field of Classification Search
CPC ........ B01D 2257/404; B01D 2257/504; B01D 2257/7022; B01J 20/226; F17C 11/00; Y02C 10/08; C07F 11/005; C07F 5/003; C07F 5/069; C07F 9/902; C07F 9/92; C07F 15/025
USPC .............. 95/129, 139, 143; 96/154; 206/0.7; 556/1, 184, 61, 78, 147
See application file for complete search history.

(56) References Cited

U.S. PATENT DOCUMENTS

| | | | |
|---|---|---|---|
| 8,637,690 B2* | 1/2014 | Chaplais | ........................ 502/150 |
| 2010/0076220 A1 | 3/2010 | Schubert et al. | |
| 2012/0296103 A1* | 11/2012 | Savonnet | ................ C07F 5/069 552/4 |
| 2013/0296162 A1* | 11/2013 | Wright | ................... B01J 20/226 502/167 |

OTHER PUBLICATIONS

Mendt, M., et al., "Structural Phase Transitions and Thermal Hysteresis in the Metal-Organic Framework Compound MIL-53 As Studied by Electron Spin Resonance Spectroscopy," *J. Phys. Chem. C.*, 2010, vol. 114(45), pp. 19443-19451.

Yang, S., et al., "Selectivity and direct visualization of carbon dioxide and sulfur dioxide in a decorated porous host," *Nature Chemistry*, 2012, vol. 4, pp. 887-894.

Sumida, K., et al., "Carbon Dioxide Capture in Metal—Organic Frameworks," *Chemical Reviews*, 2012, pp. 724-781, vol. 112.

Yazaydin, A., et al., "Screening of Metal—Organic Frameworks for Carbon Dioxide Capture from Flue Gas Using a Combined Experimental and Modeling Approach," *J. Am. Chem. Soc.*, 2009, pp. 18198-18199, vol. 131.

* cited by examiner (a)

(b)

(c)

METAL-ORGANIC FRAMEWORKS (MOF) FOR GAS CAPTURE

This invention relates to coordination polymers, and in particular to metal organic frameworks, and the use of such metal organic frameworks for gas capture. The invention also relates to a method of making such metal organic frameworks

BACKGROUND

It is widely accepted that it is imperative that emissions of carbon dioxide ($CO_2$) and other acidic gases such as sulphur dioxide ($SO_2$) and nitrogen dioxide ($NO_2$) created by human activity is reduced in order to limit the negative effects of global climate change. One particular challenge is the reduction of $CO_2$ emissions from flue gases produced by large industrial plant and coal-fired power stations. Current state-of-the-art technology uses aqueous solutions of organic amines for post-combustion $CO_2$ capture, a so called "amine-scrubbing mechanism". These amine functionalised capture systems dominate this area, due to potential formation of carbamates via $H2N(\delta-) \ldots C(\delta+)O2$ electrostatic interactions, thereby trapping $CO_2$ covalently. However, there are considerable costs associated with this process due to the substantial energy input required for the regeneration of the amine solutions, this is in addition to their highly corrosive and toxic nature. Thus there is a negative environmental penalty associated with the use of amines which significantly limits their long-term applications. There are, therefore, powerful drivers to develop efficient strategies to remove $CO_2$ using alternative materials that simultaneously have high adsorption capacity, high $CO_2$ selectivity and high rates of regeneration at an economically viable cost. Traditional microporous solid-state materials such as zeolites, porous membranes and activated carbon can effectively adsorb and remove $CO_2$. However, the low separation efficiency and poor selectivity of these materials significantly limits their real-world applicability. Therefore there is a need to develop new materials with high $CO_2$ storage capacity and selectivity that can be produced at an economically and environmentally viable cost.

Metal organic frameworks (MOF), a relatively new class of porous materials, are built up of metal cation nodes bridged by organic ligand linkers and they have huge potential to deliver significant breakthroughs in carbon capture. The advantages of MOFs over existing technologies include: (i) they can store greater amounts of $CO_2$ than other classes of porous materials, including commercial materials such as zeolite 13X and activated carbon; (ii) their surface areas and pore volume can be adjusted via appropriate crystal engineering and topological connections in order to maximise the $CO_2$ adsorption capacity; (iii) the pore surface and environment can be fine controlled and tuned via variation of organic and inorganic components that constitute the framework in order to enhance $CO_2$ capacity and selectivity; (iv) the adsorbed $CO_2$ molecules can be readily released via reduction of the pressure, i.e. the capture system can be regenerated without additional heating input; (v) the extended crystalline structure of MOF materials gives a unique opportunity to determine and study the mechanisms of carbon capture and storage (CCS) using advanced diffraction techniques.

US patent application US2007/0068389 describes the use of a number of Copper and Zinc based MOF materials to store carbon dioxide at room temperature. These materials show high uptakes of $CO_2$ and have been shown to perform better than zeolites and activated carbons as carbon dioxide storage media inside gas canisters. However, there is a need for metal-organic frameworks with:
 a) higher CO2 adsorption capacity;
 b) selective adsorption of acidic gases & VOCs;
 c) improved framework stability;
 d) and improved ease of manufacture.

SUMMARY

In a first aspect the present invention provides a solid crystalline metal-organic framework comprising of a metal ion, preferably one of Al(III), Cr(III), Sb(III), In(III), Ga(III), and Fe(III) and an organic ligand. Wherein said organic ligand is a polycarboxylate. Typically, the organic ligand is a tetracarboxylate; preferably a biphenyl tetracarboxylate. In the embodiments of the invention the metal ion (M) is octahedrally coordinated as the moiety $MO_4(OH)_2$ via six oxygen atoms. Four of the oxygen atoms are from the carboxylate groups and two of the oxygen atoms are from the hydroxyl groups.

The resulting crystalline MOF structure has channels between the repeating units of the metal-hydroxyl[tetracarboxylate] complexes. Preferably, the metal organic framework incorporates a channel decorated by metal hydroxyl groups and phenyl rings that are available to form electrostatic interactions between $XO_2$ (X=C, S, N) gas molecules or small hydrocarbon molecules, e.g. VOCs. The hydrocarbon molecule may be one or more of $C_2H_2$, $C_2H_4$, $C_2H_6$ or one of the isomers of xylene. Gases, such as methane, nitrogen, hydrogen, carbon monoxide, argon and oxygen do not interact with the framework and thus are not adsorbed by the material.

The weak interactions between the captured gas and the MOF material lead to low isoteric heats of absorption, thereby reducing the amount of energy required to drive off the captured gas and regenerate the vacated MOF material. This weak interaction is advantageous when compared to the formation of chemical bonds between amine substrates and gas molecules in amine-containing solutions/solids. Typically, in conventional amine functionalised MOFs, the isoteric heats of adsorption are 40-90 kJ mol$^{-1}$ for physisorption and 85-105 kJ mol$^{-1}$ for chemisorption. These high values for chemisorption lead to a substantial energy penalty to release adsorbed $CO_2$ from the metal-organic structure. Therefore a large energy penalty is avoided in using the MOF materials of the type described herein. Thus there may be applications these MOFs in industrial scale capture and separation of acidic gases due to the potentially significant energy savings available.

In such systems the $CO_2$ or other gases are released from the MOF during the MOF regeneration process and extracted as a stream of gas. The extracted gas can then be compressed for storage or transport. Post Combustion Capture (PCC) of acidic gases from flue gas and sequestration/separation of these gases is relevant in the following industrial sectors: power generation, iron and steel production, ammonia production, cement production, natural gas sweetening, syngas gas purification.

The MOF materials have also shown adsorption of short chain hydrocarbons gases such as ethylene and acetylene. Notably a preference for acetylene adsorption over ethylene and ethane has been observed and this selectivity is an important property which may make these MOFs suitable candidates for gas separation. In some embodiments the hydrocarbon may also be a substituted hydrocarbon such as a halogenated hydrocarbon. Furthermore, embodiments of the invention may also be applied to the capture of other small molecules such as "C3" molecules (i.e. molecules having three carbon atoms). Embodiments of the invention may also be used to capture other Volatile Organic Compounds (VOCs).

Anaesthetic systems comprise of a rebreather system in which $CO_2$ is scrubbed from the anaesthetic gas during the cycling of the gas. Currently soda lime is used for this process. According to the present invention the MOF may be used for scrubbing the $CO_2$ from the recycled gas. The potential for MOFs in this area is the reduction of medical/chemical waste as soda lime has a finite life and, once depleted, it is disposed of as contaminated waste. Moreover, there is known decomposition of the anaesthetic gases due to reaction with the caustic soda lime which may lead to patient inhalation of potentially harmful by-products. Additives are used to prevent this. NOTT-300 may provide $CO_2$ scrubbing where no reaction between the anaesthetic gas and the MOF material is observed.

The present invention may also find use in: diving rebreathers (i.e. SCUBA); personal protective equipment (PPE), gas masks etc. (acidic gas scrubbing); military applications (PPE, gas scrubbing air in closed environments e.g. bunkers, submarines etc.), syn-gas purification; driving the water gas shift to completion for more efficient production of hydrogen from CO and water; mixed matrix materials i.e. the impregnation of MOFs into membranes for gas separation.

Typically, the organic ligand is a tetracarboxylic acid; preferably, the organic ligand is a phenyl tetracarboxylic acid; preferably, the organic ligand is a phenyl tetracarboxylic acid selected from the group having the general formula (I):

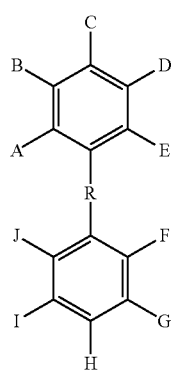

wherein R is one of:

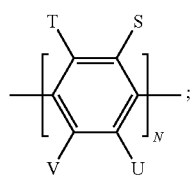

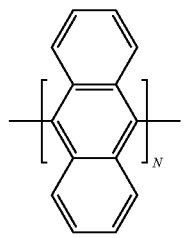

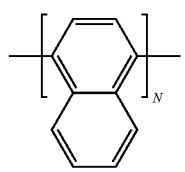

wherein A, B, C, D, E, F, G, H, I, and J are selected from the group consisting of H, F, Cl, Br, I, CH3, CH2CH3, CH(CH3)2, C(CH3)3, NH2, NHR', NR'R", OH, OR', CO2H, CO2R', CF3, NHCOR', NHCONHR', NHSO2R', SO3H; and wherein S, T, U and V are selected from the group consisting of H, F, Cl, Br, I, CH3, CH2CH3, CH(CH3)2, C(CH3)3, NH2, NHR', NR'R", OH, OR', CO2H, CO2R', CF3, NHCOR', NHCONHR', NHSO2R', SO3H and

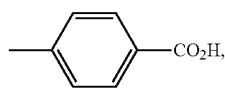

where R' and R" are selected from the group consisting $C_1$ to $C_5$ alkyl.

Preferably, two of A,B,C,D, or E are —COOH and two of F, G, H, I or J are —COOH. Alternatively, when only one of A, B, C, D, or E are —COOH and only one of F, G, H, I or J are —COOH, then two of T, S, U and V are —COOH or

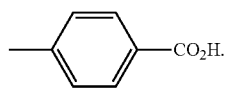

In a preferred embodiment the organic ligand is selected from the group consisting of:

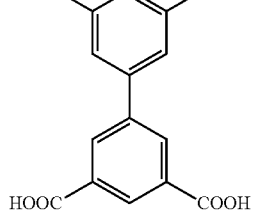

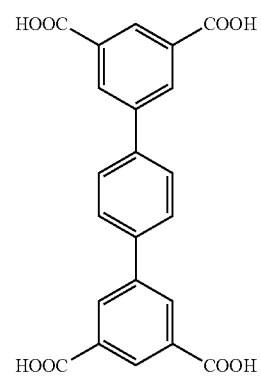

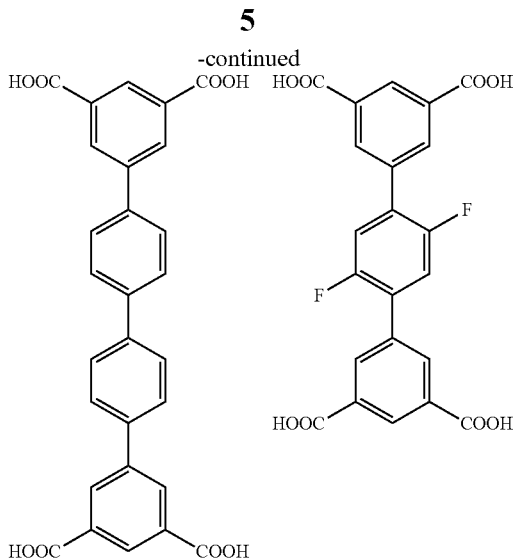
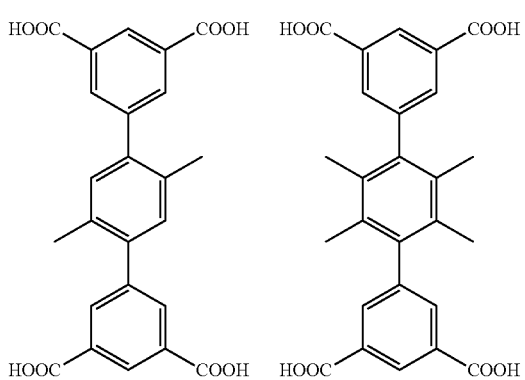
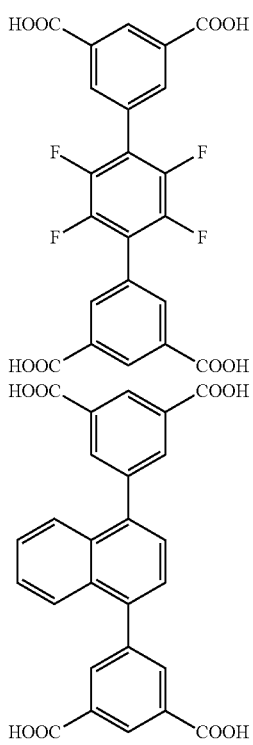
and

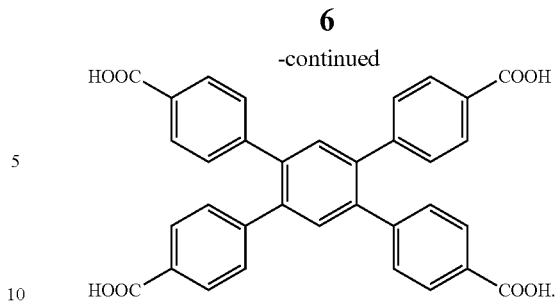

In an embodiment of the invention the MOF is one of: $M_2(OH)_2(C_{16}O_8H_6)$; where M=Al, In, Sb, Ga, Cr being a biphenyl tetracarboxylate ligand, for example biphenyl-3,3',5,5' tetracarboxylate.

In one particular example the MOF contains more than a single type metal (III) ion preferably the metal ion being selected from Al(III), Cr(III), Sb(III), In(III), Ga(III), and Fe(III) For example the complex may comprise of both gallium and iron and have the formula $(Ga_{2-x}Fe_x)(OH)_2(C_{16}O_8H_6)$ with x being greater than zero.

In a second aspect, the present invention provides a method for producing a metal-organic framework comprising the steps of:
 a. providing one or more metal salts;
 b. providing an organic ligand;
 c. mixing the metal salts and the organic ligand; and
 d. reacting the metal salts with organic ligand to form a metal-organic framework,
wherein the metal salt is selected from Al(III), Cr(III), Sb(III), In(III), Ga(III), and Fe(III) salts and wherein the organic ligand is a tetracarboxylic acid tetracarboxylic acid molecule may have the structure (I) identified hereinabove.

The synthesis of the aluminum MOF is particularly advantageous as it requires water as the only solvent and avoids the use of toxic solvents such as N,N-dimethylformamide that are commonly used to synthesise MOF materials. Additionally aluminium is a relatively cheap metal in comparison to some other metal (III) ions.

For the MOF complex $Al_2(OH)_2(C_{16}O_8H_6)$, the method may comprise reacting biphenyl-3,3',5,5'-tetracarboxylic acid with $Al(NO_3)_3.9H_2O$; for the MOF complex $In_2(OH)_2(C_{16}O_8H_6)$ the method may comprises reacting biphenyl-3,3',5,5'-tetracarboxylic acid with $In(NO_3)_3.5H_2O$; for the MOF complex $Cr_2(OH)_2(C_{16}O_8H_6)$ and the method comprises reacting biphenyl-3,3',5,5'-tetracarboxylic acid with $Cr(NO_3)_3.9H_2O$.

In one particular example the MOF contains more than one single type metal (III) ion preferably with the metal ion(s) being selected from Al(III), Cr(III), Sb(III), In(III), Ga(III), and Fe(III). For example the complex may comprise of both gallium and iron and have the formula $(Ga_{2-x}Fe_x)(OH)_2(C_{16}O_8H_6)$ with x being greater than zero. In one example the MOF complex is $(Ga_{2-x}Fe_x)(OH)_2(C_{16}O_8H_6)$, x>0, and the method comprises reacting a stoichiometric mixture of gallium nitrate, iron nitrate, hydrochloric acid and biphenyl-3,3',5,5'-tetracarboxylic acid under solvothermal conditions.

In one embodiment the invention provides use of the MOF to capture two different gases in one pore of the MOF.

An aspect of the invention provides a gas storage/separation system comprising: an inlet for receiving gas containing $XO_2$ (X=C, S, N), and/or a $C_2H_n$ (n=2,4,6); a container for receiving the gas from the inlet; and a storage/separation material comprising of the MOF framework, in supported or unsupported forms, according to aspects and embodiments of the invention set out hereinabove.

DESCRIPTION OF THE FIGURES

The above-mentioned and other features and objects of this invention, and the manner of obtaining them, will become more apparent and the invention itself will be better understood by reference to the following description of embodiments of the invention taken in conjunction with the accompanying drawings, wherein:

FIG. 1($a$) illustrates the bonds formed between carbon dioxide molecules and an amine group as would be present in known amine functionalised systems. In such systems the first $CO_2$ molecule interacts with the $NH_2$ group through a side-on mode and the second $CO_2$ molecules interacts with the first $CO_2$ molecule through an end-on mode. Such interactions result in high isosteric heats of adsorption particularly when there is direct bond formation between the N-centre of the amine group and the electro-positive C-carbon centre of $CO_2$ (i.e. chemisorption);

FIG. 1($b$) illustrates the hydrogen bonds present between a hydroxyl functionalised material and $CO_2$ molecules;

FIG. 1($c$) illustrates the hydrogen bonds present between a hydroxyl functionalised material and $SO_2$ molecules;

FIG. 1($d$) shows the anticipated interactions believed to be the rationale behind the high $NO_2$ adsorption capacities observed;

FIG. 2($a$) illustrates the coordination environment for ligand $L^{4-}$ and M(III) centre. FIG. 2($b$) illustrates a corner-sharing extended octahedral chain of $[MO_4(OH)_2]_\infty$. The $\mu_2$-(OH) groups are highlighted as a space-filling model, and linked to each other in a cis-configuration. FIG. 2($c$) illustrates the 3D framework structure with channel formed along the c-axis. The free water molecules in the channel are omitted for clarity. FIG. 2($d$) is a schematic view of the square-shaped channel. The $\mu_2$-(OH) groups protrude into the centre of the channel from four directions. [$MO_4(OH)_2$] groups are illustrated as octahedral. A $\mu_2$-OH group is an —OH group that is coordinated to two metal centres, i.e. it is a bridging —OH group;

FIG. 3 ($b$) is a graph illustrating the variation of isosteric enthalpy ($Q_{st}$) and entropy ($\Delta S$) of $CO_2$ adsorption;

FIG. 4 ($a$) shows in situ inelastic neutron scattering (INS) spectra and simulated $CO_2$ positions in the pore channel. This diagram shows a comparison of the experimental (top) and DFT simulated (bottom) INS spectra for bare and $CO_2$-loaded NOTT-300 (Al).

FIG. 4 ($b$) is a difference plot for experimental INS spectra of bare and $CO_2$-loaded NOTT-300 (Al). Two distinct energy transfer peaks are labelled as I and II;

FIG. 4 ($c$) is a view of the structure of NOTT-300 (Al).3.2$CO_2$ obtained from PXRD analysis. The adsorbed $CO_2$ molecules in the pore channel are highlighted by the use of ball-and-stick mode. The carbon atom of second site of $CO_2$ is shown. The dipole interaction between $CO_2$ (I, II) molecules are shown [O═C═O . . . $CO_2$=3.920 Å].

FIG. 4 ($d$) is a detailed view of the role of the —OH and —CH groups in binding $CO_2$ molecules in a "pocket-like" cavity. The model was obtained from DFT simulation. The modest hydrogen bond between O($\delta$−) of $CO_2$ and H($\delta$+) from the Al—OH moiety is shown, [O . . . H=2.335 Å]. The weak cooperative hydrogen bond interactions between O($\delta$−) of $CO_2$ and H($\delta$+) from —CH is shown, [O . . . H=3.029, 3.190 Å, each occurring twice]. Each O($\delta$−) centre therefore interacts with five different H($\delta$+) centres.

FIG. 5 ($a$) is a comparison of the powder diffraction patterns for original, evacuated, $SO_2$-loaded, and final desolvated samples at 273 K.

FIG. 5 ($b$) illustrates the crystal structure of NOTT-300 (Al).4.0$SO_2$ obtained from Rietveld refinement of data on $SO_2$-loaded material at 1.0 bar. The adsorbed $SO_2$ molecules in the pore channel are highlighted by the use of ball-and-stick mode. The sulphur atom of second site of $SO_2$ is labelled with an asterisk.

FIG. 5 ($c$) provides a detailed view of the role of the —OH and —CH groups in binding $SO_2$ molecules into a distorted "pocket-like" cavity. The moderate hydrogen bond between O($\delta$−) of $SO_2$(I) and H($\delta$+) from —OH is shown as the a vertical dashed line, [O . . . H=2.376(13) Å]. The weak cooperative hydrogen interaction between O($\delta$−) of $SO_2$ and H($\delta$+) from —CH is shown, [O . . . H=2.806(14), 2.841(17), 3.111(16), 3.725(18) Å]. Therefore, each O($\delta$−) centre is interacting with five different H($\delta$+) centres simultaneously. The bond distance between S($\delta$+) of $SO_2$(I) and O($\delta$−) of $SO_2$(II) is 3.34(7) Å.

FIG. 6 ($a$) provides a comparison of the experimental (top) and DFT simulated (bottom) INS spectra for bare and $SO_2$-loaded NOTT-300;

FIG. 6 ($b$) is a difference plot for experimental INS spectra of bare and $SO_2$-loaded NOTT-300. Two distinct energy transfer peaks are labelled as I and II;

FIG. 6 ($c$) is a detailed view of the role of the —OH and —CH groups in binding $SO_2$ molecules in a "pocket-like" cavity. Model was obtained from DFT simulation. The adsorbed $SO_2$ molecules in the pore channel are highlighted by the use of ball-and-stick mode. The modest hydrogen bond between O($\delta$−) of $SO_2$ and H($\delta$+) from the Al—OH moiety is shown as the vertical dashed line, [O . . . H=2.338 Å]. The weak cooperative hydrogen bond interactions between O($\delta$−) of $CO_2$ and H($\delta$+) from —CH is shown, [O . . . H=2.965-3.238 Å]. Each O($\delta$−) centre therefore interacts with five different H($\delta$+) centres;

FIG. 10(a) is a plot of the experimental INS spectra for bare and $C_2H_2$-loaded NOTT-300. FIG. 10(b) is a difference plot for the experimental INS spectra of bare and $C_2H_2$-loaded NOTT-300. FIG. 10(c) is a plot of the experimental INS spectra for bare and $C_2H_4$-loaded NOTT-300. FIG. 10(d) is a difference plot for the experimental INS spectra of bare and $C_2H_4$-loaded NOTT-300.

FIG. 11(a) is a plot of the experimental INS spectra for solid $C_2H_2$. FIG. 11(b) is a plot for the experimental INS spectra of solid $C_2H_2$, showing backward scattering and forward scattering results.

FIG. 13(a) is a view from above. FIG. 13(b) is a side view;

FIG. 14(a) is a view from above. FIG. 14(b) is a side view;

FIG. 15(a) is a view from above. FIG. 15(b) is a side view;

FIG. 21(a) is a broad 2Th degree spectrum whereas FIG. 21(b) is a scaled up spectrum and FIG. 21 (c) is an even further scaled up spectrum.

LIST OF EXAMPLES

For the purposes of this description the term "NOTT-300" is used to denote complexes M$_2$(OH)$_2$(C$_{16}$O$_8$H$_6$) (M=Al, Cr, Sb, In, Ga, and Fe) whereas the term "NOTT-300-solvate" is used to denote the solvated form of the complex. The organic ligand C$_{16}$O$_8$H$_6$ takes the form of biphenyl-3, 3',5',5' tetracarboxylate. Such structures are discussed in detail herein-below.

Example 1

Synthesis of NOTT-300 (Al)

Biphenyl-3,3',5,5'-tetracarboxylic acid (0.06 g, 0.182 mmol), Al(NO$_3$)$_3$·9H$_2$O (0.34 g, 0.906 mmol), and piperazine (0.10 g, 1.26 mmol) were mixed and dispersed in a water (10.0 ml) and HNO$_3$ (2.8M, 2.0 ml) was then added to the resulting white slurry. The slurry was transferred into a 23 ml autoclave which was sealed and heated to 210° C. for 3 days. After cooling over 12 h to room temperature, the resulting white microcrystalline product was separated by filtration, washed with water and dried in air. Yield: 0.095 g (75%). Elemental analysis (% calc/found): Al$_2$O$_{16}$C$_{16}$H$_{20}$ (C, 36.8/36.3; H, 3.8/4.0; N, 0.0/0.0). Selected IR: ν/cm$^{-1}$: 3574 (m), 3425 (m), 2926 (w), 1623 (vs), 1570 (vs), 1475 (s), 1442 (s), 1346 (m), 1324 (m), 1265 (m), 1108 (m), 1003 (m), 914 (w), 807 (w), 742 (m), 702 (s), 668 (m).

Compared to traditional methods for the production of MOF materials, the synthetic conditions developed here for NOTT-300-(Al) can be viewed as constituting a green synthesis, not only because no organic solvent (e.g., DMF) is involved, but also because the ligand can be prepared from a simple oxidation reaction without using the toxic Pd(0) catalysts typically applied in Suzuki-coupling reactions to synthesise such polycarboxylate ligands.[18,19] Thus, this synthesis offers potential for inexpensive, feasible and environmentally-friendly scale-up.

PXRD Studies of NOTT-300 (Al)

Figure 1:
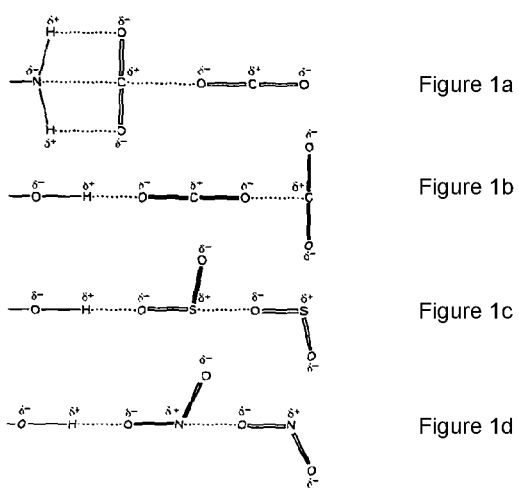
FIGS. 1($a$)-1($d$) show a schematic view comparing gas binding interactions in amine-functionalised materials and in hydroxyl-functionalised materials.
Figure 2A:
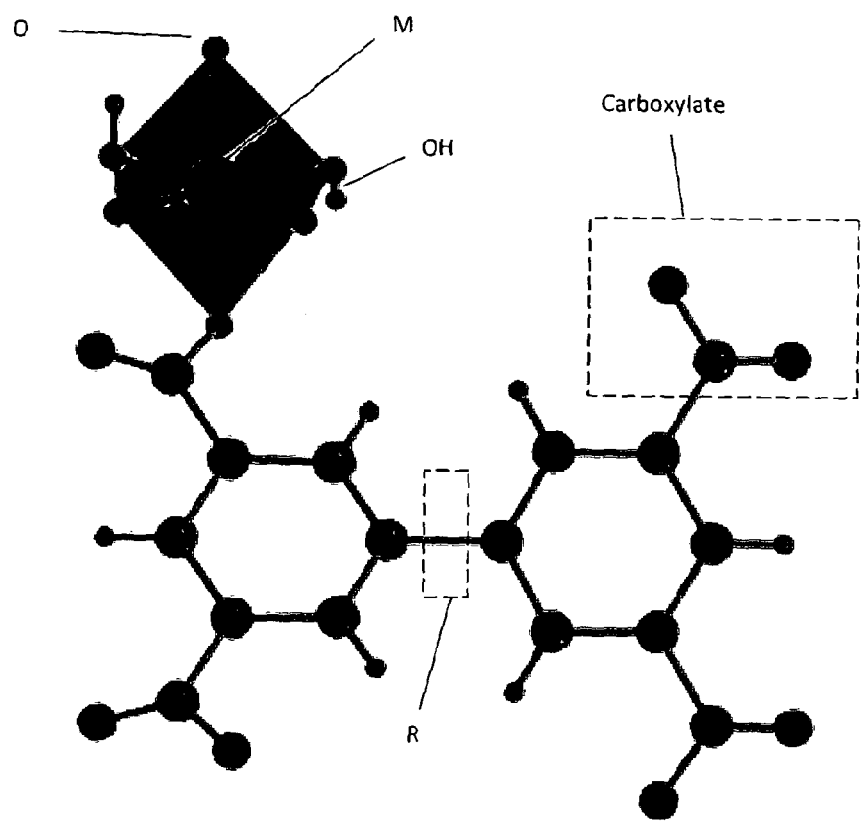
FIG. 2 provides views of the structure for NOTT-solvate. The structure was solved from high resolution PXRD data by ab initio methods for NOTT Al-solvate and has been found to be correct for equivalent compounds using other metal (III) ions.
Figure 2B:
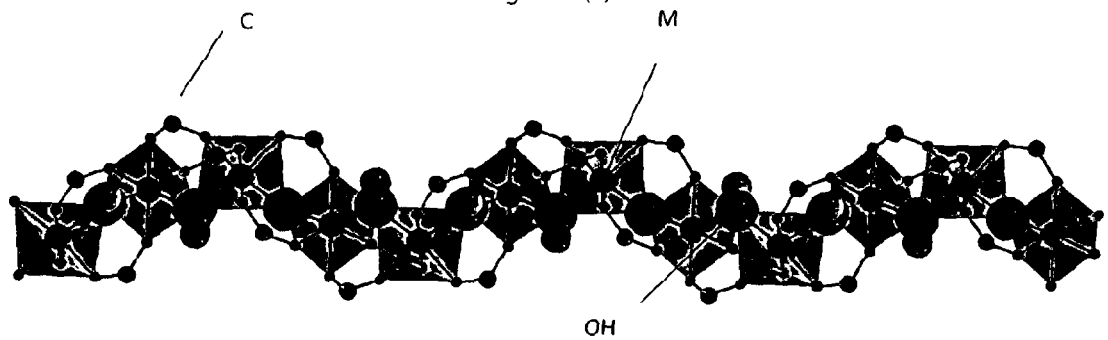
Figure 2C:
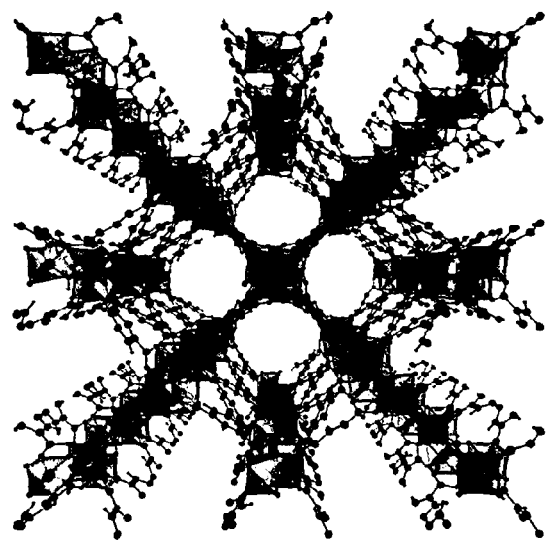
Figure 2D:
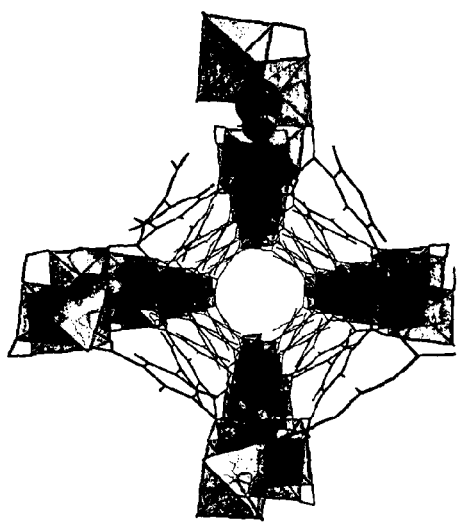
Figure 41:
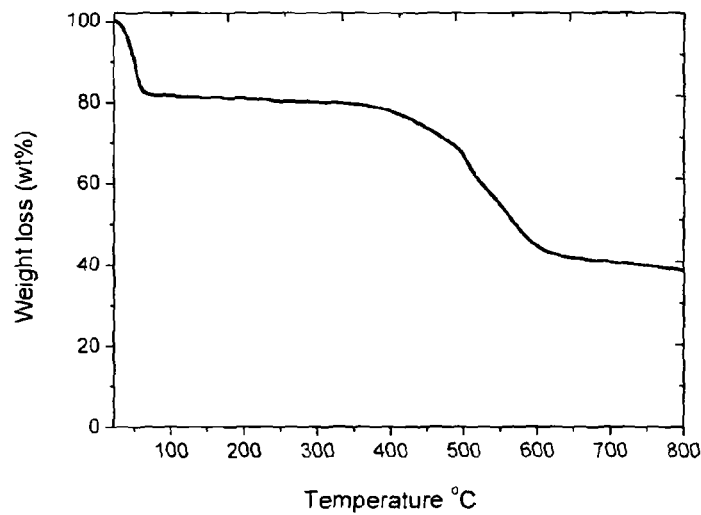
FIG. 41 is a Thermo Gravimetric Analysis (TGA) plot shows that the as-synthesised sample NOTT-300 (Al)-solvate loses solvent rapidly between 30 and 100° C., with a plateau observed from 100-200° C. indicating no further weight loss to give NOTT-300 (Al). The weight loss of 20.0% from NOTT-300 (Al)-solvate between 20 and 200° C. corresponds to a loss of three water molecules per aluminium (calc. 20.6 wt. %). Above 400° C. NOTT-300 (Al) starts to decompose rapidly.
Figure 42:
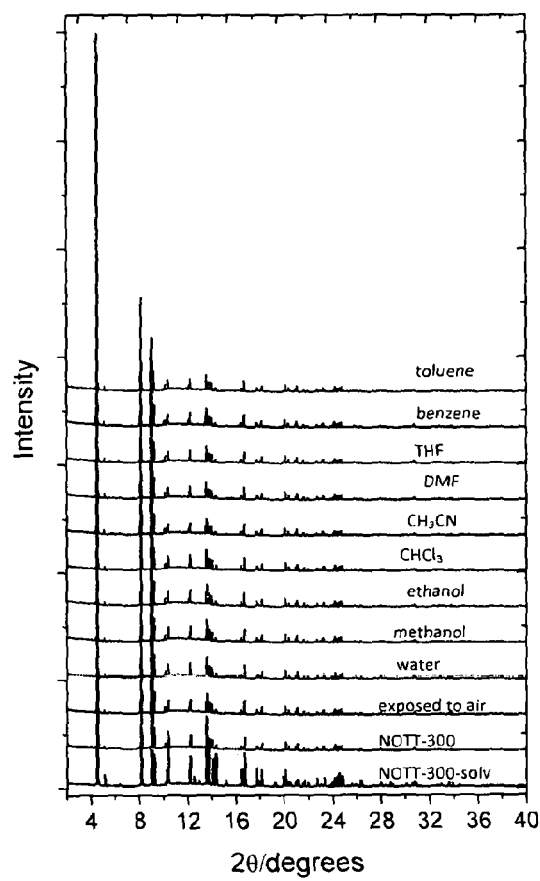
FIG. 42 illustrates PXRD spectra for NOTT-300(Al) under different chemical environments [$\lambda$=0.826134(2) Å]
Figure 44:
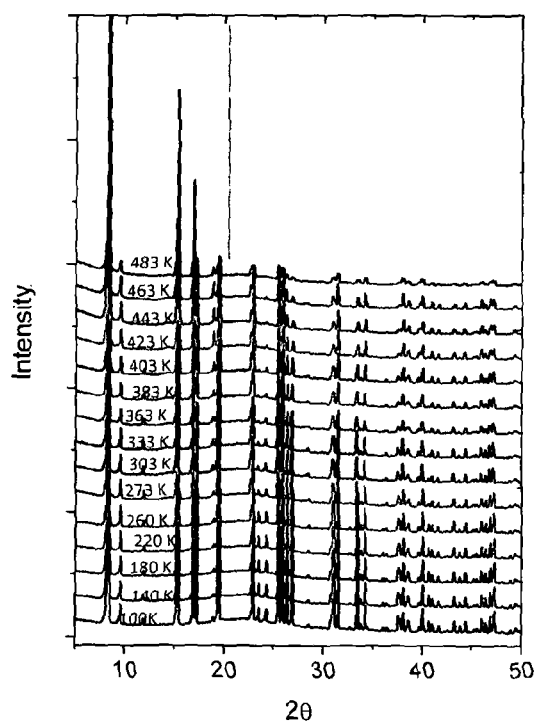
FIG. 44 illustrates variable temperature PXRD spectra for NOTT-300(Al)-solvate ($\lambda$=1.54056 Å)

The structure of NOTT-300 (Al)-solvate was solved from high resolution synchrotron PXRD data by ab initio methods in the chiral tetragonal space group I4$_1$22. NOTT-300 (Al)-solvate exhibits an open structure comprising chains of [AlO$_4$(OH)$_2$] moieties bridged by tetracarboxylate ligands L$^{4-}$. The Al(III) ion in NOTT-300 (Al)-solvate is bound to six O-donors, four from carboxylates [Al—O=1.935(1) and 1.929(2) Å] and two from bridging hydroxyl groups μ$_2$-OH [Al—O=1.930(1) Å]. Bond valence sum calculations give a valence of approximately 0.87 for this bridging oxygen atom, confirming its protonation to form a dangling μ$_2$-OH group. This overall connectivity affords a porous 3D framework structure with 1D channels (FIG. 2) formed by corner-sharing [AlO$_4$(OH)$_2$] octahedra linked via two mutually cis-μ$_2$-OH groups. Thus, the observed cis-configuration of μ$_2$-OH groups is responsible for the observed chirality and rigidity of the framework in NOTT-300 (Al). The rigidity of the framework structure of NOTT-300 (Al) has been confirmed by in situ variable temperature (100-483 K) PXRD data (FIG. 44). Another important consequence of the cis-configuration is the formation of square-shaped channels with hydroxyl groups protruding into them, endowing the pore environment with free hydroxyl groups over four different directions (FIG. 2d). The approximate diameter of the channel window, taking into account the van der Waals radii of the surface atoms, is ~6.5×6.5 Å, and these channels are filled by crystallographically-disordered water molecules which are not bound to Al(III). The total free solvent (water) volume in NOTT-300 (Al)-solvate was estimated by PLATON/SOLV* to be 42% (*Spek, A. L. Structure validation in chemical crystallography. *Acta Crystallogr., Sect. D* 65, 148-155 (2009)). The water molecules can be readily removed by heating, giving the desolvated and activated material NOTT-300 (Al), the PXRD of which confirms retention of the original porous structure. Thermogravimetric analysis (TGA) confirms NOTT-300 (Al) to have high thermal stability with a decomposition temperature at 400° C. (FIG. 41). NOTT-300 (Al) also shows good chemical stability towards air, moisture and common organic solvents, and can be re-hydrated with retention of the framework structure (FIG. 42). Significantly, the framework porosity and surface area of NOTT-300 (Al) is retained upon multiple hydration-dehydration cycles (FIG. 53), thereby confirming the stability of this material to water.

Gas Adsorption Properties of of NOTT-300 (Al)

Al-NOTT-300 (Al) exhibits highly selective uptake for CO$_2$ and SO$_2$ compared with CH$_4$, CO, N$_2$, H$_2$, O$_2$, and Ar. The CO$_2$ selectivities, calculated from the ratio of initial slopes of the isotherm are 100, 86, 180, >10$^5$, 70, and 137 for CH$_4$, CO, N$_2$, H$_2$, O$_2$, and Ar, respectively. The SO$_2$ selectivities, calculated from the ratio of the initial slopes of the isotherms are 3620, 3105, 6522, >10$^5$, 2518, and 4974 for CH$_4$, CO, N$_2$, H$_2$, O$_2$, and Ar, respectively. The thermodynamic parameters Q$_{st}$ and ΔS were calculated using the van't Hoff isochore on CO$_2$ adsorption isotherms measured at 273-303 K. The Q$_{st}$ values lie in the range 27.5-28 kJ mol$^{-1}$ for CO$_2$ uptakes of 1-2 mmol g$^{-1}$ and increase continuously thereafter to ~30 kJ mol$^{-1}$ at 4.5 mmol g$^{-1}$. The error in Q$_{st}$ is estimated as 0.05-0.5 kJ mol$^{-1}$ as shown by the error bars. Overall, ΔS decreases continuously with increasing surface coverage over the whole loading range. The error in ΔS is estimated as 0.2-1.6 J Kmol$^{-1}$ as shown by the error bars.

Figure 3A:
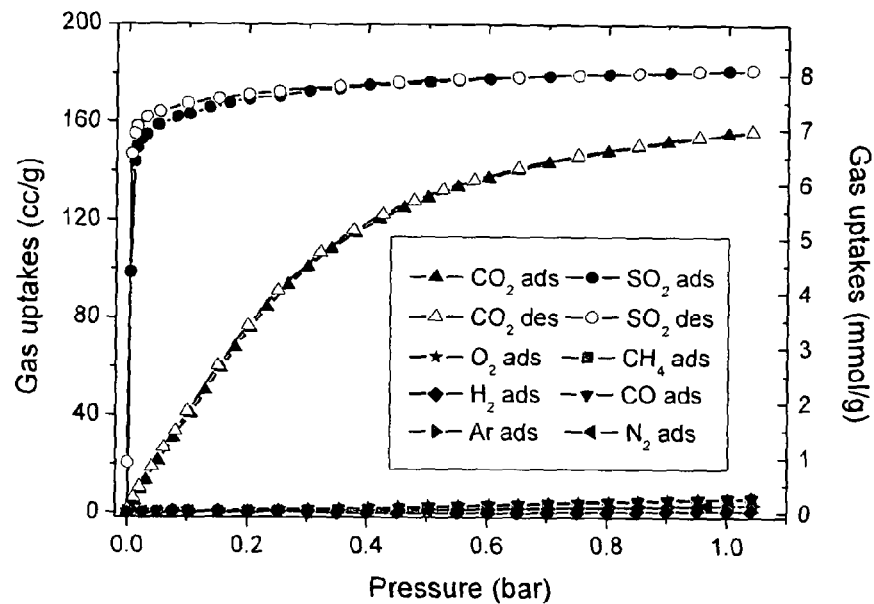
FIG. 3 ($a$) is a graph comparison of the gas adsorption isotherms for NOTT-300 (Al) at 273 K and 1.0 bar for a selection of gases.
Figure 46:
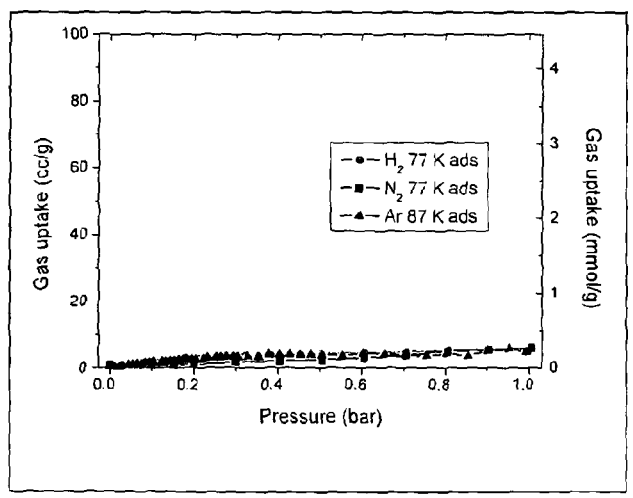
FIG. 46 illustrates H$_2$, N$_2$ and Ar sorption isotherms at 77 or 87 K for NOTT-300 (Al). No significant uptake was observed for these adsorption isotherms.
Figure 47A:
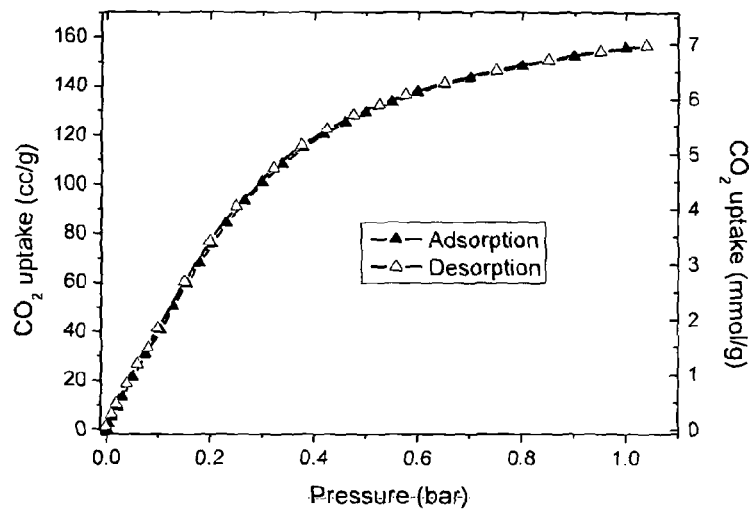
FIGS. 47(a)-47(d) illustrate CO$_2$ adsorption and desorption isotherms for NOTT-300 (Al) at (FIG. 47a) 273 K, (FIG. 47b) 283 K, (FIG. 47c) 293 K and (FIG. 47d) 303 K.
Figure 47B:
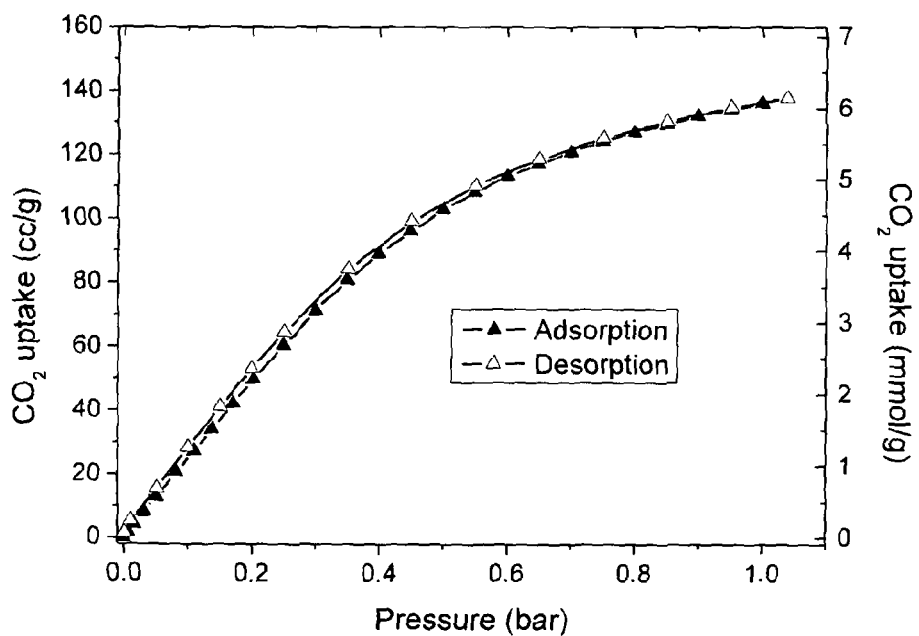
Figure 47C:
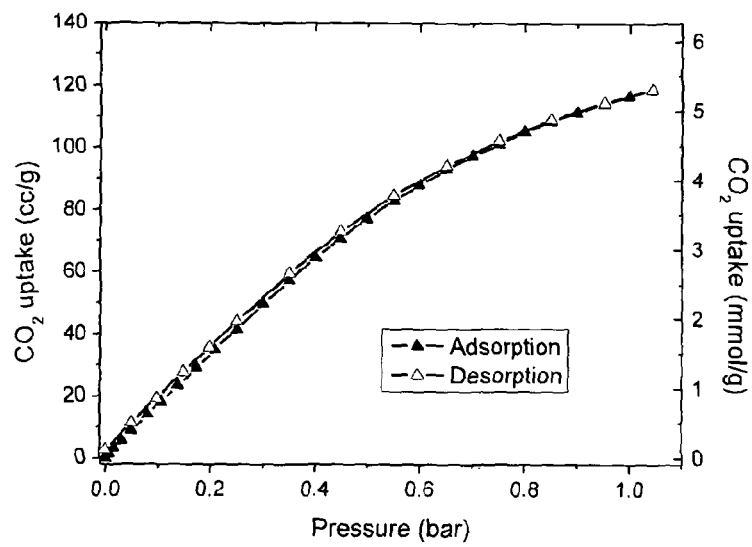
Figure 47D:
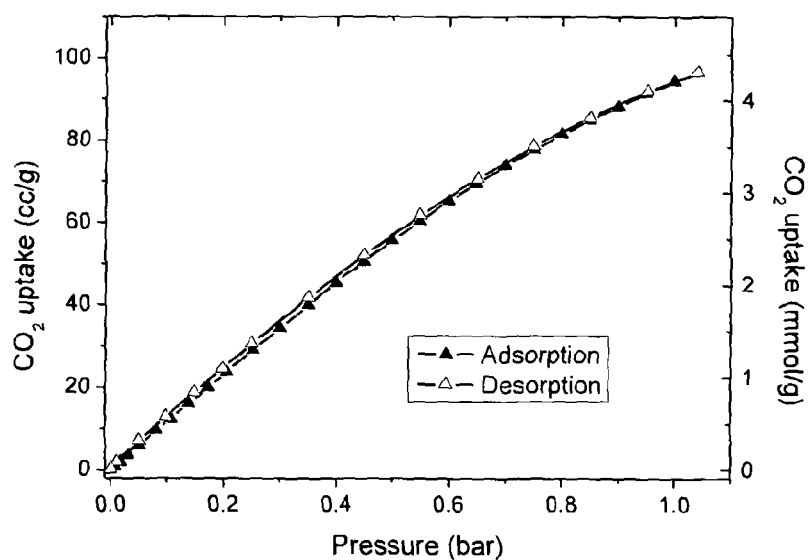
Figure 48:
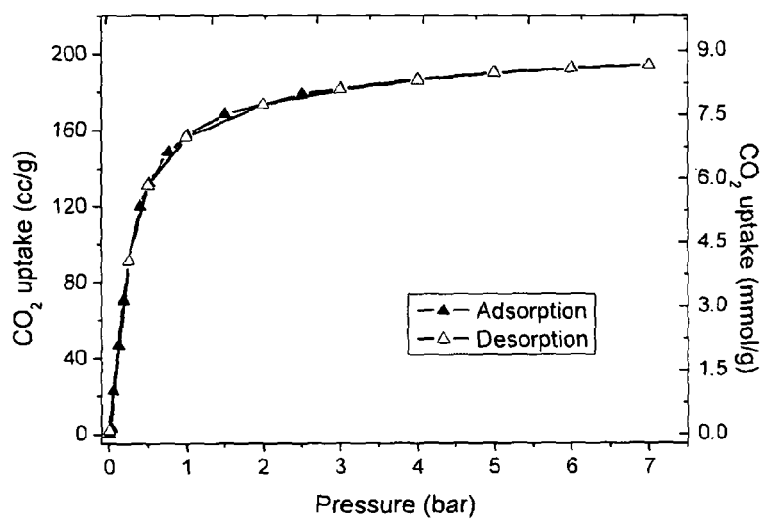
FIG. 48 illustrates high pressure CO$_2$ adsorption and desorption isotherms at 273 K for NOTT-300 (Al).
Figure 49:
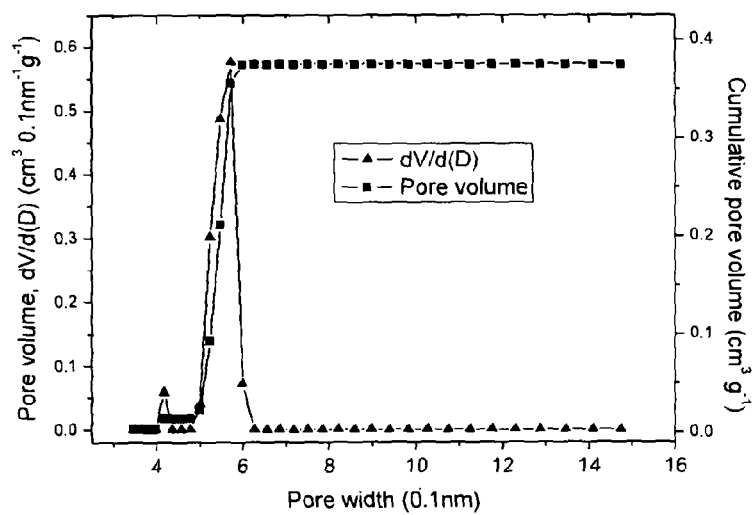
FIG. 49 is a pore size distribution (PSD) plot and cumulative pore volume for NOTT-300 (Al). Data were calculated the CO$_2$ adsorption isotherm at 273 K using DFT/Monte Carlo methods.
Figure 50:
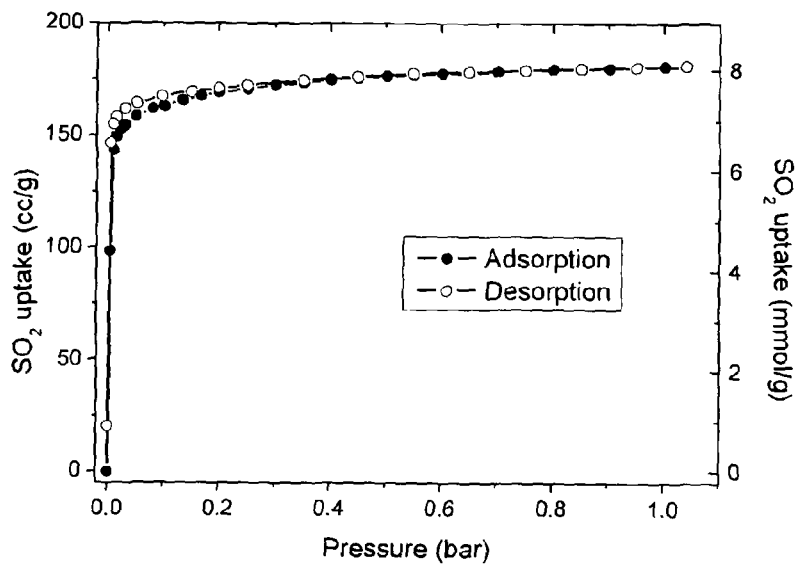
FIG. 50 is a comparison of the gas adsorption isotherms for NOTT-300 (Al) at 273 K and 0.15 bar. NOTT-300 (Al) exhibits highly selective uptake for CO$_2$ and SO$_2$ compared with CH$_4$, CO, N$_2$, H$_2$, 02 and Ar. The CO$_2$ selectivities, calculated from the ratio of isotherm uptakes at 0.15 bar, are 88, 99, 148, 197, 85, and 160 for CH$_4$, CO, N$_2$, H$_2$, O$_2$, and Ar, respectively. The SO$_2$ selectivities, calculated from the ratio of isotherm uptakes at 0.15 bar, are 250, 278, 418, 557, 239, and 451 for CH$_4$, CO, N$_2$, H$_2$, 02 and Ar, respectively.
Figure 51A:
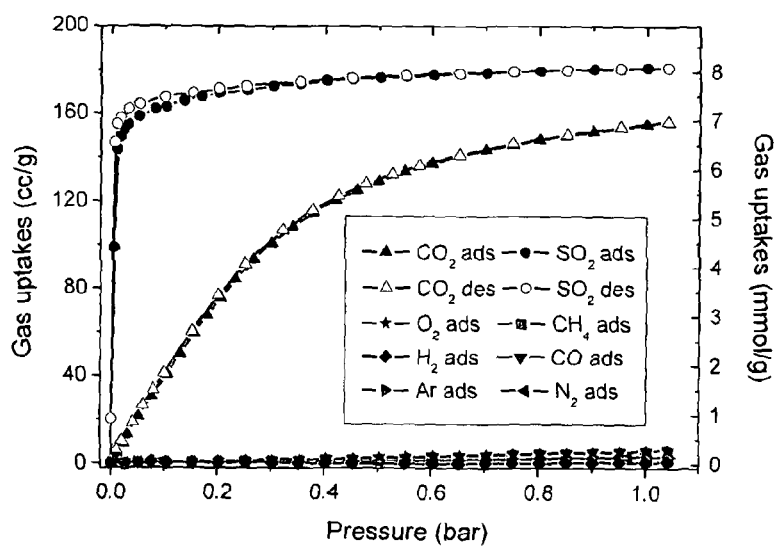
FIGS. 51(a)-51(d) illustrate SO$_2$ adsorption and desorption isotherms for NOTT-300 (Al) at (FIG. 51a) 273 K, (FIG. 51b) 283 K, (FIG. 51c) 293 K and (FIG. 51d) 303 K.
Figure 51B:
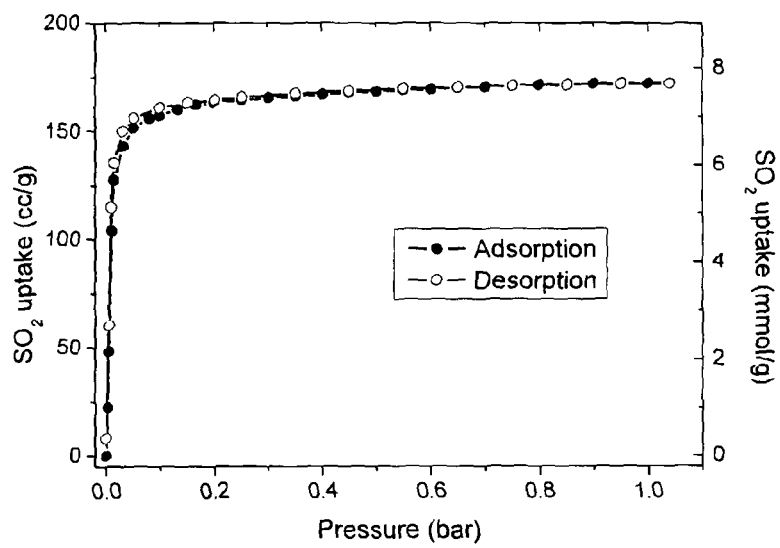
Figure 51C:
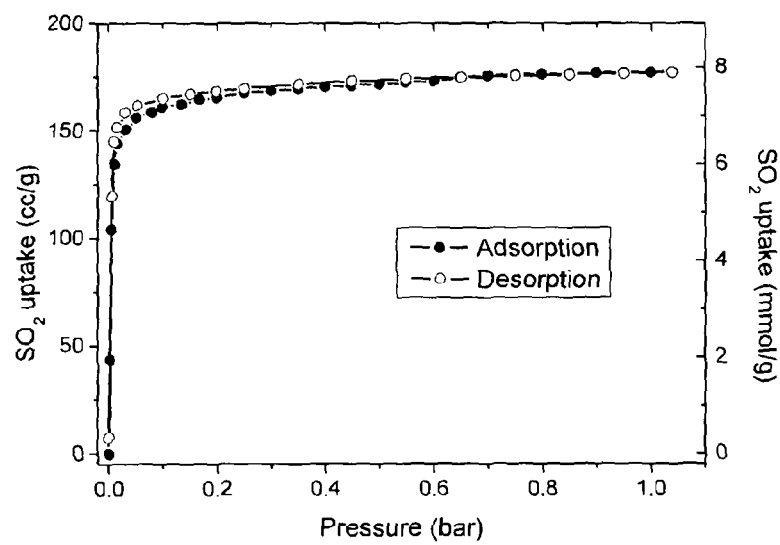
Figure 51D:
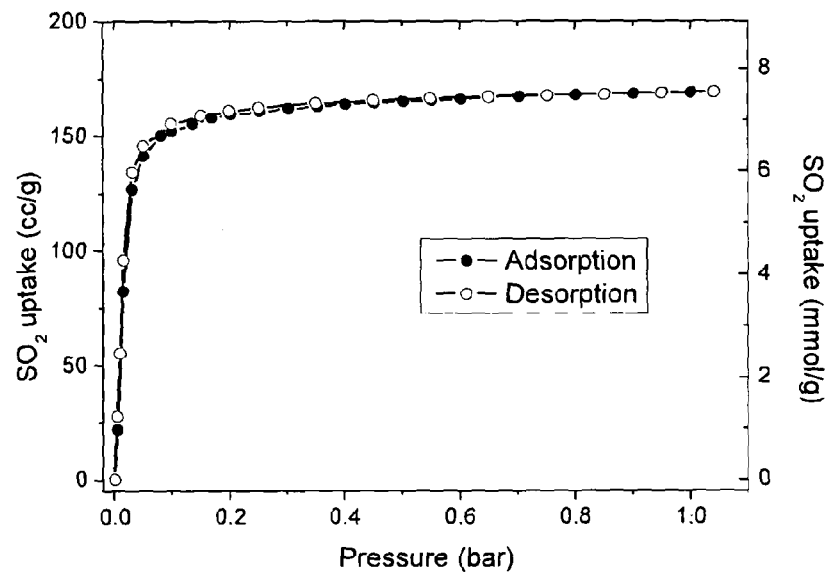

H$_2$ and N$_2$ isotherms at 77 K and the Ar isotherm at 87 K for NOTT-300 (Al) show, surprisingly, no apparent adsorption uptakes (FIG. 46). This is probably due to diffusion effects at low temperatures caused by the narrow pore channels. In contrast, low pressure CO$_2$ isotherms at ambient temperatures (273-303 K) show very high uptake capacities, with a maximum value of 7.0 mmol g$^{-1}$ at 273 K and 1.0 bar, representing one of the highest value observed for a MOF under these conditions (FIG. 3a).[9] The CO$_2$ uptake at 0.15 bar, which is relevant to the CO$_2$ partial pressure in flue gas, is 2.64 mmol g$^{-1}$ (FIG. 50). This uptake is higher than the value (0.682 mmol g$^{-1}$ at 0.15 bar and 298 K) observed by other workers for H$_3$[(Cu$_4$Cl)$_3$(BTTri)$_8$]-en (H$_3$BTTri=1,3, 5-tris(1H-1,2,3-triazol-5-yl)benzene),[22] but lower than the value observed by other workers for Mg$_2$(dobpdc) (mmen)$_{1.6}$(H$_2$O)$_{0.4}$ (dobpdc$^{4-}$=4,4'-dioxido-3,3'-biphenyldicarboxylate;mmen=N,N'dimethylethylenediamine) (3.14 mmol g$^{-1}$ at 0.15 bar and 313 K). Analysis of the CO$_2$ adsorption isotherm at 273 K by DFT/Monte-Carlo methods gives a surface area of 1370 m$^2$ g$^{-1}$, a pore size distribution centred at 5.7 Å, and a cumulative pore volume of 0.375 cm$^3$ g$^{-1}$ (FIG. 49), confirming the microporous nature of this material. Saturated CO$_2$ uptake at 273 K and 7.0 bar was found to be 8.7 mmol g$^{-1}$ (FIG. 48). These data are entirely consistent with the crystallographically-determined extra-framework pore volume of 0.433 cm$^3$ g$^{-1}$ and the channel window diameter of ~6.5 Å.

Interestingly, compared with the isotherm for CO$_2$, (kinetic diameter 3.30 Å), the isotherm for SO$_2$ (kinetic diameter 4.11 Å) exhibits higher uptakes with a maximum capacity of 8.1 mmol g$^1$ at 273 K and 1.0 bar, representing the highest value observed in the current literature. The SO$_2$ uptake increases sharply at low pressure (below 50 mbar) and reaches saturation at around 0.10 bar, giving a typical type-I isotherm. The very rapid uptake observed at low pressure indicates the presence of stronger interactions in NOTT-300 (Al)—SO$_2$ compared with NOTT-300 (Al)—CO$_2$. This is probably due to the high dipole moment of SO$_2$ (1.62 D compared with 0 D for CO$_2$) which results in stronger interactions of SO$_2$ with the pore surface of NOTT-300 (Al). The density of adsorbed CO$_2$ and SO$_2$ in NOTT-300 (Al) is unknown. By using a density of 1.032 g cm$^3$ of liquid $CO_2$ at 253 K or a density of 1.458 g cm$^3$ of liquid $SO_2$ at its boiling point of 263 K, it can be deduced that the volumes of $CO_2$ and $SO_2$ adsorbed in NOTT-300 (Al) at 1.0 bar and 273 K are 0.298 and 0.356 cm$^3$ g$^{-1}$, respectively. This corresponds to fillings of 69% and 82%, respectively, of the total crystallographically-determined pore volume of 0.433 cm$^3$ g$^{-1}$. At 7.0 bar, up to 89% of the total pore volume in NOTT-300 (Al) is filled by $CO_2$ molecules. These values are entirely reasonable considering that in each case the adsorption temperature lies above the relevant boiling point; moreover, in an isotherm experiment not all the void space within a porous material is necessarily accessible to the gaseous substrate. In contrast, under the same conditions the isotherms for $CH_4$, CO, $N_2$, $H_2$, $O_2$, and Ar show only surface adsorption by NOTT-300 (Al), with very low uptake of gas (0.04-0.25 mmol g$^{-1}$). Significantly, comparison of the gas adsorption isotherms (FIG. 3a) clearly shows ultra-high selectivities for $CO_2$ and $SO_2$ (e.g., $CO_2/CH_4$: 100; $CO_2/N_2$: 180; $CO_2/H_2$: >10$^5$; $SO_2/CH_4$: 3620; $SO_2/N_2$: 6522; $SO_2/H_2$: >10$^5$), indicating the potential of NOTT-300 (Al) for the selective capture of these harmful gases.

Figure 52A:
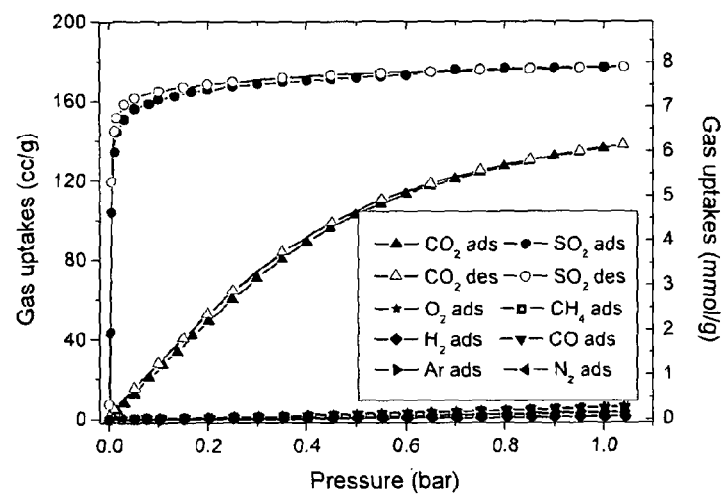
FIGS. 52(a)-52(c) show a comparison of the gas adsorption isotherms for NOTT-300 (Al) at 283 K (FIG. 52a), 293 K (FIG. 52b), 303 K (FIG. 52c) and 1.0 bar. NOTT-300 (Al) exhibits highly selective uptake for CO$_2$ and SO$_2$ compared with CH$_4$, CO, N$_2$, H$_2$, O$_2$, and Ar.
Figure 52B:
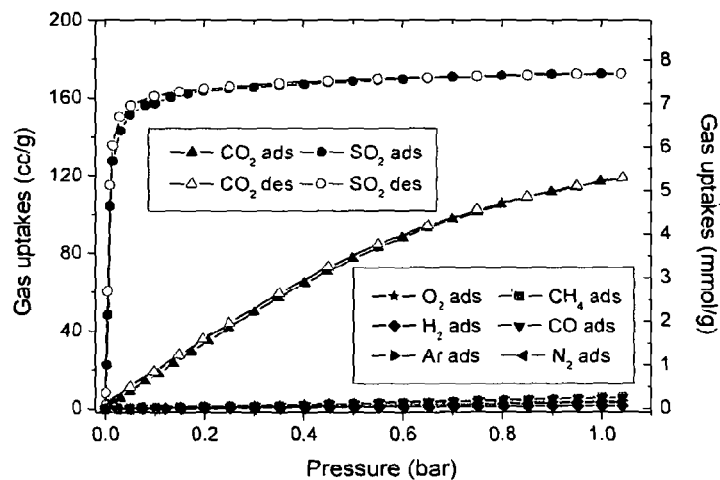
Figure 52C:
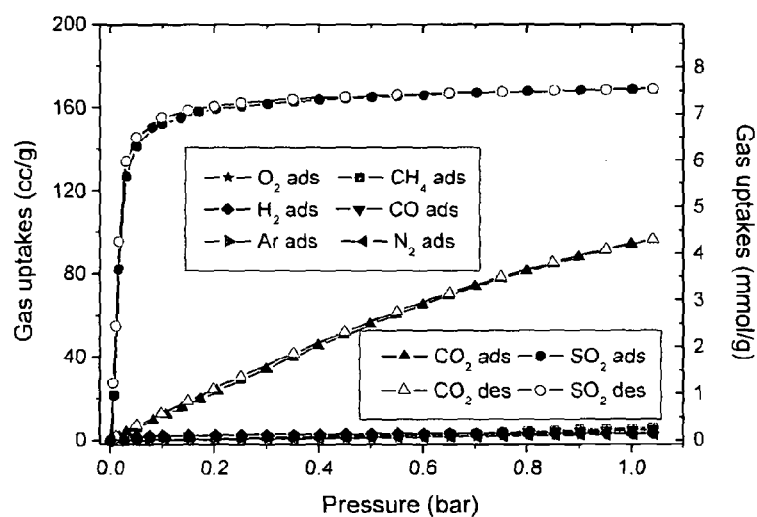

Gas adsorption isotherms ($CO_2$, $SO_2$, $CH_4$, $N_2$, CO, $O_2$, Ar, $H_2$) for NOTT-300 (Al) have also been measured at more ambient temperatures (i.e., 283, 293 and 303 K), where highly selective uptakes for $CO_2$ and $SO_2$ are confirmed (FIGS. 52(a)-52(c)), and the corresponding desorption isotherms exhibit full reversibility without hysteresis. This suggests that the adsorbed $CO_2$ and $SO_2$ gases can be readily released and that NOTT-300 (Al) can be re-generated at ambient temperatures without the need for heating, a factor which reduces the energy efficiency of traditional amine-based carbon capture systems.

In Situ Inelastic Neutron Scattering and Powder Diffraction Studies of of NOTT-300 (Al)

Direct visualisation of the interaction between $CO_2$ molecules and the NOTT-300 (Al) host is crucial to understanding the detailed binding mechanism and hence the observed high selectivities. Inelastic neutron scattering (INS) is a powerful neutron spectroscopy technique which has been used widely to investigate the $H_2$ binding interactions within various storage systems by exploiting the high neutron scattering cross-section of hydrogen (82.02 barns). However, this technique cannot directly detect the $CO_2$ binding interaction within a carbon capture system because the scattering cross-sections for carbon (5.551 barns) and oxygen (4.232 barns) are too small to obtain a clear neutron scattering signal. In this study, INS and DFT been successfully combined to visualise captured $CO_2$ molecules within NOTT-300 (Al) by investigating the change in the dynamics of the hydrogen atoms of the local MOF structure, including those of the hydroxyl groups and benzene rings of the ligand (FIG. 4). Calculation of the INS spectra from DFT vibrational analysis can be readily achieved, and the DFT calculations relate directly to the INS spectra, and, in the case of solid state calculations, there are no approximations other than the use of DFT eigenvectors and eigenvalues to determine the spectral intensities.[24] Comparison of INS spectra, measured at temperatures below 5 K to minimise the thermal motion of the adsorbed $CO_2$ and the framework host, reveals two major increases in peak intensity on going from bare NOTT-300 (Al) to NOTT-300 (Al).1.0$CO_2$: peak I occurs at low energy transfer (30 meV) and peak II at high energy transfer (125 meV). Moreover, the peaks in the range 100-160 meV are slightly shifted to higher energies in NOTT-300 (Al).1.0$CO_2$ (FIG. 4b), indicating a stiffening of the motion of the NOTT-300 (Al) host upon $CO_2$ adsorption.

Figure 4A:
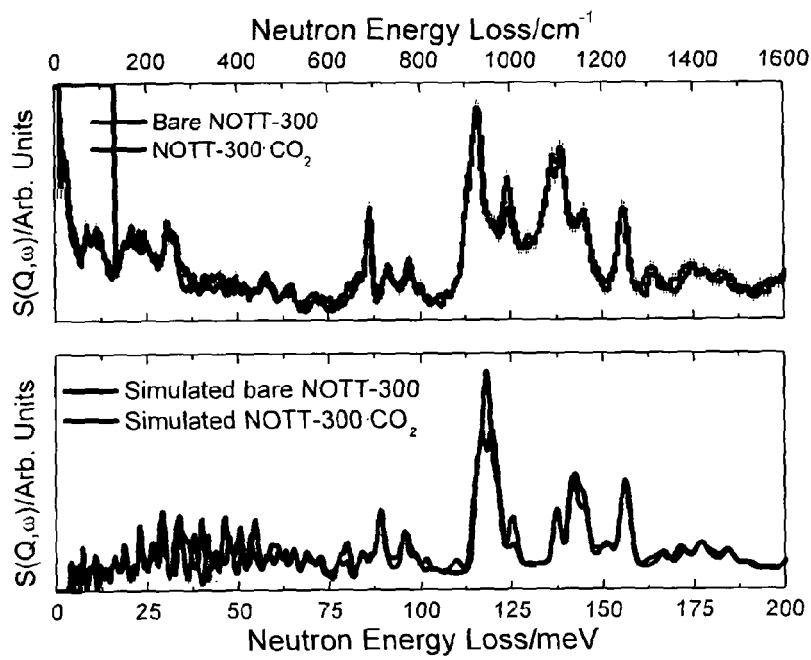
FIGS. 4($a$)-4($d$) show in situ inelastic neutron scattering (INS) spectra and simulated $CO_2$ positions in the pore channel of NOTT-300 (Al)
Figure 4B:
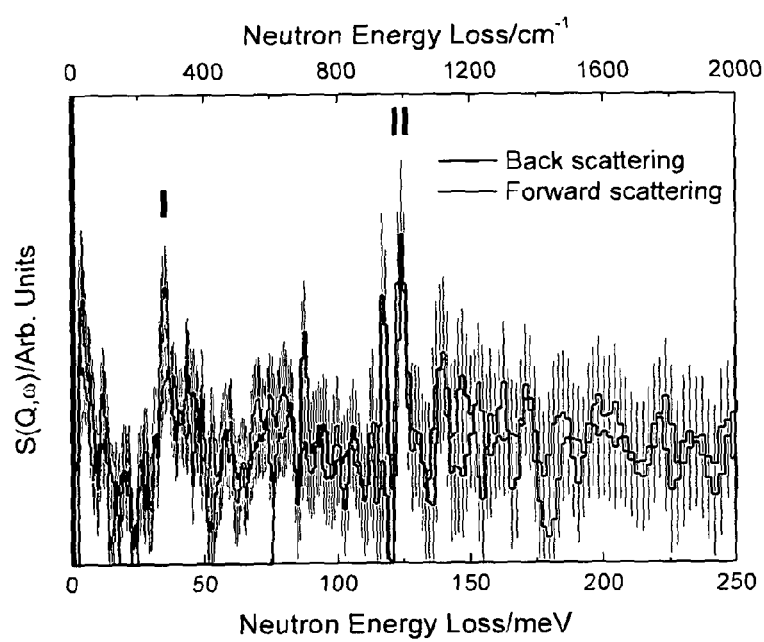
Figure 4C:
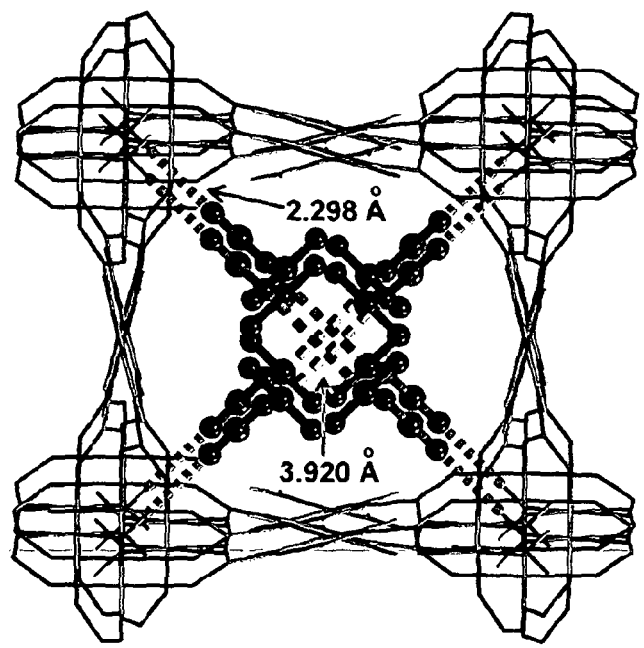
Figure 4D:
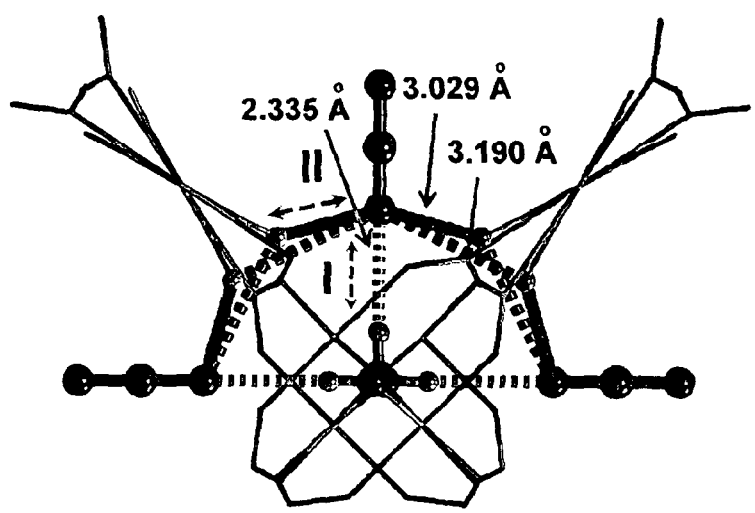

To understand these changes, DFT calculations have been used to simulate the INS spectra and optimise the structures for NOTT-300 (Al) and NOTT-300 (Al).1.0$CO_2$. The INS spectra derived from these calculations show good agreement with experimental spectra and confirm that the adsorbed $CO_2$ molecules interact end-on to the hydroxyl groups. The O . . . H distance between the $CO_2$ molecule and the hydroxyl group is 2.335 Å, indicating a moderate-to-weak hydrogen bond (See Table S13 in the supplementary section of this specification). The optimised C—O bond distances in $CO_2$ are 1.183 Å (hydrogen-bonded end) and 1.178 Å (free end), and the <OCO bond angle is 180°. Each adsorbed $CO_2$ molecule is also surrounded by four aromatic C—H groups, forming weak cooperative supramolecular interactions between O(δ-) of $CO_2$ and H(δ+) from —CH [O . . . H=3.029, 3.190 Å, each occurring twice]. Specifically, peak I can be assigned to the O—H groups wagging perpendicular to the Al—O—Al direction, attributed to the presence of the $CO_2$, and peak II to the wagging of the four aromatic C—H groups on four benzene rings adjacent to each $CO_2$ molecule in conjunction with the wagging of the OH group along the Al—O—Al direction (FIG. 4d and film in SI). Thus, a total of five hydrogen atoms H(δ+) interact cooperatively with the O(δ-) charge centres of $CO_2$ molecules in the channel via moderate-to-weak hydrogen bonds and supramolecular interactions.

The preferred binding sites for $CO_2$ molecules within NOTT-300 (Al) have also been determined by in situ PXRD analysis which also confirms end-on binding of $CO_2$ molecules to the hydroxyl group [O . . . H=2.298(10) Å]. The weaker supramolecular contacts from surrounding C—H groups to the O(δ-) charged centres of $CO_2$ molecules in the channel [O . . . H=3.021(31), 3.171(22) Å, each occurring twice] are also observed. This PXRD analysis is in excellent agreement with the INS model obtained independently from DFT modelling with regard to both hydrogen-bonding and the combination of supramolecular binding interactions. Additionally, a second $CO_2$(II) site has been identified in NOTT-300 (Al).3.2$CO_2$ studied by PXRD. This second site interacts principally with the first $CO_2$ via dipole interaction [O(I) . . . C(II)=3.920 Å], forming an edge-on intermolecular $CO_2$ network [O(I) . . . O(II)=2.713(28) Å] along the pore channel that is reminiscent of solid $CO_2$ (FIG. 4c).

Figure 54:
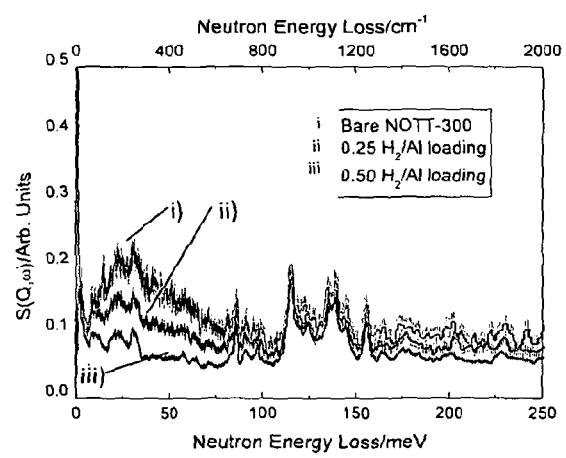
FIG. 54 is a comparison of INS spectra for bare NOTT-300 (Al), 0.25 H$_2$/Al and 0.5 H$_2$/Al loaded-NOTT-300 (Al).
Figure 55A:
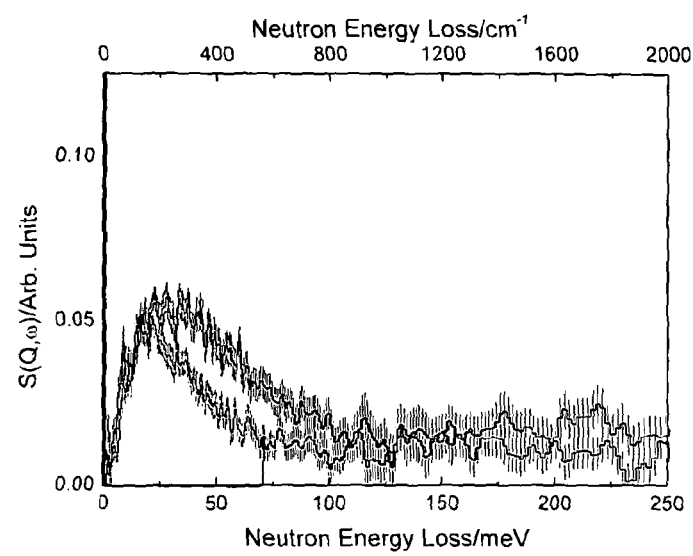
FIG. 55(a) is a difference INS spectra plot for forward and back scattering between bare and 0.25H$_2$/Al-loaded NOTT-300 (Al). The broad hump shows recoil of hydrogen; a very small and poorly defined peak at 10 meV suggests a very weak interaction.
Figure 55B:
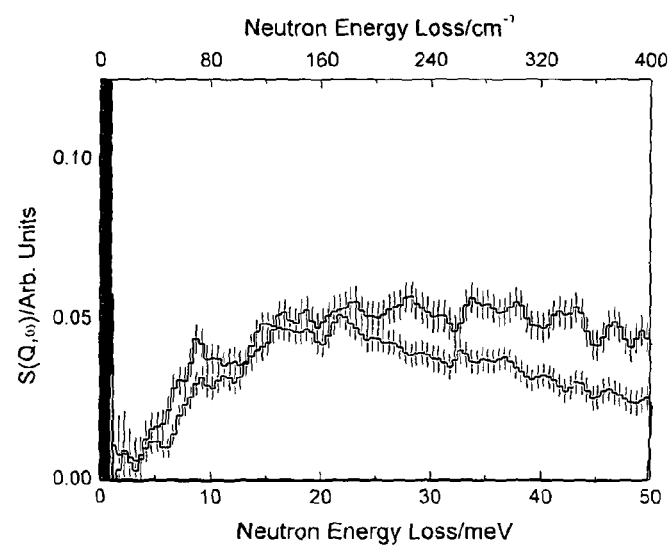
FIG. 55(b) shows a detailed view of where the low energy transfer has been scaled up.
Figure 56A:
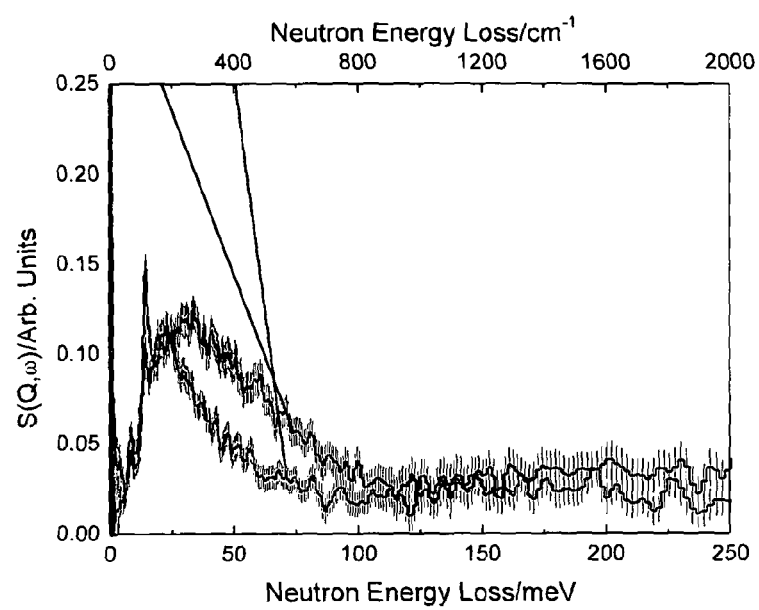
FIG. 56(a) is a difference INS spectra plot for forward and back scattering between bare and 0.5 H$_2$/Al-loaded NOTT-300 (Al). The broad hump shows recoil of hydrogen. The peak at 10 meV is still broad and very weak, but can be seen to have increased in intensity slightly. Furthermore, an additional peak at ~15 meV can be observed. This peak is very close to the rotational line of hydrogen (14.7 meV), further indicating that the interactions between the hydrogen and the NOTT-300 (Al) framework are very weak.
Figure 56B:
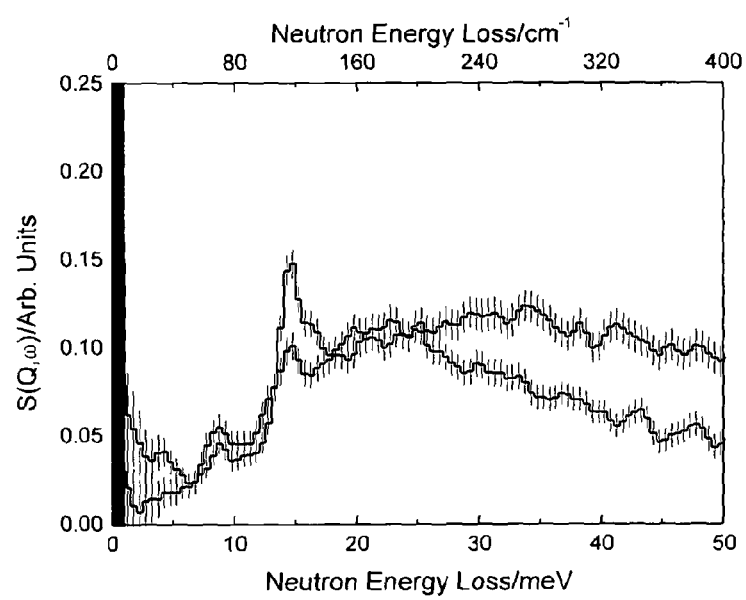
FIG. 56(b) shows a detailed view of where the low energy transfer has been scaled up.
Figure 57A:
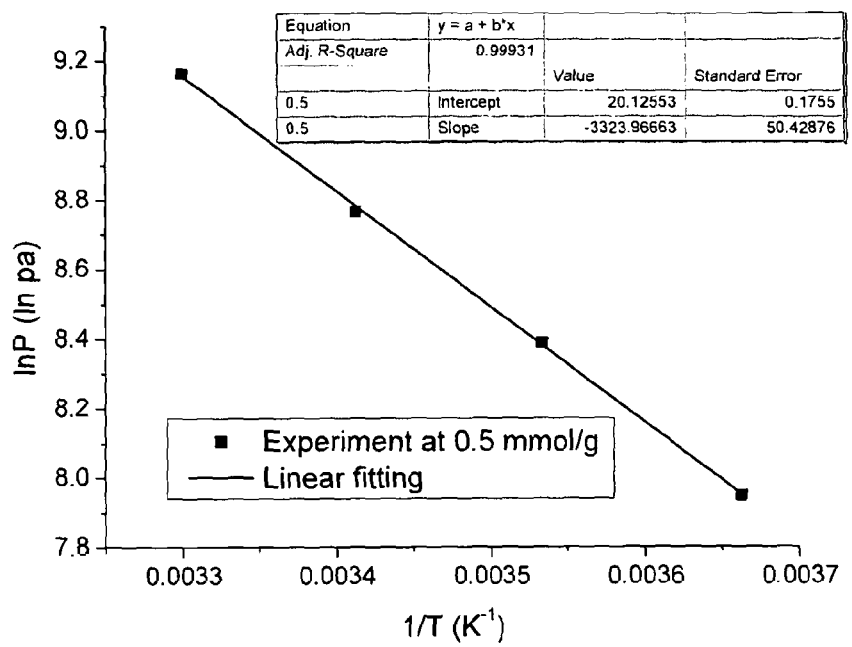
FIGS. 57(a)-57(d) provide linear fitting of Van't Hoff plots for the CO$_2$ adsorption isotherms at (FIG. 57a) 0.5, (FIG. 57b) 1.0, (FIG. 57c) 1.5 and (FIG. 57d) 2.0 mmol g$^{-1}$ loadings.
Figure 57B:
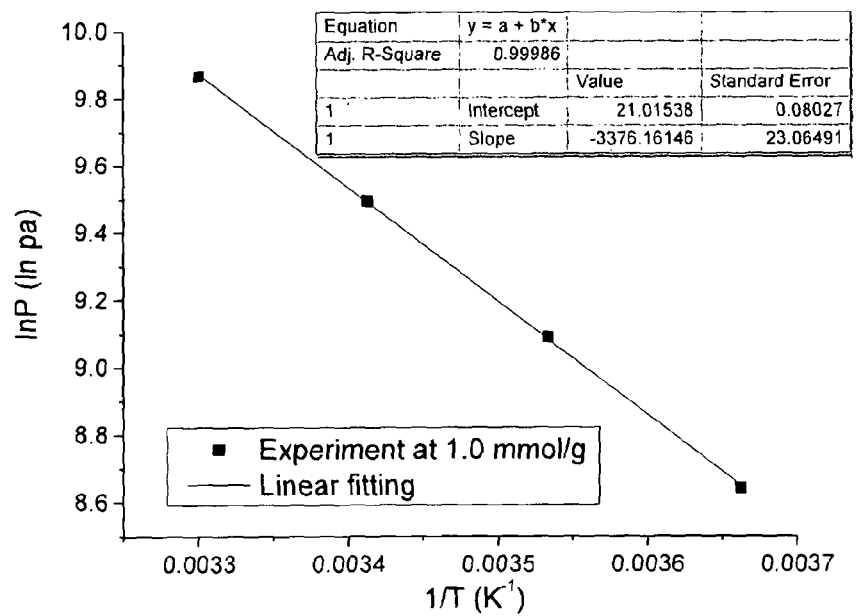
Figure 57C:
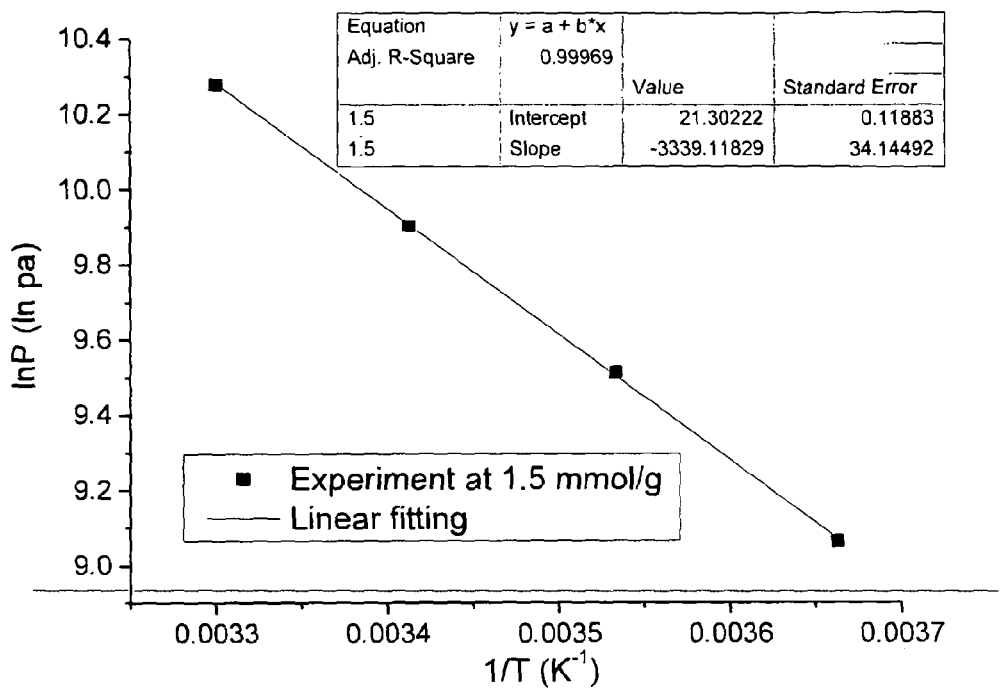
Figure 57D:
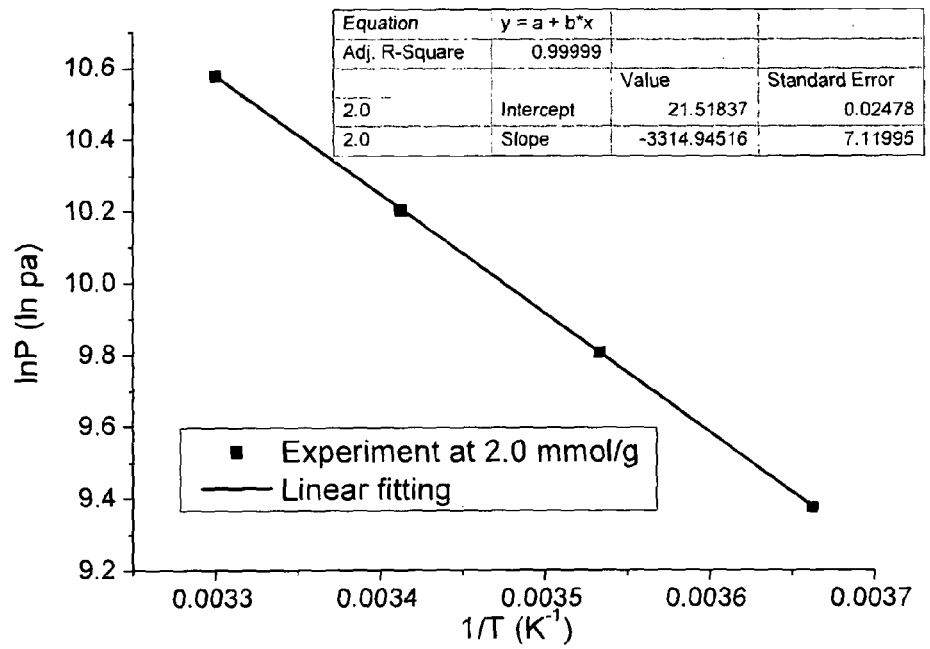
Figure 58A:
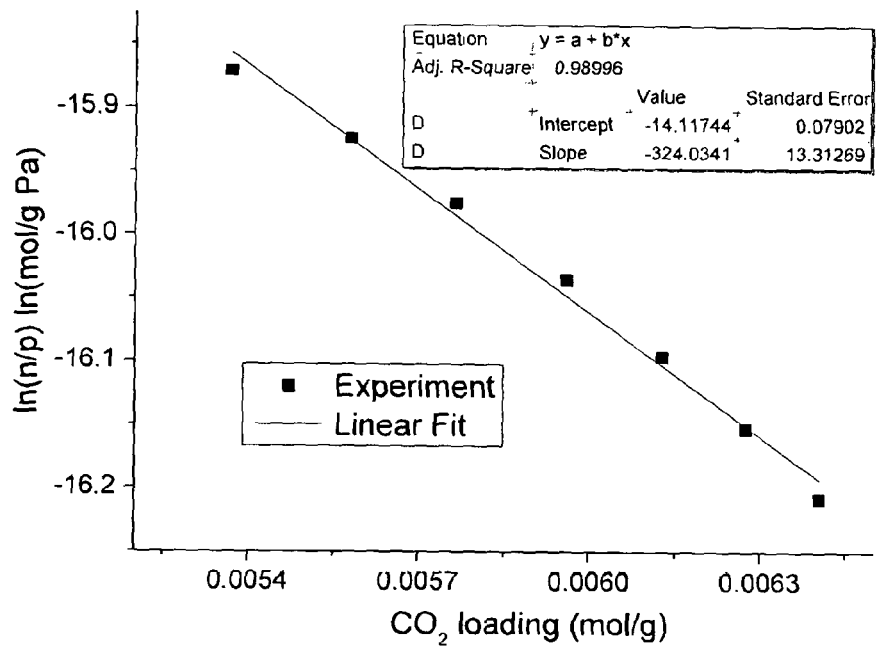
FIGS. 58(a)-58(b) provide linear virial fitting plots for the adsorption isotherms for (FIG. 58a) CO$_2$ and (FIG. 58b) SO$_2$ for NOTT-300(Al) at 273 K.
Figure 58B:
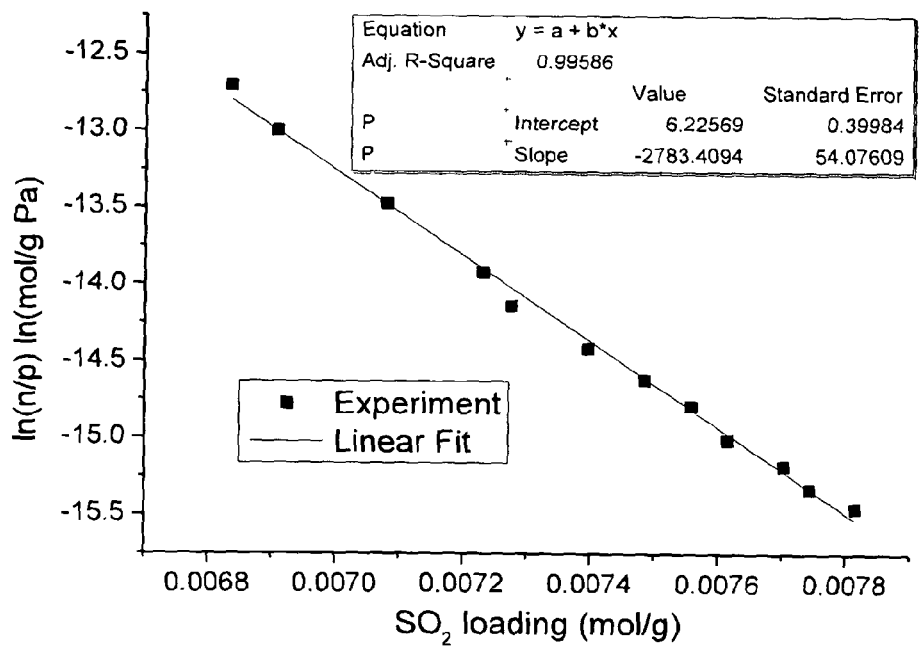
Figure 59A:
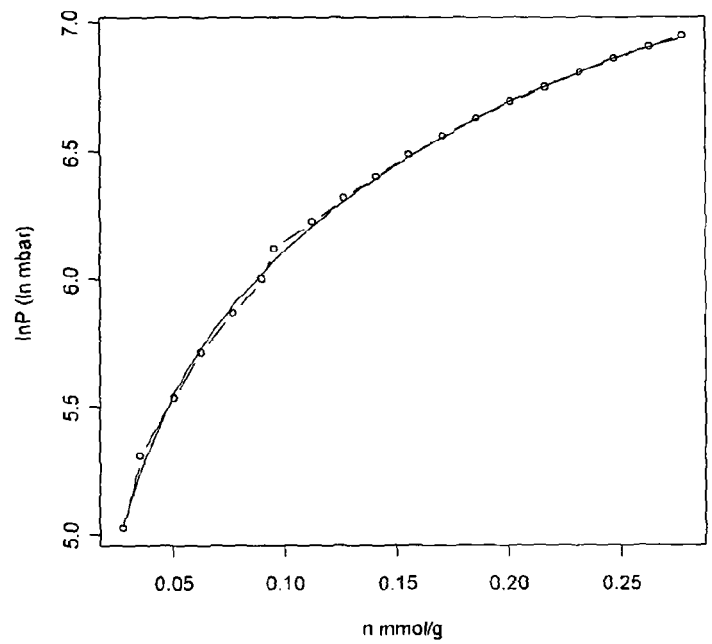
FIGS. 59(a)-59(e) provide non-linear virial fitting plots for the adsorption isotherms for (FIG. 59a) CO, (FIG. 59b) CH$_4$, (FIG. 59c) O$_2$, (FIG. 59d) N$_2$ and (FIG. 59e) Ar for NOTT-300(Al) at 273 K.
Figure 59B:
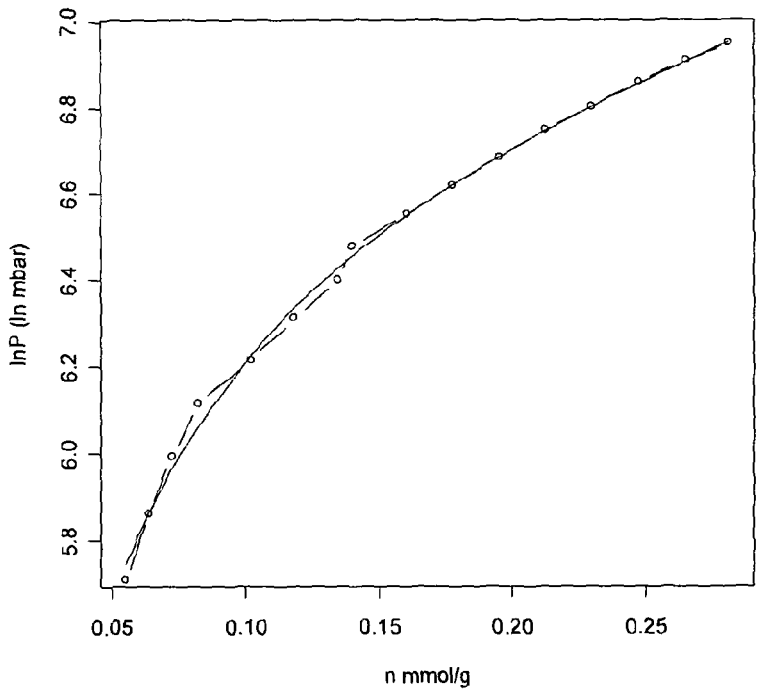
Figure 59C:
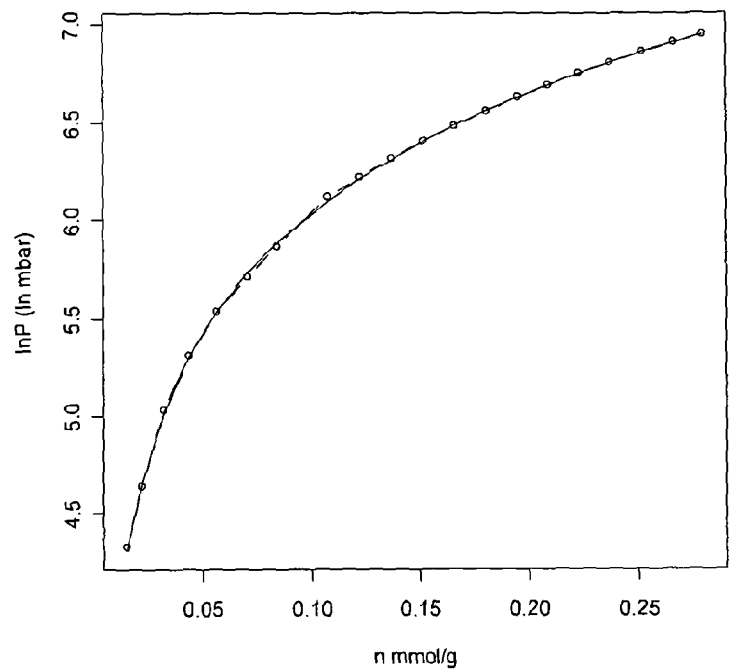
Figure 59D:
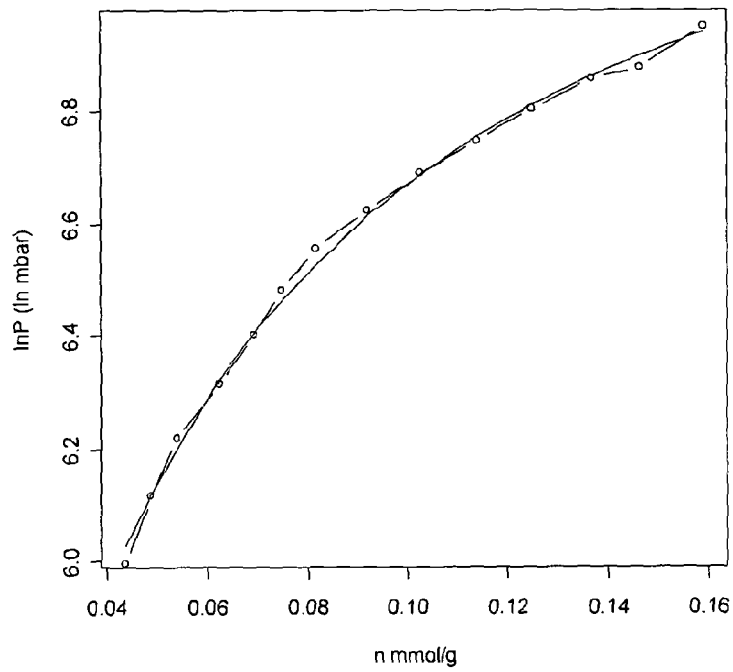
Figure 59E:
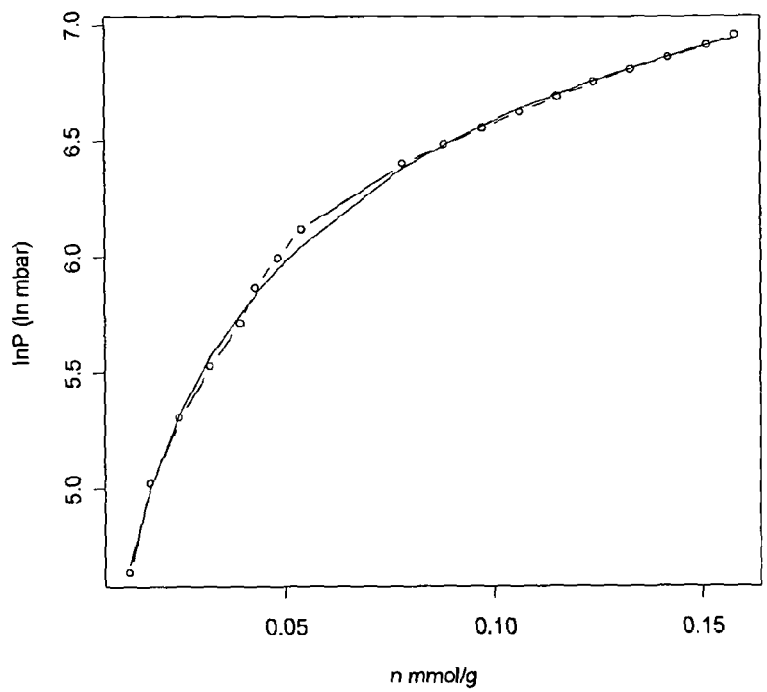
Figure 60A:
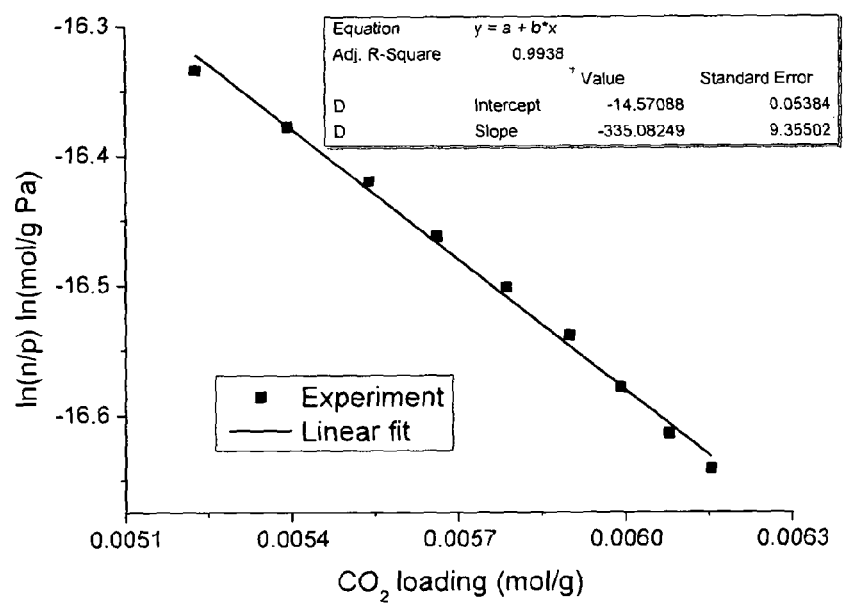
FIGS. 60(a)-60(b) provide linear virial fitting plots for the adsorption isotherms for (FIG. 60a) CO$_2$ and (FIG. 60b) SO$_2$ for NOTT-300(Al) at 283 K.
Figure 60B:
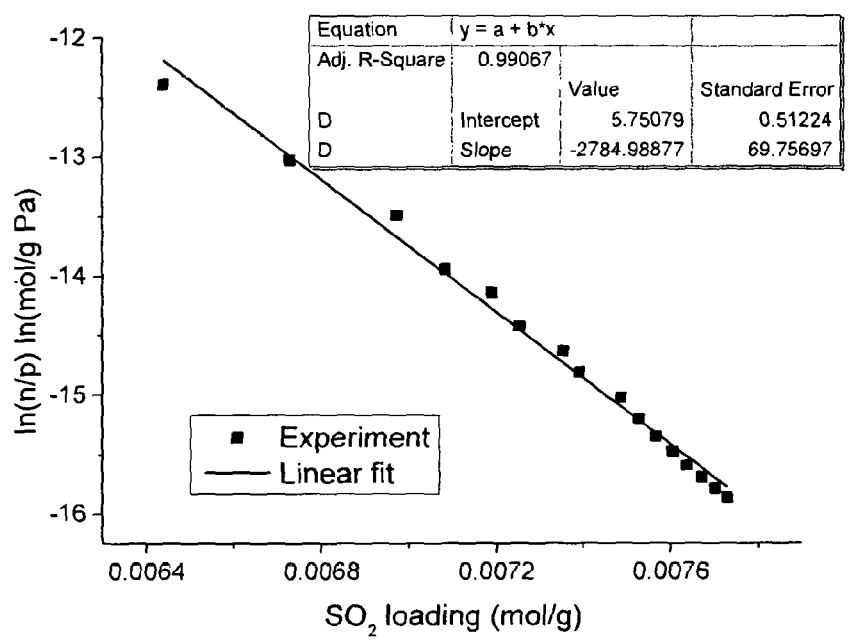
Figure 61A:
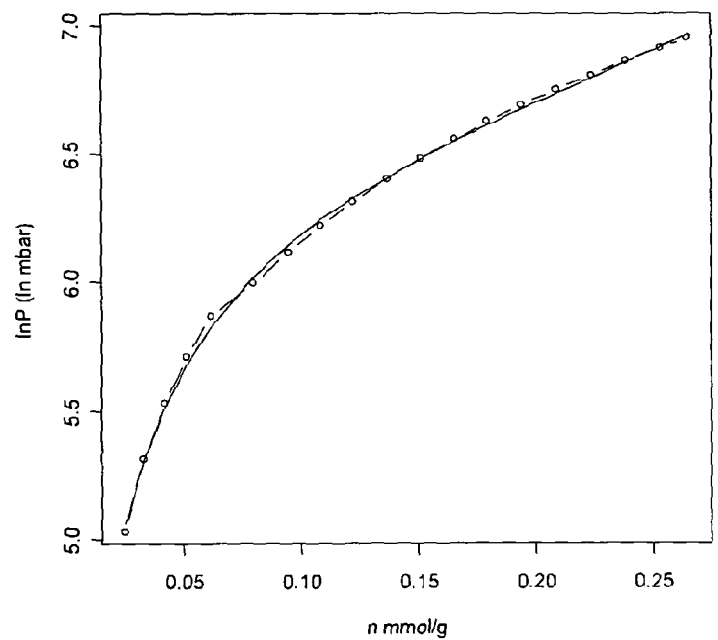
FIGS. 61(a)-61(e) provide non-linear virial fitting plots for the adsorption isotherms for (FIG. 61a) CO, (FIG. 61b) CH$_4$, (FIG. 61c) O$_2$, (FIG. 61d) N$_2$ and (FIG. 61e) Ar for NOTT-300(Al) at 283 K.
Figure 61B:
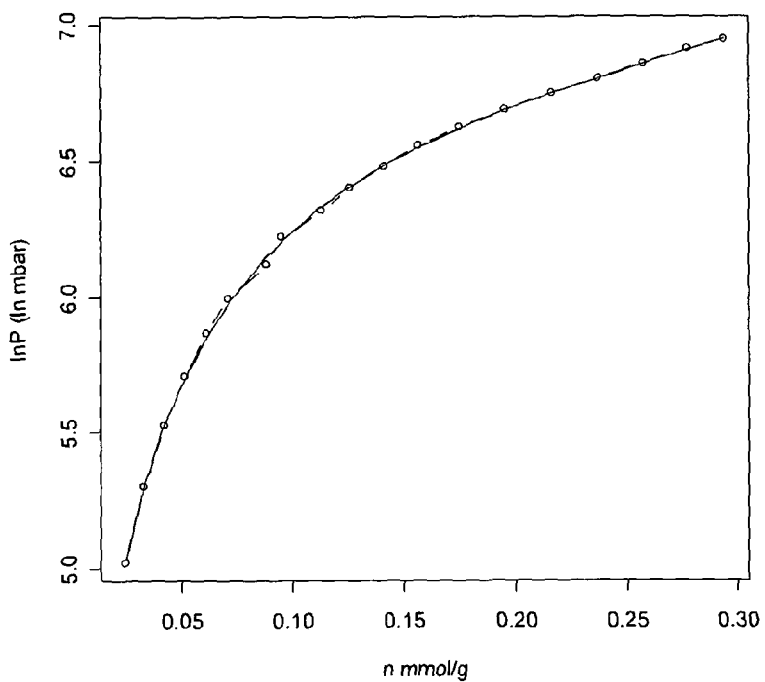
Figure 61C:
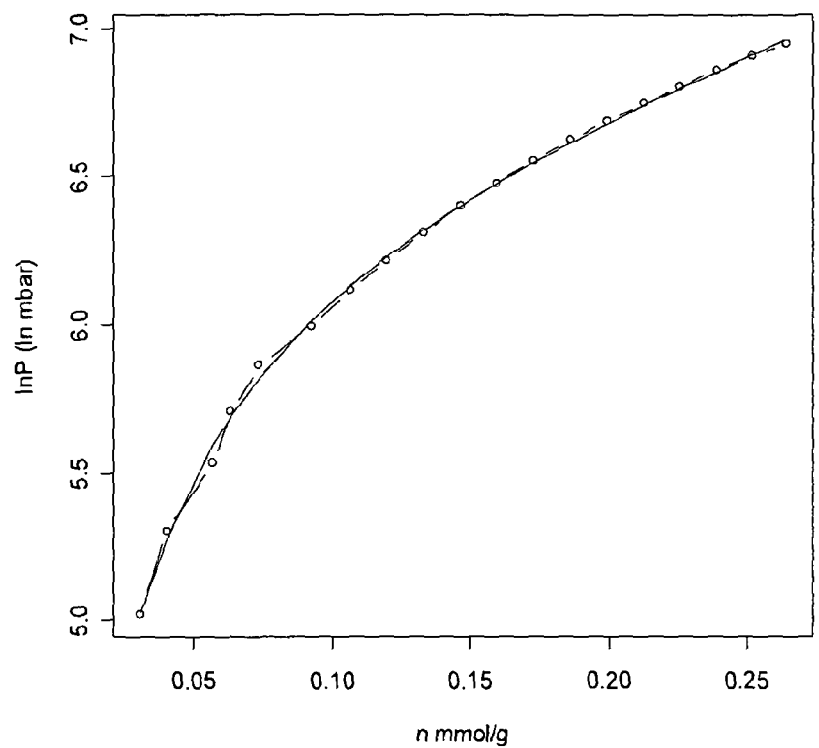
Figure 61D:
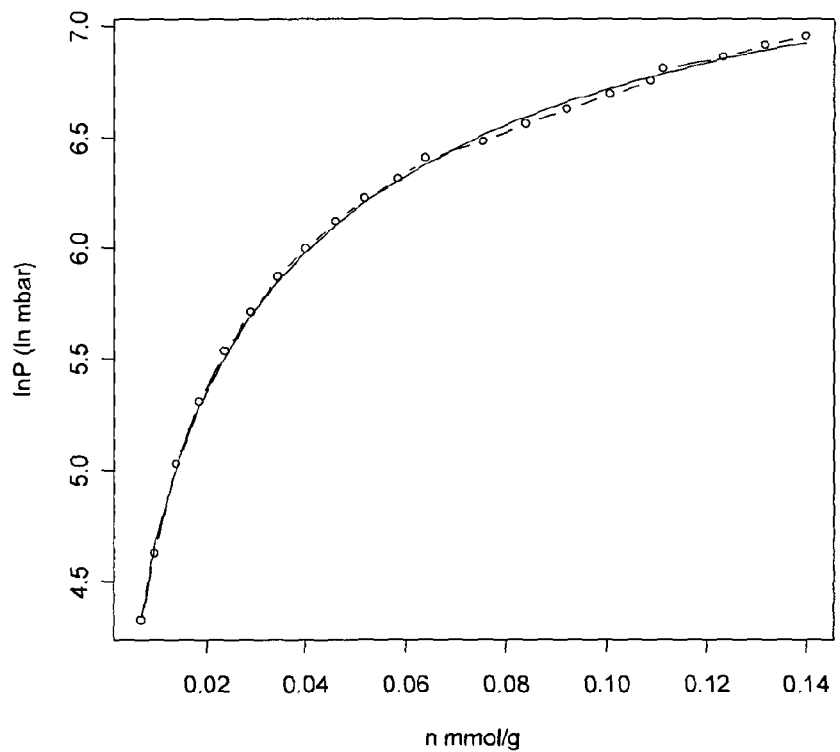
Figure 61E:
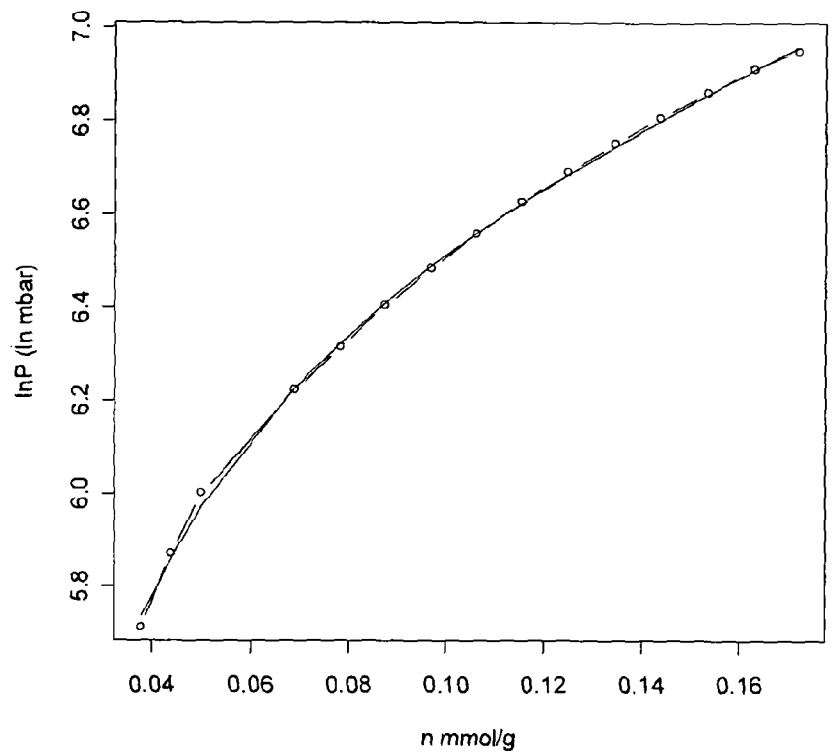
Figure 62A:
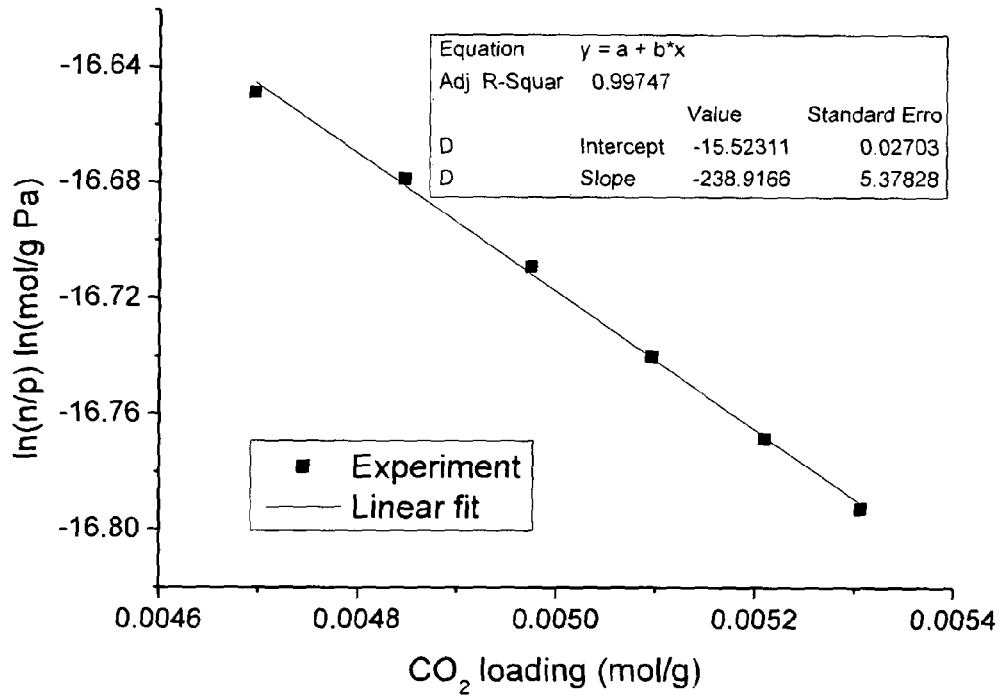
FIGS. 62(a)-62(b) provide linear virial fitting plots for the adsorption isotherms for (FIG. 62a) CO$_2$ and (FIG. 62b) SO$_2$ for NOTT-300(Al) at 293 K.
Figure 62B:
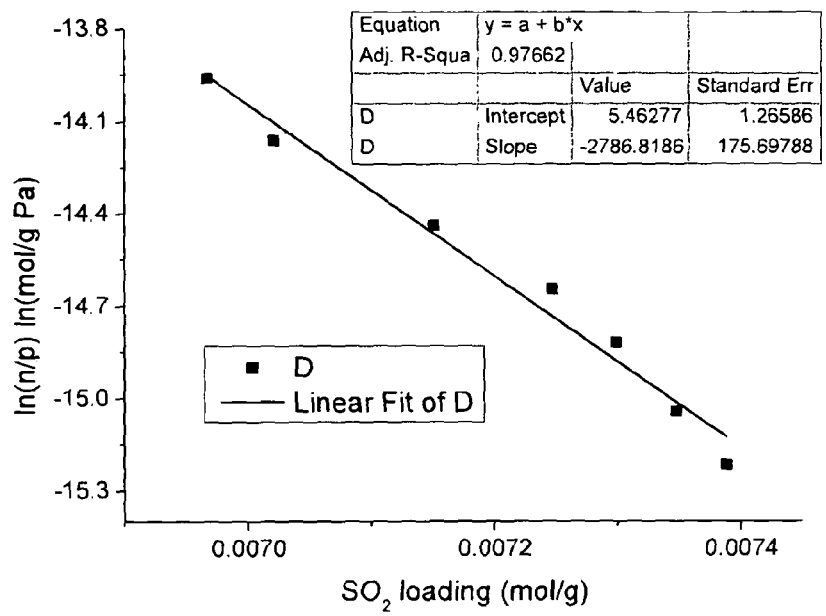
Figure 63A:
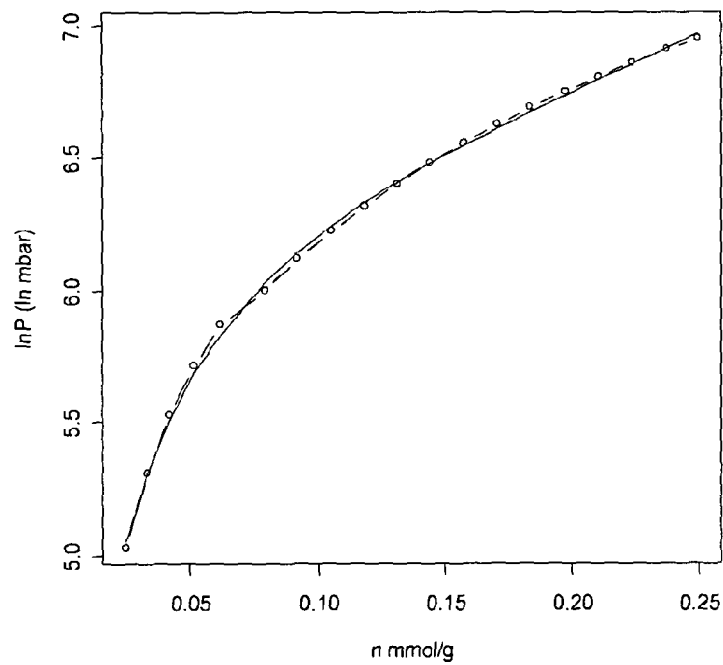
FIGS. 63(a)-63(e) provide non-linear virial fitting plots for the adsorption isotherms for (FIG. 63a) CO, (FIG. 63b) CH$_4$, (FIG. 63c) O$_2$, (FIG. 63d) N$_2$ and (FIG. 63e) Ar for NOTT-300 at 293 K.
Figure 63B:
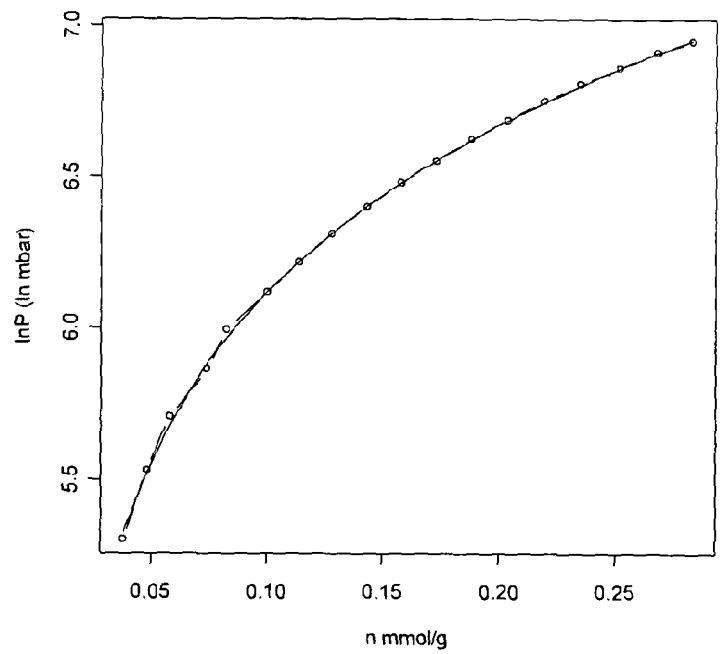
Figure 63C:
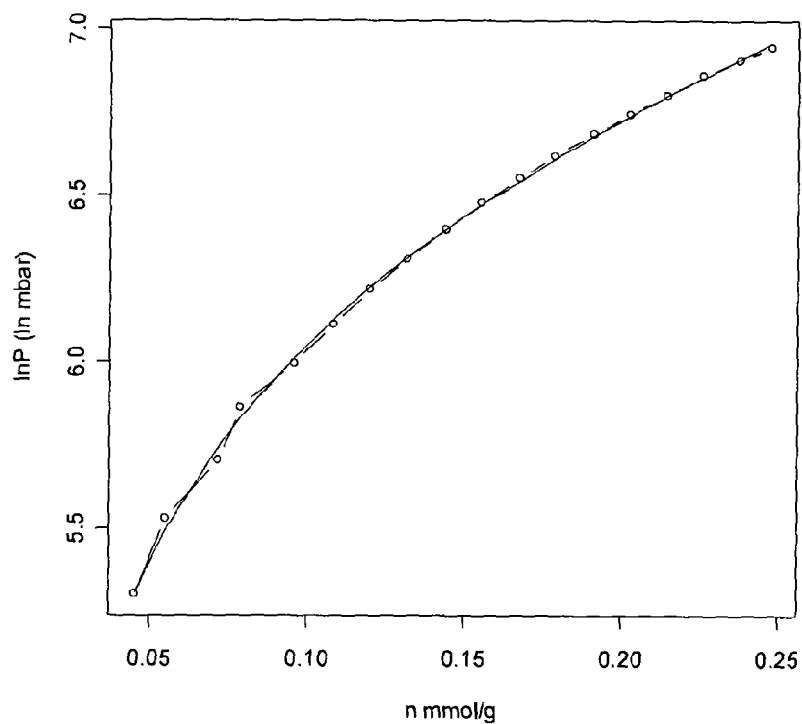
Figure 63D:
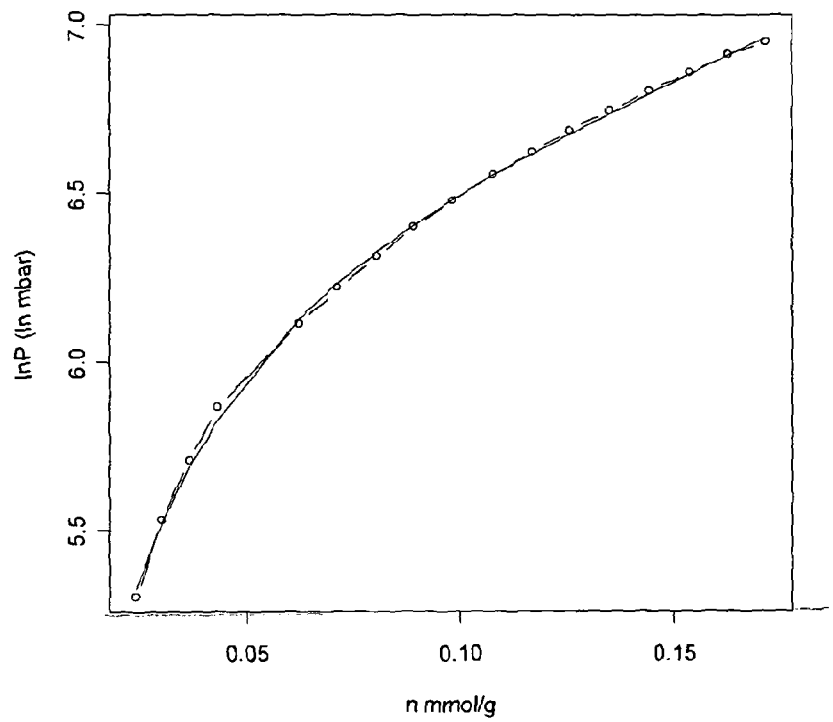
Figure 63E:
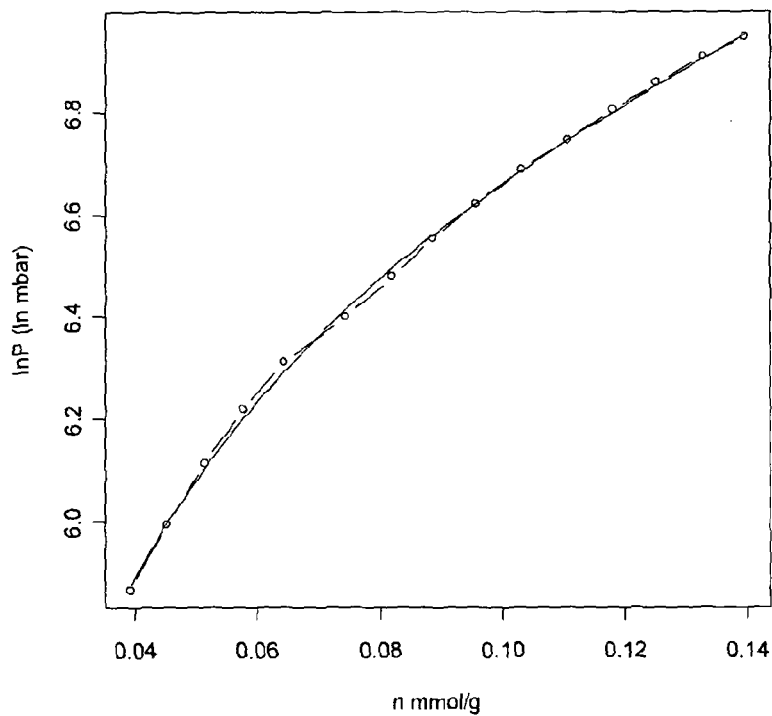
Figure 64A:
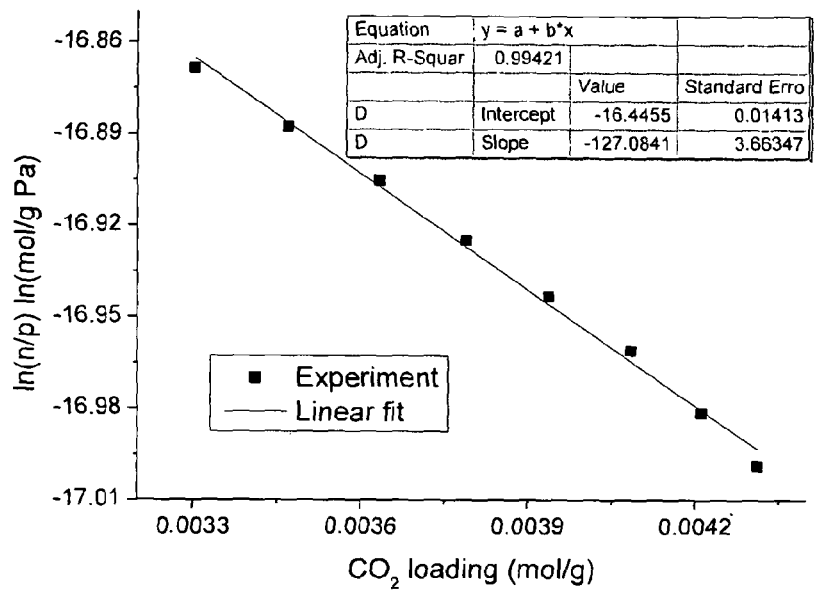
FIGS. 64(a)-64(b) provide linear virial fitting plots for the adsorption isotherms for (FIG. 64a) CO$_2$ and (FIG. 64b) SO$_2$ for NOTT-300(Al) at 303 K.
Figure 64B:
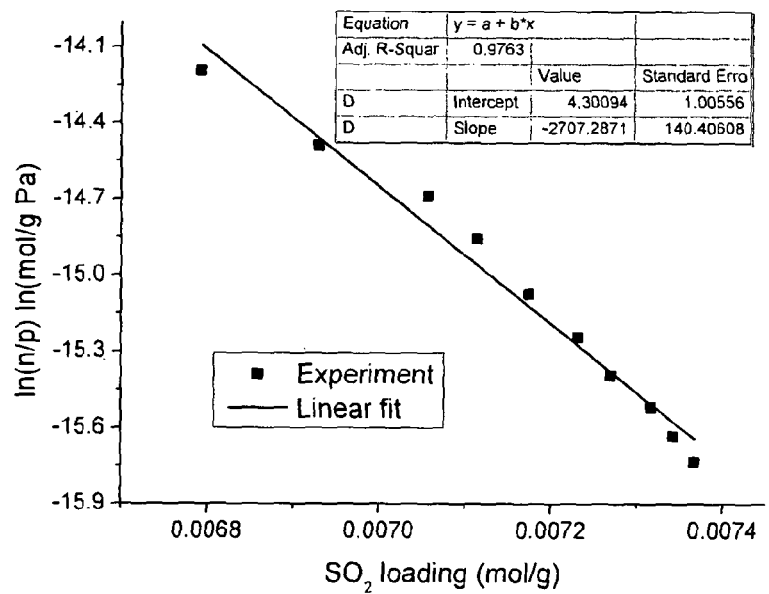
Figure 65A:
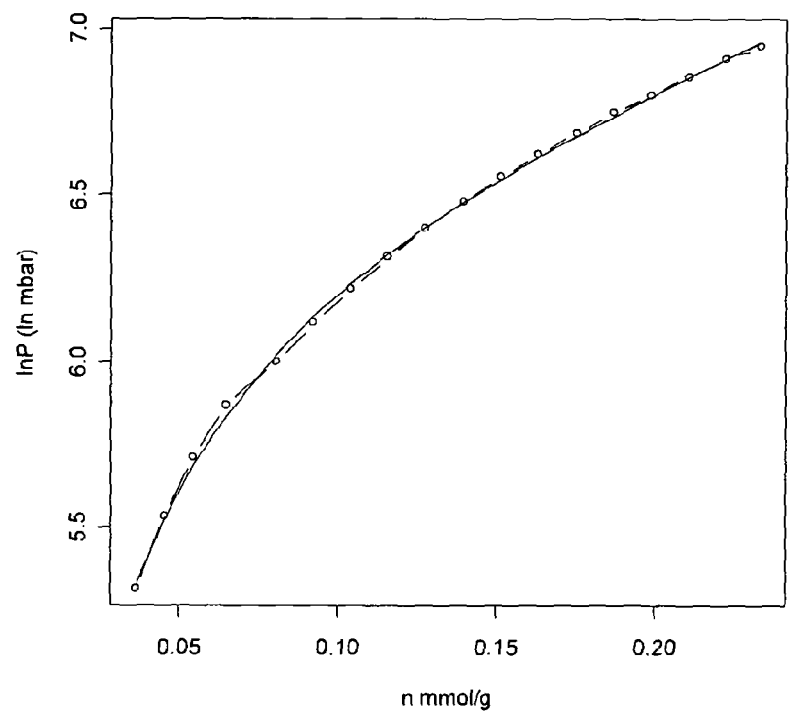
FIGS. 65(a)-65(e) provide non-linear virial fitting plots for the adsorption isotherms for (FIG. 65a) CO, (FIG. 65b) CH$_4$, (FIG. 65c) O$_2$, (FIG. 65d) N$_2$ and (FIG. 65e) Ar for NOTT-300(Al) at 303 K.
Figure 65B:
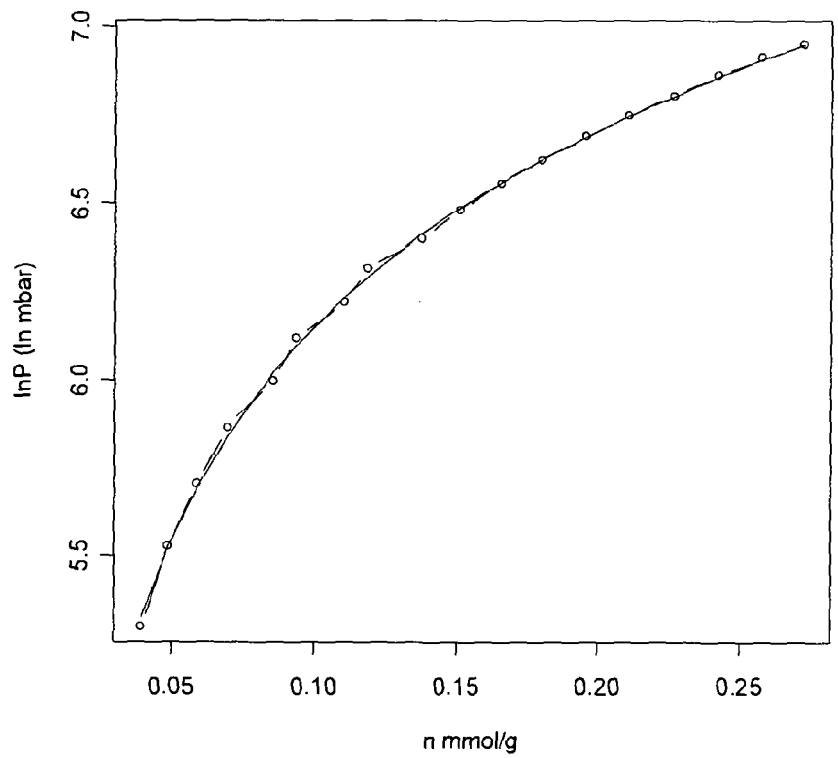
Figure 65C:
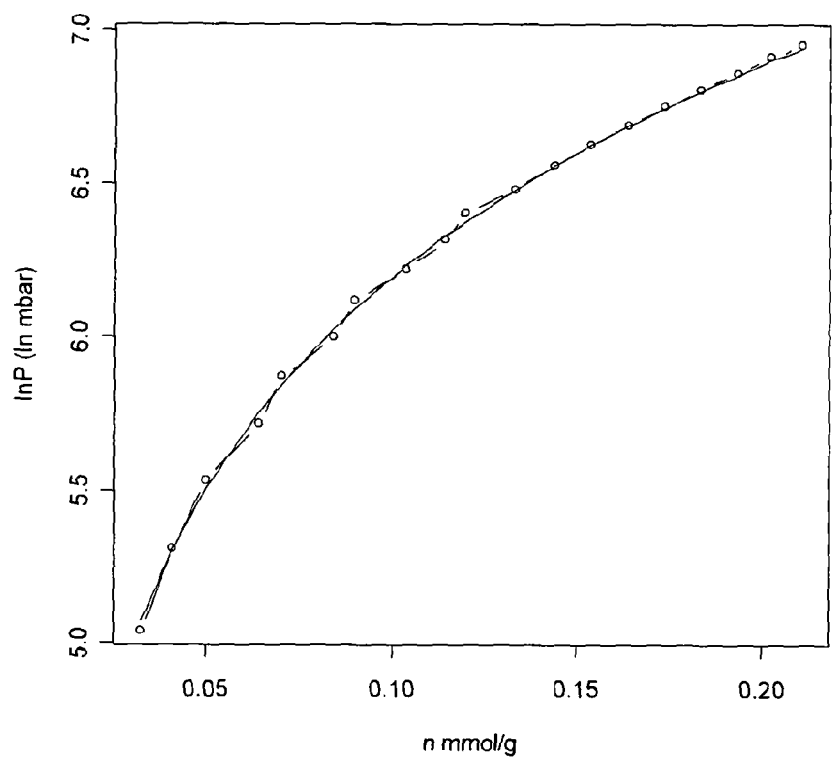
Figure 65D:
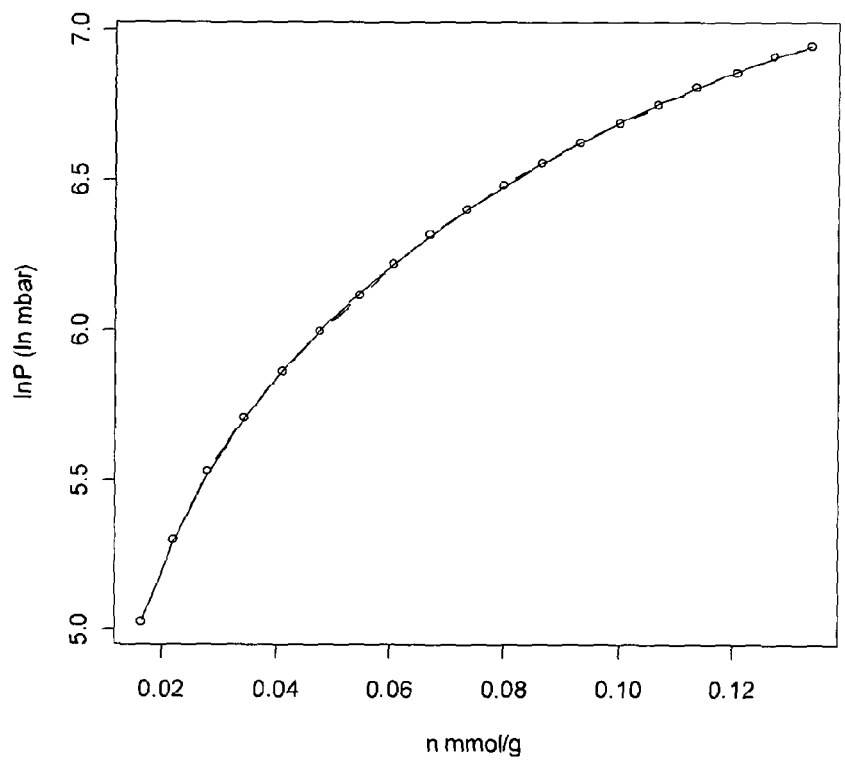
Figure 65E:
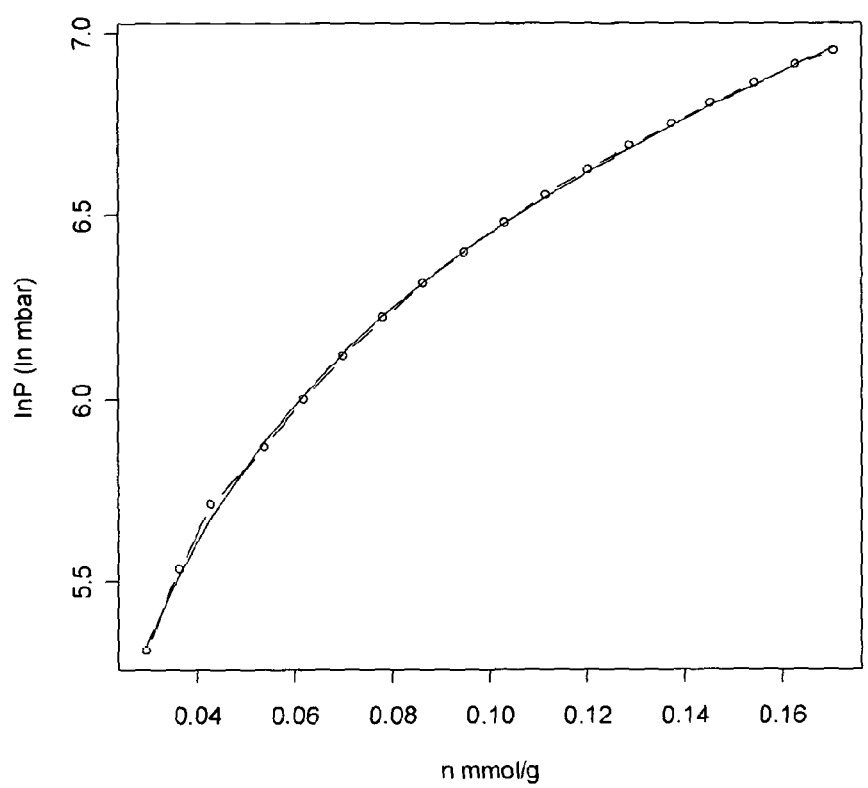

In order to understand why low uptakes are observed for some gases while high selectivity for $CO_2$ is achieved, the interactions between $H_2$ and NOTT-300 (Al) were probed The INS spectra of NOTT-300 (Al).1.0$H_2$ show an overall increase in signal upon $H_2$ loading, indicating adsorption of $H_2$ by NOTT-300 (Al) at below 40 K (FIG. 54). The difference INS spectra, measured at below 5 K, between bare NOTT-300 (Al) and NOTT-300 (Al).1.0$H_2$ show a series of features that resemble the signal of liquid molecular $H_2$. Significantly, the sharp rotational peak usually observed around 14.7 meV as a prominent feature in the INS of molecular $H_2$ in the solid state or adsorbed on surface is not observed here. This suggests a 1D fluid-like recoil motion of the $H_2$ along the channel[25,26] consistent with extremely weak interactions and low uptake of $H_2$ in NOTT-300 (Al) (FIGS. 55(a), 55(b), 56(a), and 56(b)).

Figure 5A:
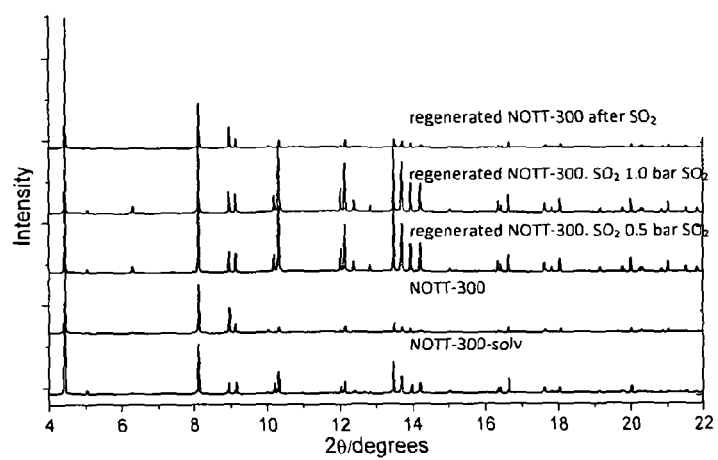
FIGS. 5($a$)-5($c$) show in-situ synchrotron X-ray powder diffraction patterns and refined $SO_2$ positions in the pore channel of NOTT-300 (Al)

In order to determine the reasons for the high selectivity and high uptake capacity, the preferred binding sites for $SO_2$ molecules within NOTT-300 (Al) have been determined by in situ PXRD. The in situ PXRD confirms the retention of the structure of NOTT-300 (Al) upon inclusion and subsequent removal of $SO_2$ (FIG. 5a), thereby confirming the high stability of NOTT-300 (Al) in the presence of corrosive $SO_2$.

Figure 5B:
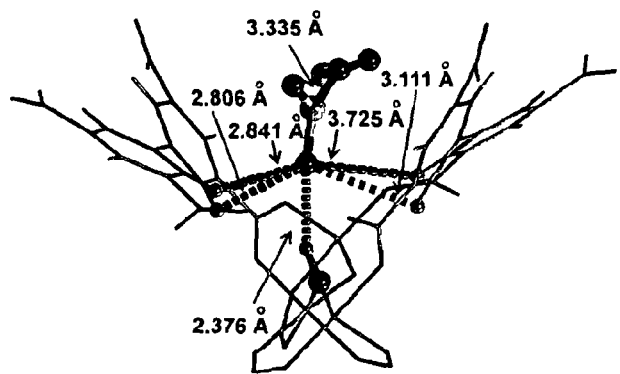
Figure 5C:
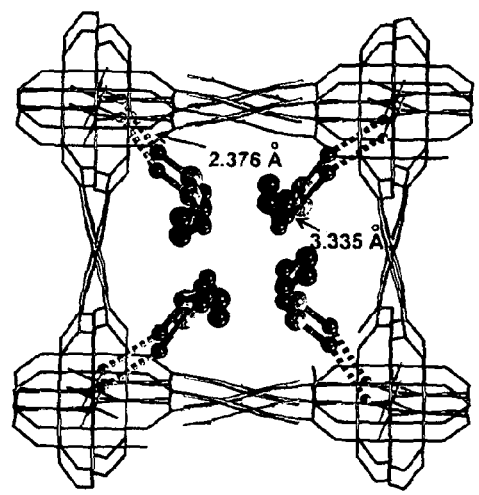

Indeed, the uptake of $SO_2$ in NOTT-300 (Al) is entirely reversible with no apparent loss of capacity on recycling. For NOTT-300 (Al).4$SO_2$ (at 1.0 bar), two distinct, equally-occupied binding sites (I and II) were located within the channel (FIG. 5b): $SO_2$(I) occupies the same position as $CO_2$ and interacts with —OH groups via its O($\delta$–) charged centre [OSO . . . HOAl=2.376(13) Å], which also forms weak interactions with four —CH groups from neighbouring benzene rings [OSO . . . HC=2.806(14), 2.841(17), 3.111(16), 3.725(18) Å]. Thus, as for $CO_2$, a total of five cooperative hydrogen bonds accommodate $SO_2$(I) in a "pocket-like" cavity. A second site, identified as $SO_2$(II), was observed between two $SO_2$(I) molecules. However, no hydrogen bonding between the $SO_2$(II) and —OH or —CH groups are apparent; rather, the O($\delta$–) centre of $SO_2$(II) interacts with the S($\delta$+) charge centre of $SO_2$(I), thus stabilising an $SO_2$(I,II) intermolecular chain via O($\delta$–) . . . S($\delta$+) dipole interactions [O(I) . . . S(II)=3.34(7) Å](FIG. 5b) within the channel. The S=O bond distances for $SO_2$(I) and $SO_2$(II) are 1.481(4) and 1.500(8) Å, respectively, with corresponding <O=S=O angles of 117.5(11) and 109.1(9)°. The structural investigation of NOTT-300 (Al).4$SO_2$ represents a distinct crystallographic study of a $SO_2$-loaded MOF and gives important insights into the $SO_2$ adsorption mechanism.

Figure 6A:
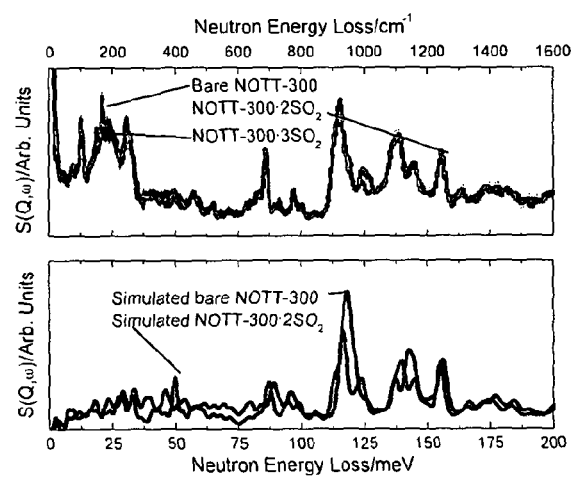
FIGS. 6($a$)-6($c$) show in situ inelastic neutron scattering (INS) spectra and simulated $SO_2$ positions in the pore channel of NOTT-300 (Al)
Figure 6B:
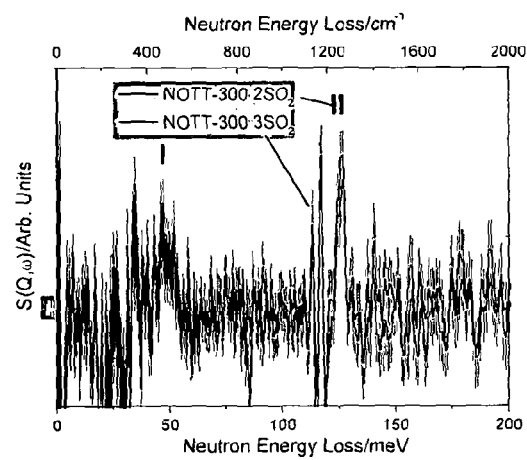
Figure 6C:
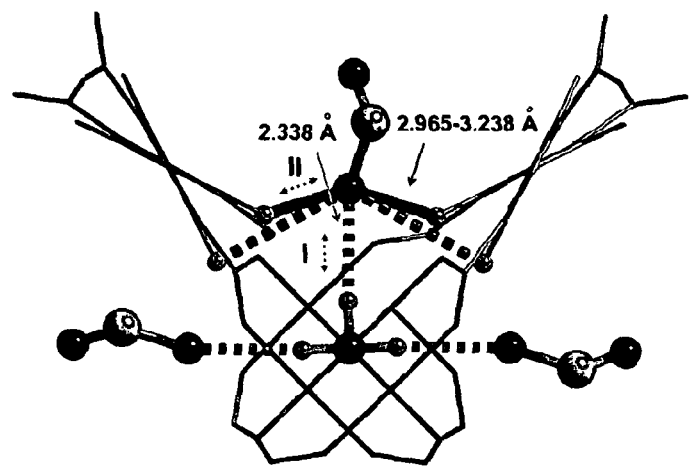
Figure 7:
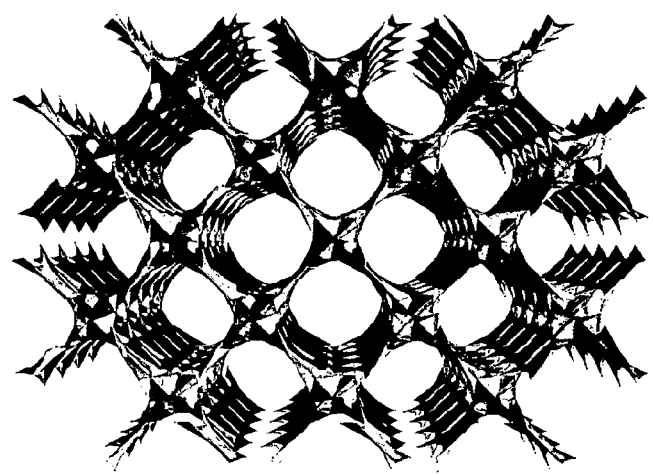
FIG. 7 is a three dimensional representation of the pore structure of a MOF according to an embodiment of the invention.
Figure 8:
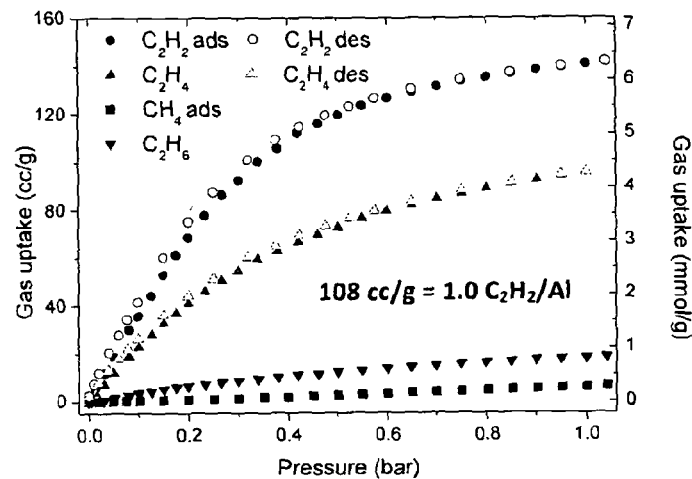
FIG. 8 is a graph comparing the gas adsorption isotherms of various hydrocarbons with NOTT-300 (Al). The corresponding desorption isotherms exhibit full reversibility without hysteresis demonstrating the stability of the MOF in the hydrocarbon environments.
Figure 9:
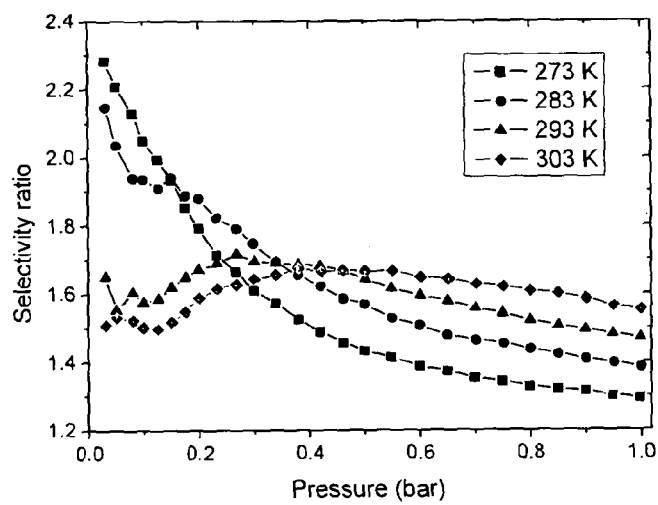
FIG. 9 shows graphs of the gas selectivity ratio for $C_2H_2/C_2H_4$ with NOTT-300 (Al) as a function of gas pressure at various temperatures. Also see Table A provides derived values of extreme selectivity ratios for $C_2H_2/C_2H_4$ at 0 mbar.
Figure 10:
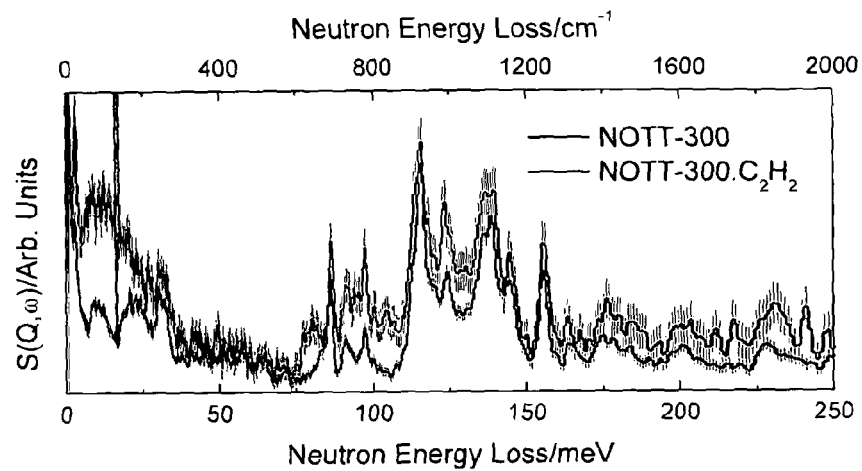
FIGS. 10(a)-10(d) show INS spectra for adsorbed $C_2H_2$ and $C_2H_4$ in NOTT-300(Al).
Figure 10:
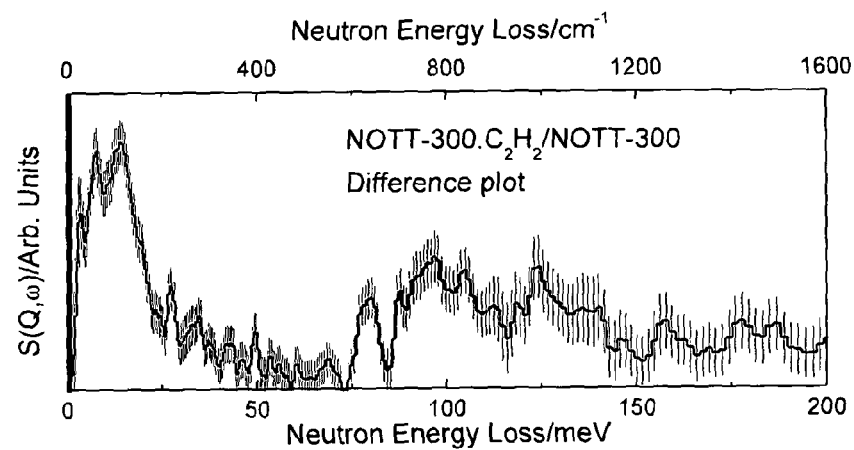
Figure 10:
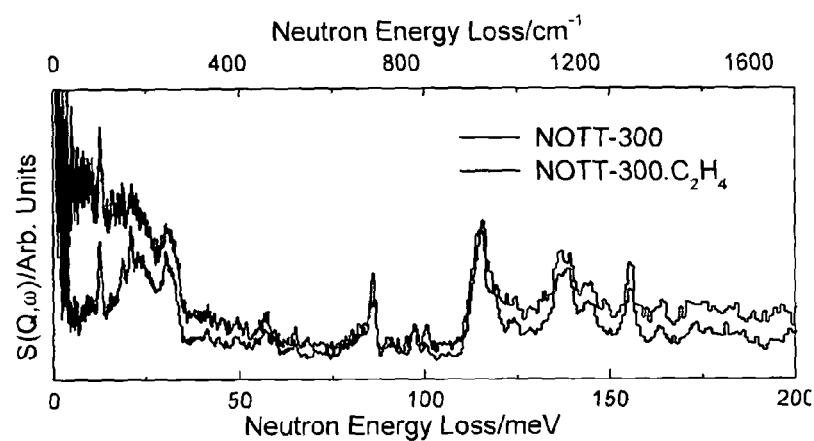
Figure 10:
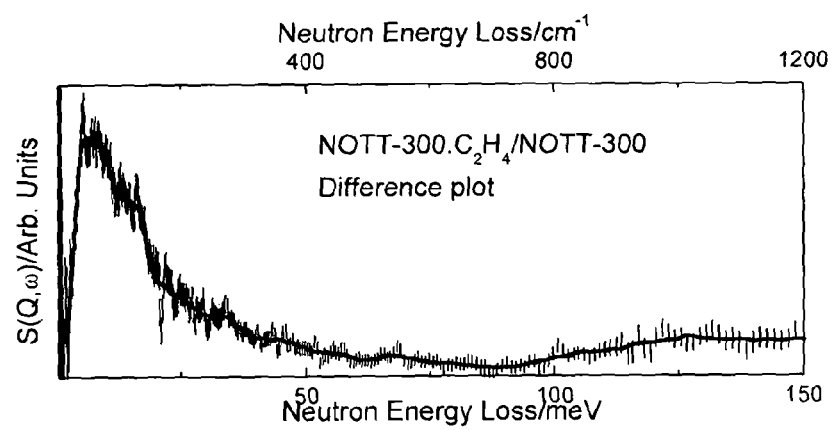
Figure 11:
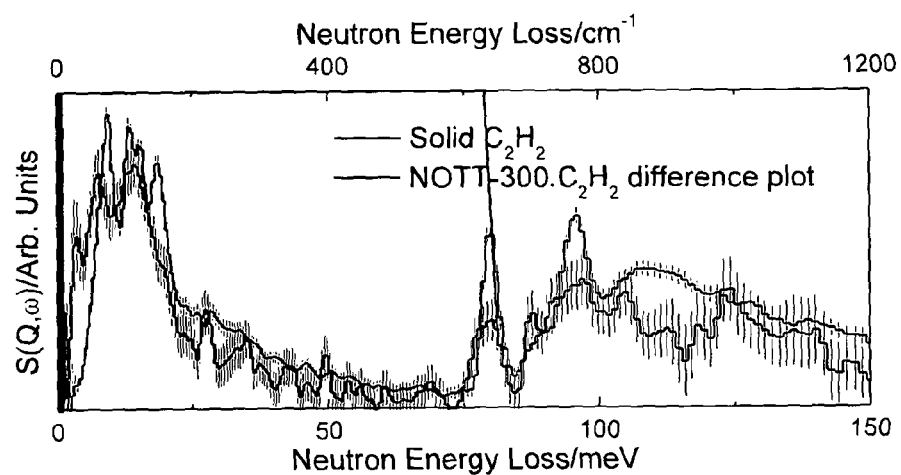
FIGS. 11(a)-11(b) show INS spectra for condensed phase $C_2H_2$.
Figure 11:
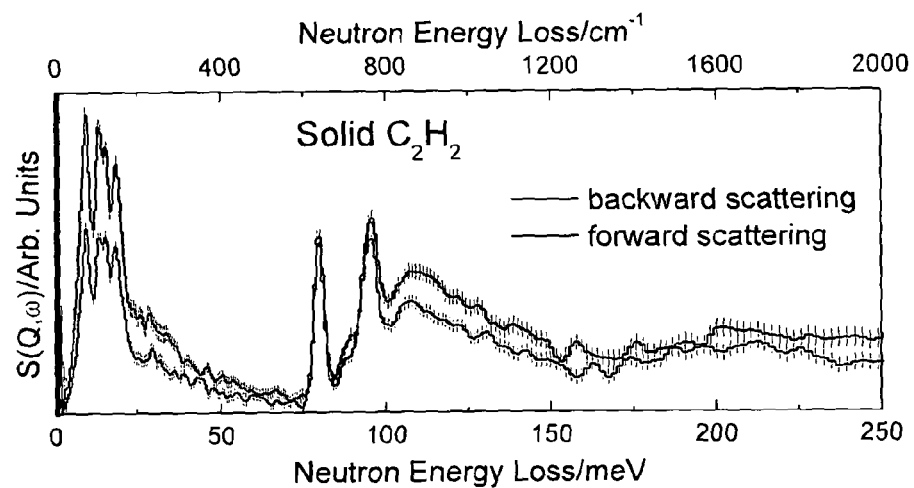
Figure 12:
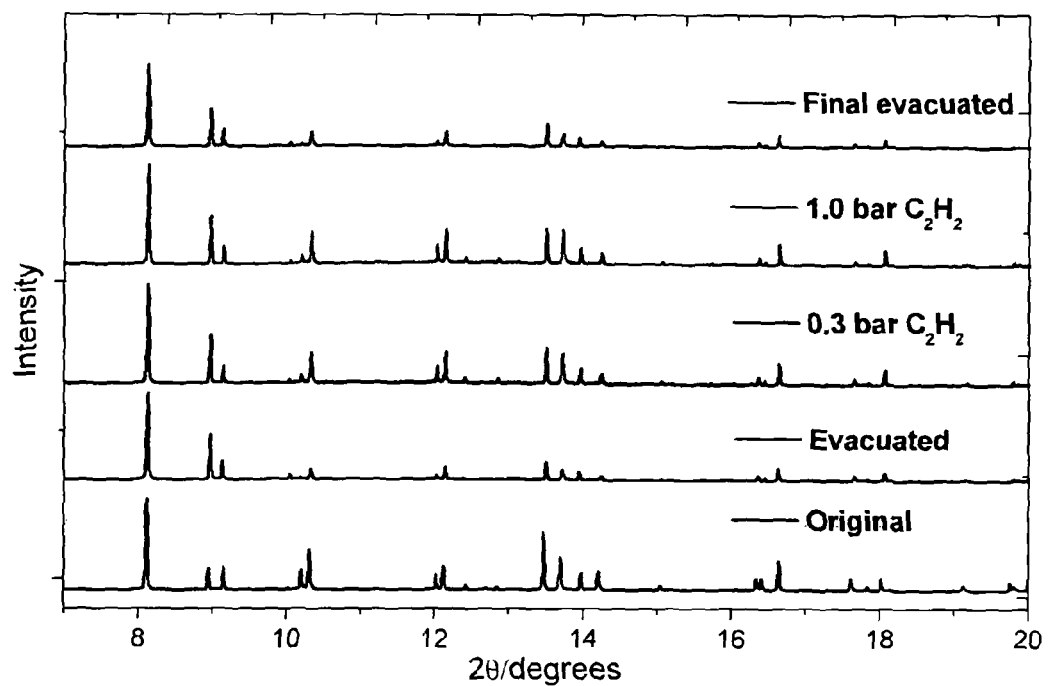
FIG. 12 shows in situ diamond powder diffraction patterns for $C_2H_2$-loaded NOTT-300.
Figure 13A:
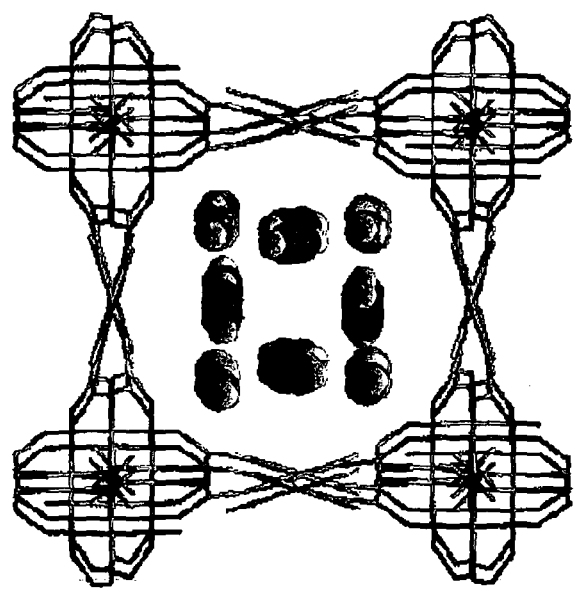
FIGS. 13(a)-13(b) show an illustration of the structure of NOTT-300 (Al).3$C_2H_2$.
Figure 13B:
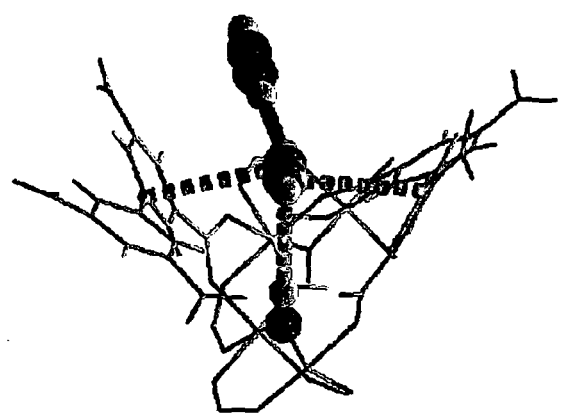
Figure 14A:
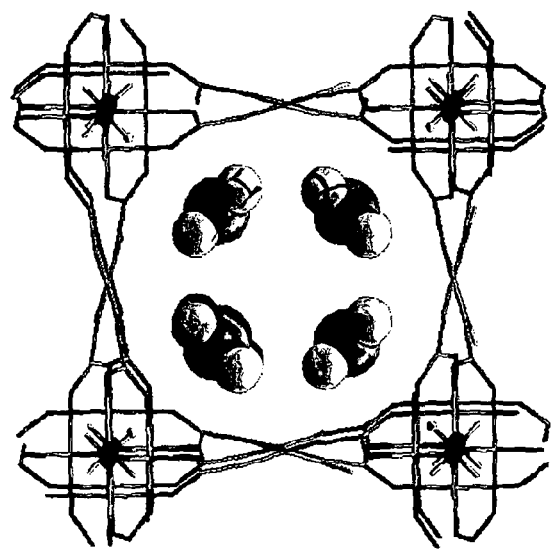
FIGS. 14(a)-14(b) show an illustration of the structure of NOTT-300 (Al).1$C_2H_4$.
Figure 14B:
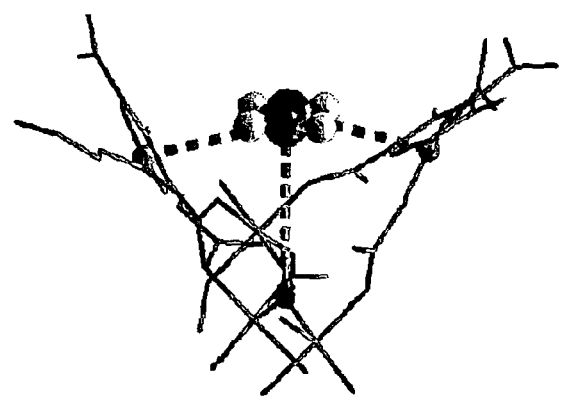
Figure 15A:
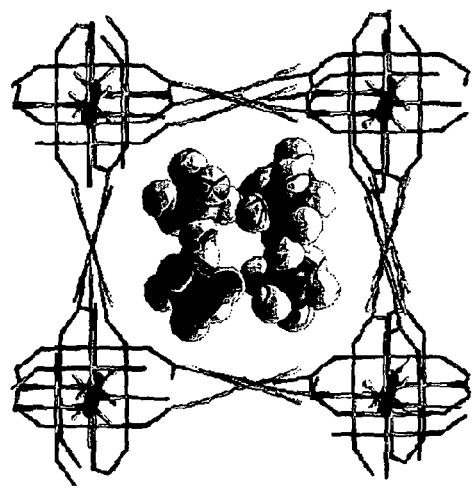
FIGS. 15(a)-15(b) show an illustration of the structure of NOTT-300 (Al).1$C_2H_6$.
Figure 15B:
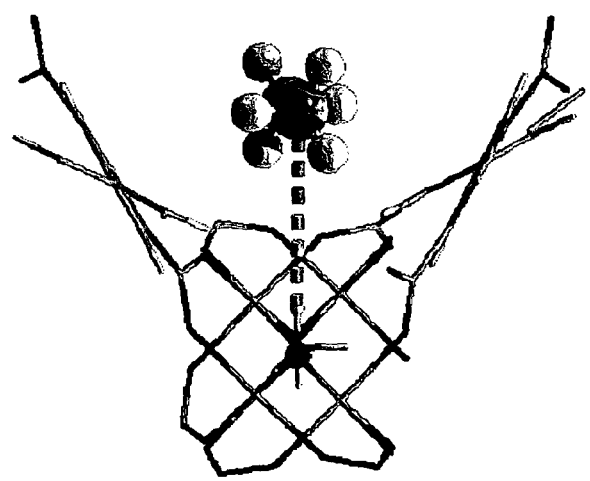
Figure 16:
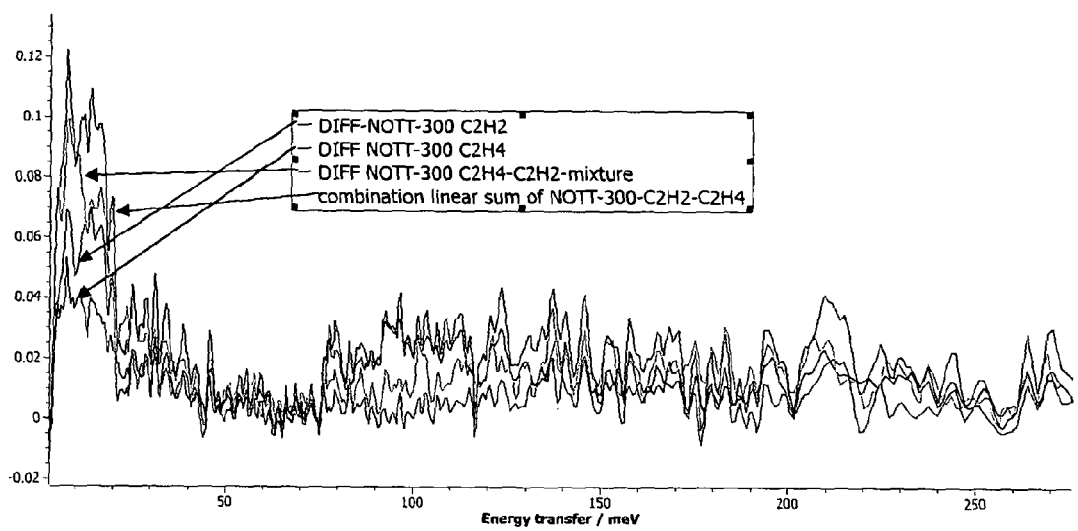
FIG. 16 illustrates INS spectra for $C_2H_{2,4}$.
Figure 17:
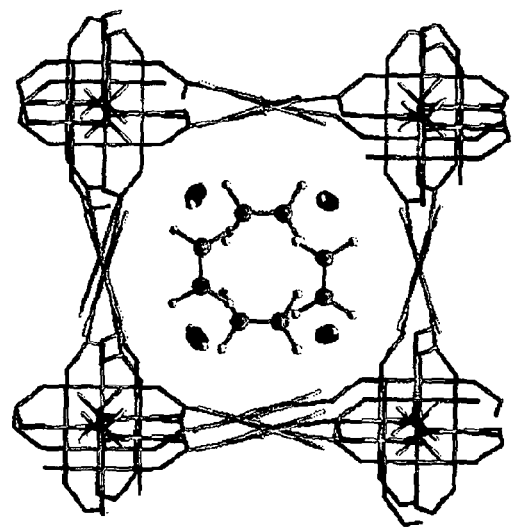
FIG. 17 is an illustration of the structure of NOTT-300 (Al).2.4$C_2H_2$.0.7$C_2H_4$.
Figure 17:
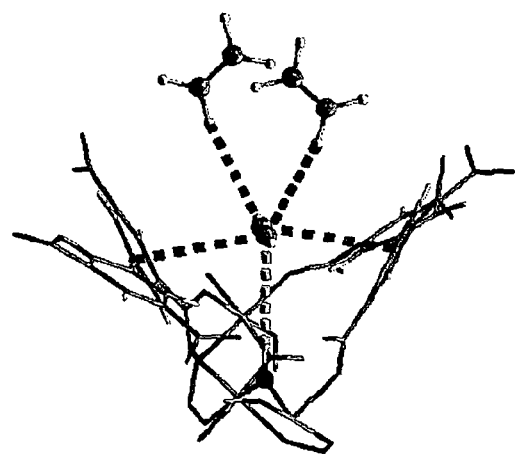
Figure 18:
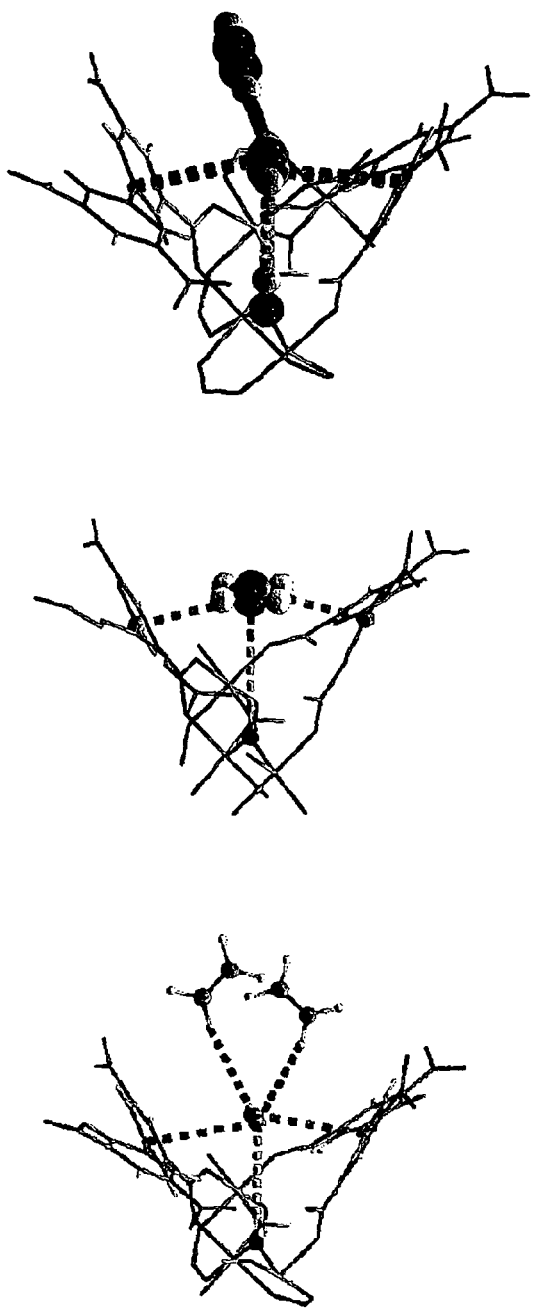
FIG. 18 is an illustration of some structures of NOTT-300 (Al) with adsorbed acetylene and/or ethylene.
Figure 19:
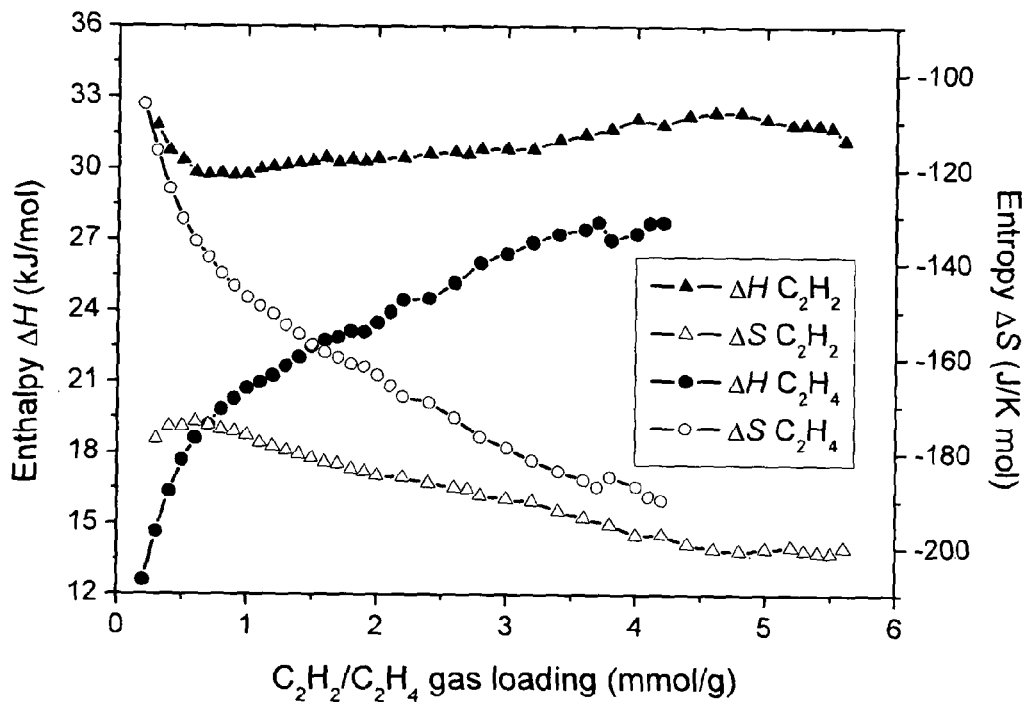
FIG. 19 provides graphs of enthalpy and entropy versus gas pressure for the adsorption of $C_2H_2$ and $C_2H_4$.
Figure 20:
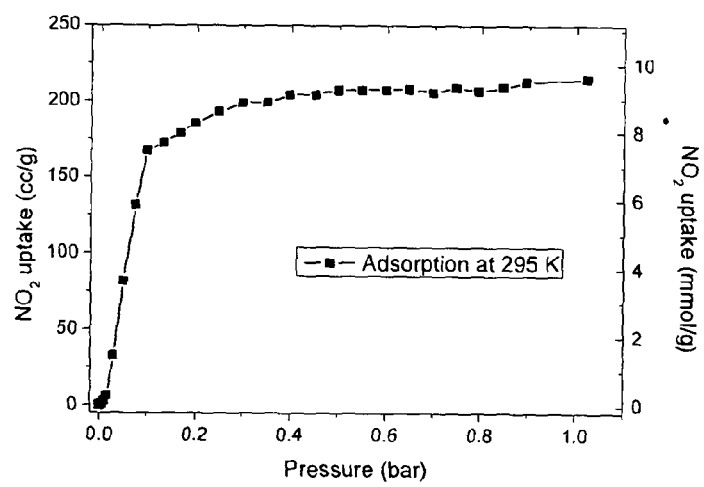
FIG. 20 illustrates a gas adsorption isotherm of $NO_2$ with NOTT-300 (Al) at 295K.
Figure 21A:
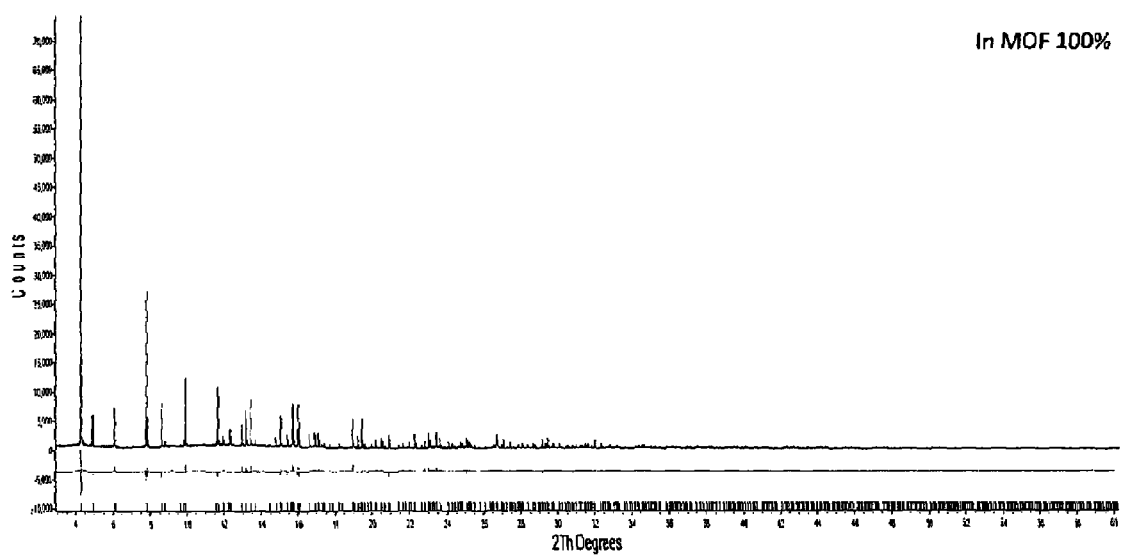
FIGS. 21(a)-21(c) illustrate X-ray diffraction data for NOTT-300 (In).
Figure 21B:
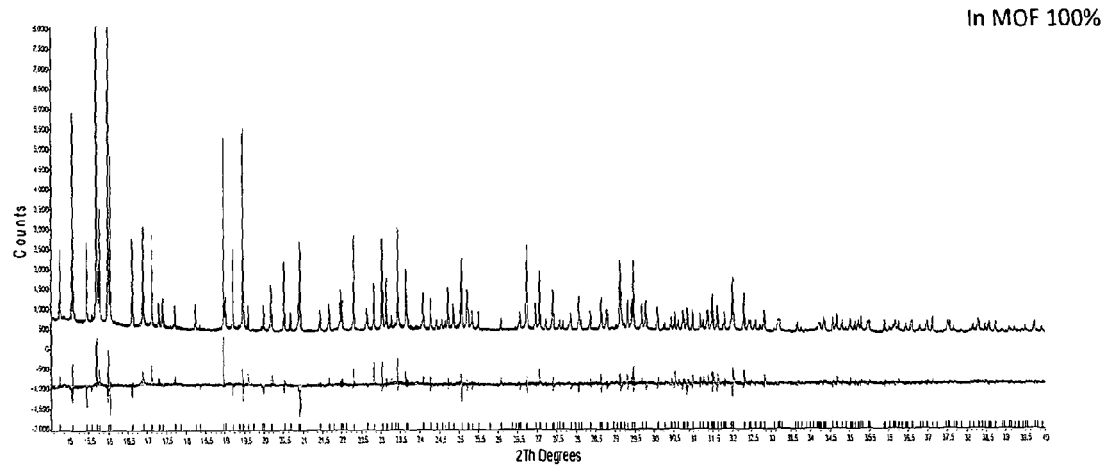
Figure 21C:
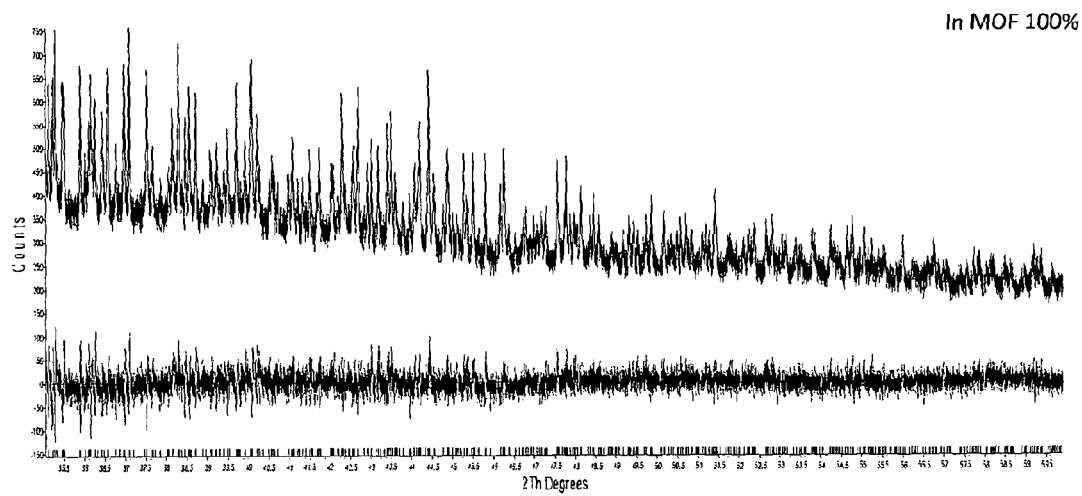
Figure 22A:
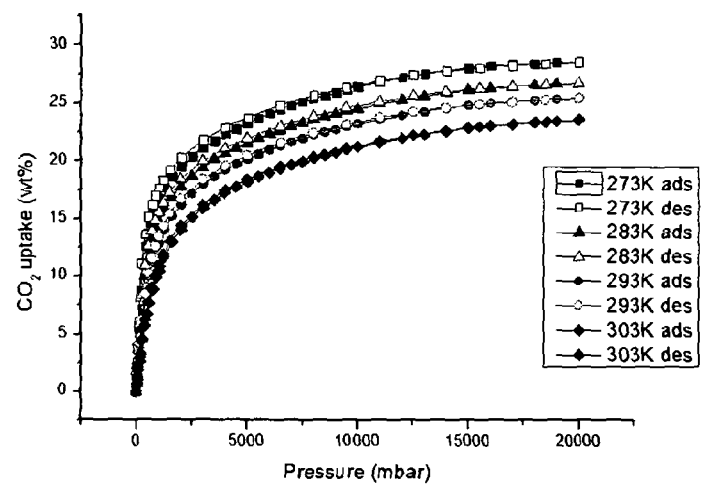
FIG. 22(a) illustrates the gas adsorption isotherms of NOTT-300 (Cr) for $CO_2$ at various temperatures. It can be seen that there is a high uptake of $CO_2$.
Figure 22B:
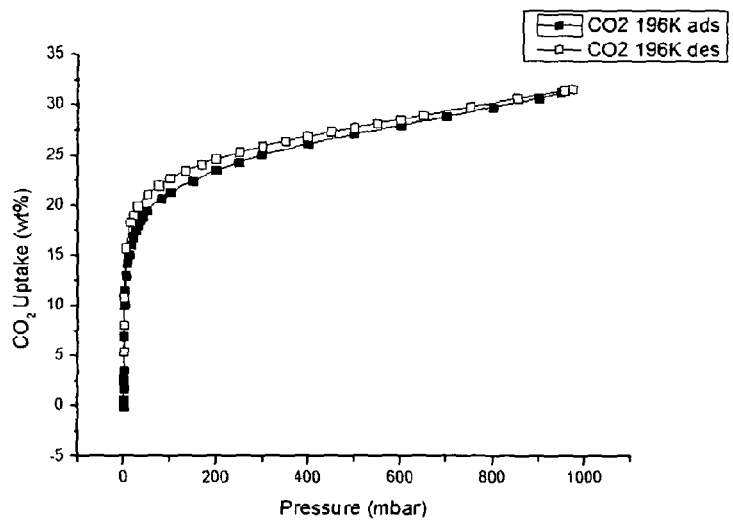
FIG. 22(b) shows the $CO_2$ gas adsorption isotherm for NOTT-300 (Cr) at 198K to more clearly show a high degree of hysteresis between adsorption and desorption thereby indicating the stability of the complex in carbon dioxide gas.
Figure 22C:
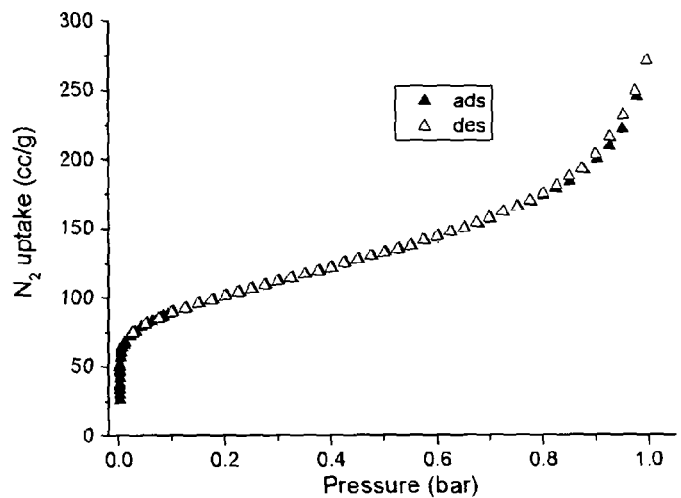
FIG. 22(c) shows the $N_2$ gas adsorption isotherm for NOTT-300 (Cr). It can be seen that the uptake of $N_2$ here is higher than for NOTT-300 (Al)
Figure 22D:
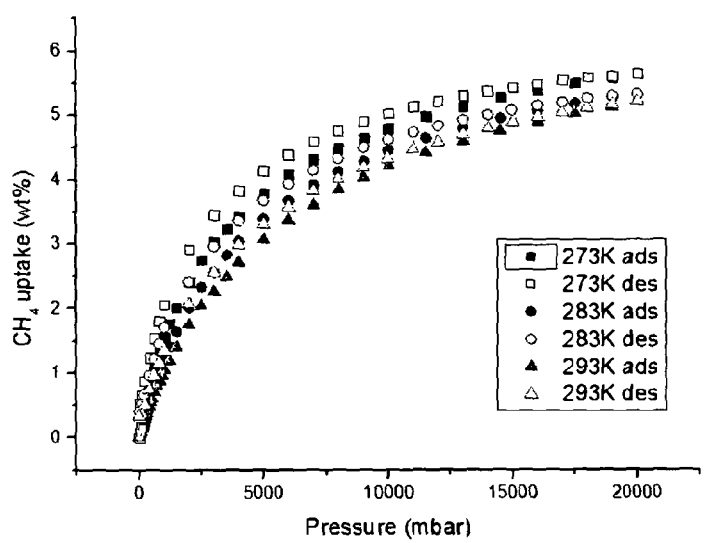
FIG. 22(d) shows the $CH_4$ gas adsorption isotherm for NOTT-300 (Cr)
Figure 22E:
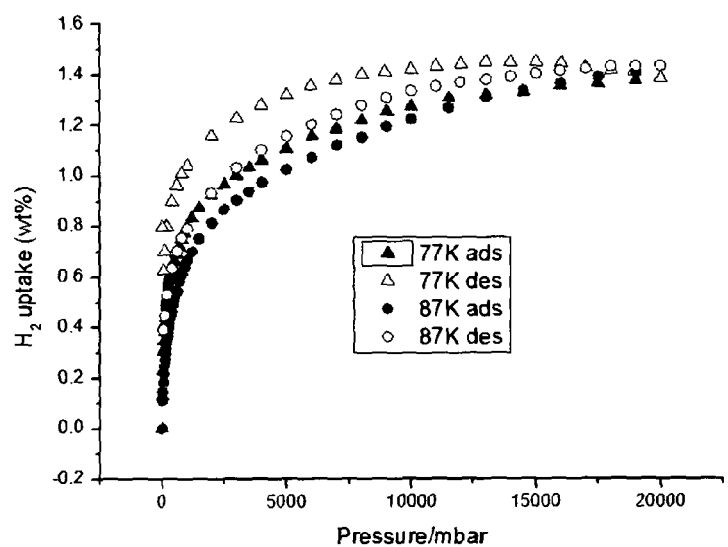
FIG. 22(e) shows the $H_2$ gas adsorption isotherm for NOTT-300 (Cr). It can be seen that the uptake of these gases is very low compared to $CO_2$ and $SO_2$. All the isotherms show good hysteresis of between adsorption and desorption of the gases demonstrating the stability of the compound in the gases.
Figure 23:
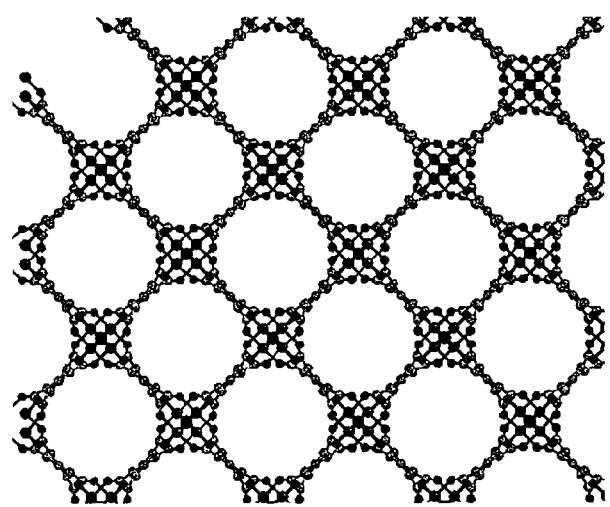
FIG. 23 is a packing diagram for NOTT-300 (Cr) illustrating that this MOF is isostructural with NOTT-300 (Al) with 1-dimensional square pore channels.
Figure 24:
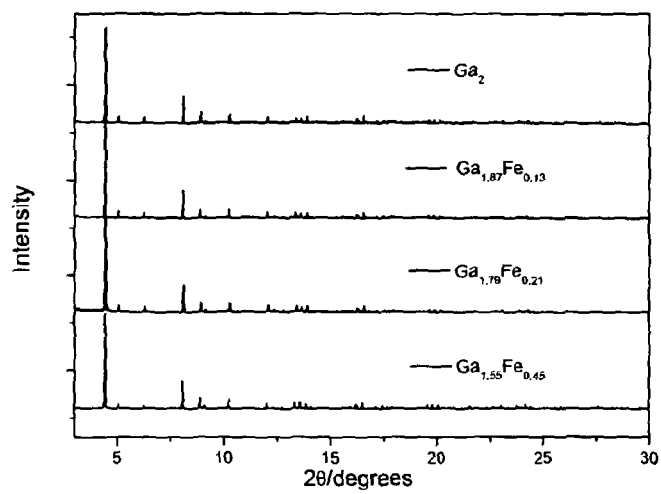
FIG. 24 illustrates the powder X-ray diffraction data (PXRD) patterns for $(Ga_{2-x}Fe_x)MOF(x=0, 0.13, 0.21, 0.45)$. The patterns confirm that the parent MOF NOTT-300 (Ga)-solvated is iso-structural to NOTT-300(Al)-solvated.
Figure 25:
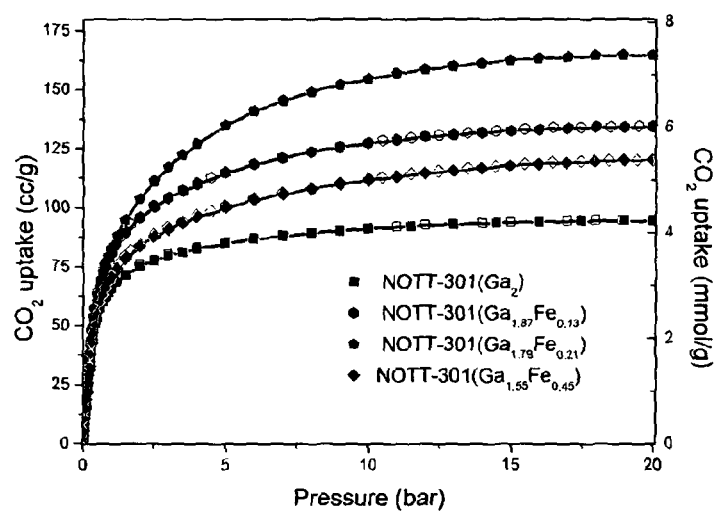
FIG. 25 shows the $CO_2$ adsorption isotherms for NOTT3-00($Ga_{2-x}Fe_x$) (x=0, 0.13, 0.21, 0.45) at 195 K at pressures up to 1 bar. It can be seen that the degree of $CO_2$ uptake is dependent on the molar ratio of Ga and Fe used in the MOF.
Figure 26:
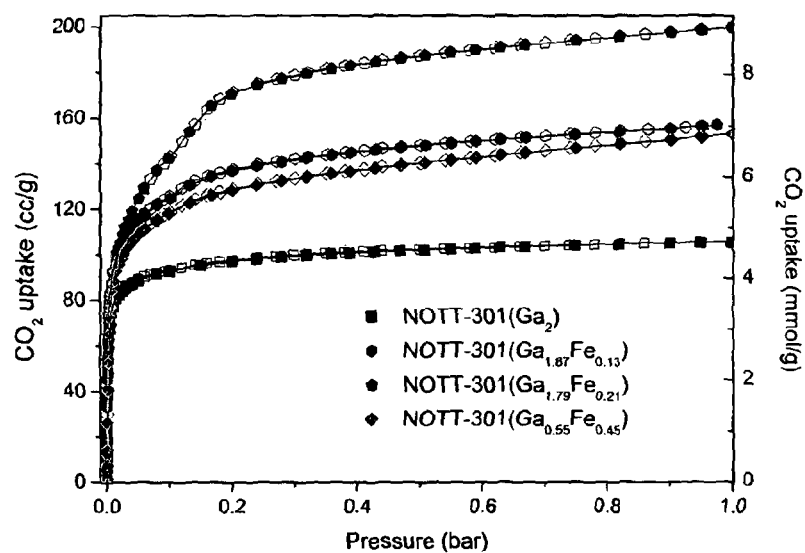
FIG. 26 shows the $CO_2$ adsorption isotherms for NOTT-300($Ga_{2-x}Fe_x$) (x=0, 0.13, 0.21, 0.45) at 293 K at pressures up to 20 bar.

Despite the small total bound scattering cross section of sulphur (1.026 barns), comparison of the INS spectra below 5 K reveals two major increases in peak intensity on going from bare NOTT-300 (Al) to NOTT-300 (Al).2$SO_2$ (or NOTT-300 (Al).3$SO_2$): peak I occurs at low energy transfer (30-50 meV) and peak II at high energy transfer (125 meV), similar to that observed in the INS spectra for $CO_2$-loaded NOTT-300 (Al) (FIG. 6b). Moreover, immediate stiffening of the motion of the NOTT-300 (Al) host was observed upon $SO_2$ inclusion, as evidenced by the slight shift in INS peak to higher energies in NOTT-300 (Al).2$SO_2$ and NOTT-300 (Al).3$SO_2$ (FIG. 6a). DFT simulation has also been performed to optimise the structures of both NOTT-300 (Al) and NOTT-300 (Al).2$SO_2$ materials. The simulated INS spectra show good agreement with the experimental spectra and are consistent with the adsorbed $SO_2$ molecules interacting end-on to the hydroxyl groups via the hydrogen bond interactions [O . . . H=2.338 Å] with additional supramolecular contacts with the adjacent aromatic C—H groups [O . . . H=2.965-3.238 Å] (FIG. 6c). The INS/DFT results are entirely consistent with the PXRD analysis and provide key insights into the dynamics of the NOTT-300 (Al) host upon $SO_2$ inclusion.

Selective Hydrocarbon Uptake of NOTT-300 (Al)

TABLE A

| Selectivity | 273K | 283K | 293K | 303K |
|---|---|---|---|---|
| $C_2H_2/C_2H_4$ | 4.20 | 2.52 | 2.06 | 1.56 |

Structure Determination and Refinement for NOTT-300 (Al)-Solvate, NOTT-300 (Al).3.2$CO_2$ and NOTT-300 (Al).4$SO_2$ High resolution powder diffraction data were collected on Beamline I11 at Diamond Light Source by using multi-analysing-crystal detectors (MACs)[28] and an in-situ gas cell system. The powder pattern was firstly indexed on a body-centred tetragonal lattice and the independent unit cell parameters were refined using TOPAS.[29] The body centring and the reflection condition 00l:l=4n indicates that the space group is one of the enantiomeric pair $I4_1 22$ and $I4_3 22$. In the absence of any component capable of directing chirality, the product is expected to be a 1:1 racemic mixture. The structure solution was initially established in space group $I4_1 22$ by charge flipping using the program Superflip,[30] and further developed from subsequent difference Fourier analysis using TOPAS. The final structure refinement was carried out using the Rietveld method[29] with isotropic displacement parameters for all atoms. A total of 40 disordered water molecules per unit cell were found within the pore channel and included in the final structure refinement for NOTT-300 (Al)-solvate. Upon desolvation and $SO_2$ loading, we observe neither major changes to cell parameters nor extra features in the patterns, suggesting that there is no structural phase change during the experiment. However, upon $SO_2$ loading, there are significant increases in the peak intensities at ~6.2, 10.2, 12 and 14° 2θ, indicating that the $SO_2$ molecules are adsorbed into the material, and that the overall microscopic ordering of the $SO_2$/host system is increasing. A Monte-Carlo-based simulated annealing technique in which the guest $SO_2$ molecules were treated as rigid bodies was used to locate their positions in NOTT-300 (Al).4$SO_2$. Two independent $SO_2$ sites were found each with half occupancy. The $SO_2$ content was refined giving a stoichiometry of 1.98(2) molecules of $SO_2$ per Al, slightly higher than the experimental value of 1.7 $SO_2$ per Al. The occupancy of the first $CO_2$ site was determined to be 0.865(9) and the second $CO_2$ site 0.727(7), leading to a total refined $CO_2$ stoichiometry of 1.592(12) in excellent agreement with the experimental value of 1.6 $CO_2$ per Al. The final stage of the Rietveld refinement involved soft restraints to the C—C bond lengths within the benzene rings. Rigid body refinement was applied to the $CO_2$ and $SO_2$ molecules in the pore.

Crystal Data for NOTT-300 (Al)-Solvate

[$Al_2(OH)_2(C_{16}H_6O)$]($H_2O$)$_6$. White powder. Tetragonal, space group $I4_1 22$, a=b=14.82958(6), c=11.77317(5) Å, V=2589.11(3) Å$^3$, M=522.29, T=293(2) K, Z=4. The final Rietveld plot corresponds to satisfactory crystal structure model ($R_{Bragg}$=0.056) and profile ($R_p$=0.052 and $R_{wp}$=0.072) indicators with a goodness-of-fit parameter of 1.345. Final fractional coordinates for NOTT-300 (Al)-solvate are listed in Table S1.

TABLE S1

Atomic positions for non-hydrogen atoms in NOTT-300 (Al)-solvate

|  | x | y | z | $B_{iso}$ (Å$^2$) |
|---|---|---|---|---|
| Al1 | 0.69426(5) | 0.30574(5) | 0.5 | 0.72(13) |
| O1 | 0.75744(13) | 0.25 | 0.625 | 0.51(12) |
| O2 | 0.89782(9) | 0.28675(9) | 0.99869(15) | 0.51(12) |
| O3 | 0.62165(10) | 0.37371(10) | 0.39436(12) | 0.51(12) |
| C1 | 0.59280(35) | 0.36039(14) | 0.69453(19) | 0.70(13) |
| C2 | 0.54498(10) | 0.43181(7) | 0.75722(10) | 0.70(13) |
| C3 | 0.5 | 0.5 | 0.69649(14) | 0.70(13) |
| C4 | 0.54071(10) | 0.428618(71) | 0.87716(8) | 0.70(13) |
| C5 | 0.5 | 0.5 | 0.93474(11) | 0.70(13) |
| O1w | 0.91080(23) | 0.80489(16) | 0.94077(28) | 21.6(2) |
| O2w | 0.45734(19) | 0.73953(30) | 0.06123(32) | 11.9(3) |
| O3w | 0.13041(22) | 0.29586(24) | 0.53782(37) | 35.7(3) |

Crystal Data for NOTT-300 (Al).3.2$CO_2$

[$Al_2(OH)_2(C_{16}H_6O_8)$]($CO_2$)$_{3.2}$. White powder. Tetragonal, space group $I4_1 22$, a=b=14.82432(6), c=11.80570(5)Å, V=2594.43(3) Å$^3$, M=550.03, T=273(2) K, Z=4. The final Rietveld plot corresponds to satisfactory crystal structure model ($R_{Bragg}$=0.025) and profile ($R_p$=0.043 and $R_{wp}$=0.059) indicators with a goodness-of-fit parameter of 1.531. Final fractional coordinates for NOTT-300 (Al)·3.2CO$_2$ are listed in Table S2.

TABLE S2

Atomic positions for NOTT-300 (Al)·3.2CO$_2$

| | X | y | z | B$_{iso}$ (Å$^2$) |
|---|---|---|---|---|
| Al1 | 0.30694(4) | −0.30694(4) | 0.5 | 0.93(40) |
| O1 | 0.75117(13) | 0.25 | 6.625 | 0.82(40) |
| H1 | 0.8123(17) | 0.25 | 0.625 | 0.75(40) |
| O2 | 0.62152(22) | 0.37975(22) | 0.60276(28) | 0.82(40) |
| O3 | 0.60511(22) | 0.28380(22) | 0.75032(28) | 0.82(40) |
| C1 | 0.59215(19) | 0.36044(15) | 0.70222(15) | 1.37(40) |
| C2 | 0.54078(8) | 0.43003(6) | 0.76456(13) | 1.37(40) |
| C3 | 0.5 | 0.5 | 0.70584(14) | 1.37(40) |
| H3 | 0.5 | 0.5 | 0.6125(7) | 1.37(40) |
| C4 | 0.54078(8) | 0.43003(6) | 0.88199(13) | 1.37(40) |
| H4 | 0.5675(4) | 0.3842(6) | 0.9205(6) | 1.37(40) |
| C5 | 0.5 | 0.5 | 0.94071(14) | 1.37(40) |
| C1_1 | 1.0335(25) | 0.25 | 0.6676(12) | 15.1(2) |
| O1_1 | 0.9673(23) | 0.25 | 0.625 | 18.7(5) |
| O2_1 | 1.0998(22) | 0.25 | 0.7102(24) | 39.4(8) |
| C1_2 | 0.25 | 0.35535 | 0.375 | 18.3(2) |
| O1_2 | 0.32821 | 0.35535 | 0.375 | 38.4(8) |

Crystal Data for NOTT-300 (Al)·4SO$_2$

[Al$_2$(OH)$_2$(C$_{16}$H$_6$O$_8$)](SO$_2$)$_4$. White powder. Tetragonal, space group I4$_1$22, a=b=14.84740(10), c=11.80564(8)Å, V=2602.50(4) Å$^3$, M=670.46, T=273(2) K, Z=4. The final Rietveld plot corresponds to satisfactory crystal structure model (R$_{Bragg}$=0.024) and profile (R$_p$=0.044 and R$_{wp}$=0.057) indicators with a goodness-of-fit parameter of 1.293. Final fractional coordinates for NOTT-300 (Al)·4SO$_2$ are listed in Table S3.

TABLE S3

Atomic positions for NOTT-300 (Al)·4SO$_2$

| | X | y | z | B$_{iso}$ (Å$^2$) |
|---|---|---|---|---|
| Al1 | 0.30668(4) | −0.30668(4) | 0.5 | 0.83(11) |
| O1 | 0.75093(11) | 0.25 | 0.625 | 0.50(11) |
| H1 | 0.8094(7) | 0.2737(13) | 0.6182(19) | 0.75(17) |
| O2 | 0.87680(8) | 0.12169(8) | 0.10281(9) | 0.50(11) |
| O3 | 0.89634(7) | 0.21365(7) | 0.25360(13) | 0.50(11) |
| C1 | 0.85735(12) | 0.09466(13) | 0.79858(16) | 0.90(12) |
| C2 | 0.53958(11) | 0.43084(7) | 0.75958(9) | 0.90(12) |
| C3 | 0.5 | 0.5 | 0.69441(10) | 0.90(12) |
| H3 | 0.5 | 0.5 | 0.6125(7) | 1.09(14) |
| C4 | 0.54005(7) | 0.42960(5) | 0.87811(9) | 0.90(12) |
| H4 | 0.57318 | 0.38162 | 0.90735 | 1.09(14) |
| C5 | 0.5 | 0.5 | 0.93693(9) | 0.90(12) |
| S1 | 0.062518 | 0.257889 | −0.415951 | 15.1(2) |
| O1s | −0.036130 | 0.243180 | −0.416293 | 5.8(2) |
| O2s | 0.110299 | 0.250886 | −0.525706 | 39.4(8) |
| S2 | 0.103150 | 0.184862 | −0.037573 | 18.3(2) |
| O3s | 0.117697 | 0.239213 | −0.143103 | 38.4(8) |
| O4s | 0.123069 | 0.242537 | 0.063692 | 24.4(4) |

A detailed description has been given above for an aluminium hydroxyl metal organic framework complex. Analogues to this complex have also been synthesised based on indium, antimony, chromium and gallium. A metal organic framework has also be synthesised that contains both aluminium and iron functional groups. These analogue complexes also exhibit the same high uptake and selectivity for XO$_2$ gases (X=C, S, O).

Transmission Electron Microscopic (TEM) Study on NOTT-300 (Al).

A TEM image shows the crystals to have uniform morphology of ~1 m plates (Fig. S7a,b), and a high resolution (HRTEM) image confirms the presence of extended crystalline planes (Fig. S7c).

Synchrotron Powder Diffraction Studies of Solvated NOTT-300

Figure 43:
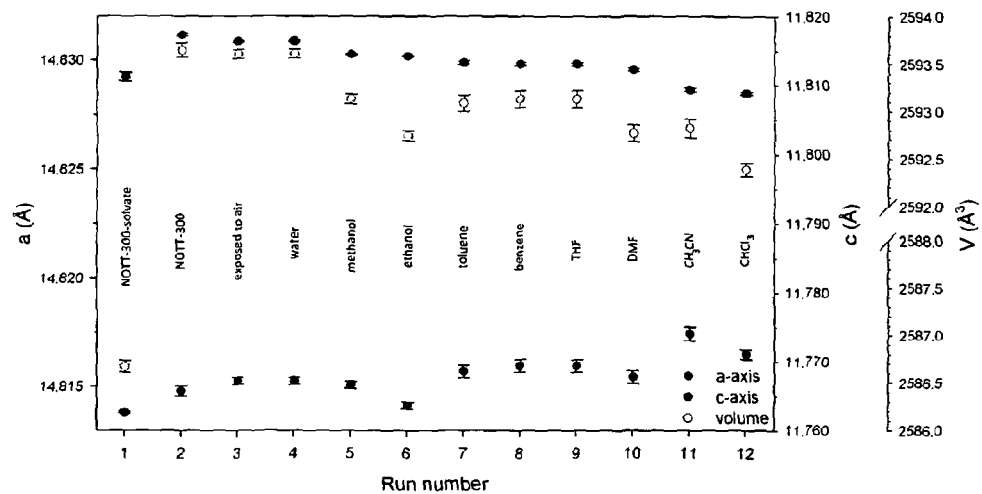
FIG. 43 shows graphs comparing of unit cell parameters of NOTT-300(Al) under different chemical environments.

To investigate the chemical stability of desolvated NOTT-300, an important feature for a capture material, PXRD patterns were collected for a range of NOTT-300 samples under variable chemical environments. Some of these are illustrated in FIG. 42. After the collection of an original pattern for the as-synthesised sample, NOTT-300 solvate was degassed at 150° C. to generate desolvated NOTT-300. The desolvated material was then separated into ten portions, each of which was exposed to air for one month, or immersed in water, methanol, ethanol, CHCl$_3$, CH$_3$CN, DMF, THF, benzene or toluene for one week. Comparison of the resultant PXRD patterns confirms the excellent stability of the desolvated NOTT-300 material under air, water and common organic solvents. FIG. 43 provides an illustration comparing of unit cell parameters of NOTT-300 under different chemical environments.

Variable Temperature Powder Diffraction of NOTT-300 (Al)

Figure 45:
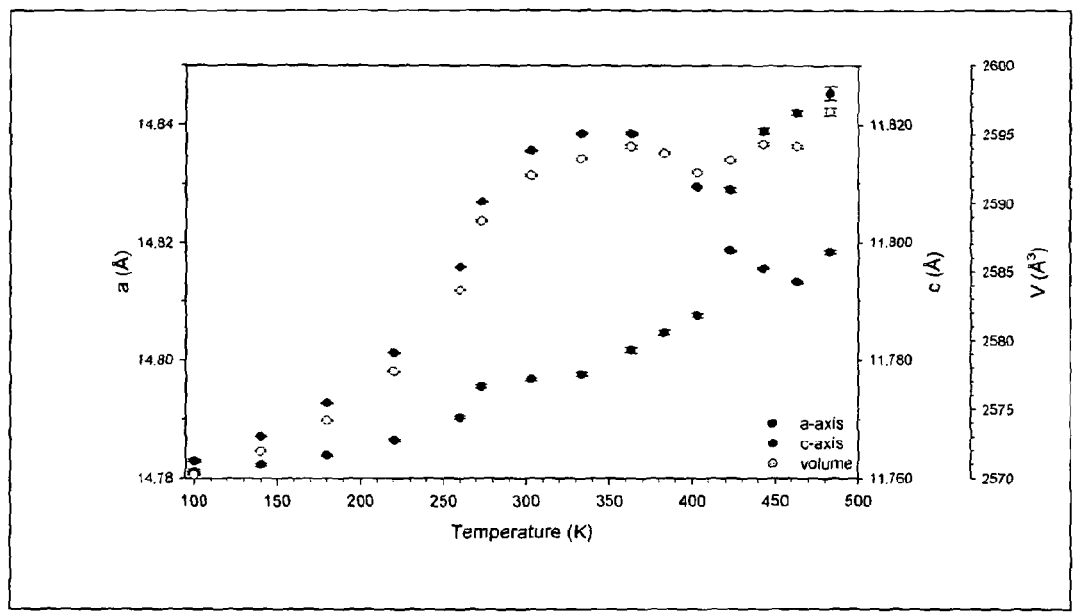
FIG. 45 is a graph comparing of unit cell parameters for NOTT-300(Al)-solvate as a function of temperature.

To investigate the possible framework phase change of NOTT-300 (Al)-solvate as a function of temperature, variable temperature PXRD patterns were collected at 100-483 K for NOTT-300 (Al)-solvate (FIG. 44). Comparison of the PXRD patterns confirms that there is no framework phase transition over this temperature range and the framework of NOTT-300 (Al) remains intact after removal of the water molecules in the channels. The lattice parameters were refined via Le Bail methods, and results are summarised in Table S3. The overall change in the unit cell volume is less than 1.0%, confirming the rigidity of the framework. FIG. 44 provides variable temperature PXRD patterns for NOTT-300 (Al)-solvate (=1.54056 Å). FIG. 45. Unit cell parameters for NOTT-300 (Al)-solvate as a function of temperature.

Table S4 provides a summary of Le Bail refinement results and unit cell parameters for NOTT-300 (Al)-solvate.

TABLE S4

| | a, b (Å) | c (Å) | V (Å$^3$) | Unit cell change (%) |
|---|---|---|---|---|
| 100 K | 14.78200(30) | 11.76100(35) | 2569.87(13) | 0.000 |
| 140 K | 14.78821(29) | 11.76287(33) | 2572.44(12) | 0.100 |
| 180 K | 14.79348(30) | 11.76458(34) | 2574.64(13) | 0.186 |
| 220 K | 14.80187(30) | 11.76717(34) | 2578.13(13) | 0.321 |
| 260 K | 14.81512(30) | 11.77028(35) | 2583.43(13) | 0.527 |
| 273 K | 14.82847(31) | 11.77667(37) | 2589.50(13) | 0.764 |
| 303 K | 14.83686(30) | 11.77726(36) | 2592.56(13) | 0.883 |
| 333 K | 14.83822(31) | 11.77750(38) | 2593.09(14) | 0.904 |
| 363 K | 14.83625(48) | 11.78236(61) | 2593.46(21) | 0.918 |
| 383 K | 14.83288(42) | 11.78464(54) | 2592.79(19) | 0.892 |
| 403 K | 14.82777(38) | 11.78762(47) | 2591.66(17) | 0.848 |
| 423 K | 14.81612(45) | 11.81073(51) | 2592.66(19) | 0.887 |
| 443 K | 14.81299(54) | 11.81873(59) | 2593.32(23) | 0.912 |
| 463 K | 14.81193(51) | 11.82149(60) | 2593.55(22) | 0.921 |
| 483 K | 14.8186(13) | 11.8244(15) | 2596.54(56) | 1.04 |

Exposure of NOTT-300 (Al) to Water.

Figure 53:
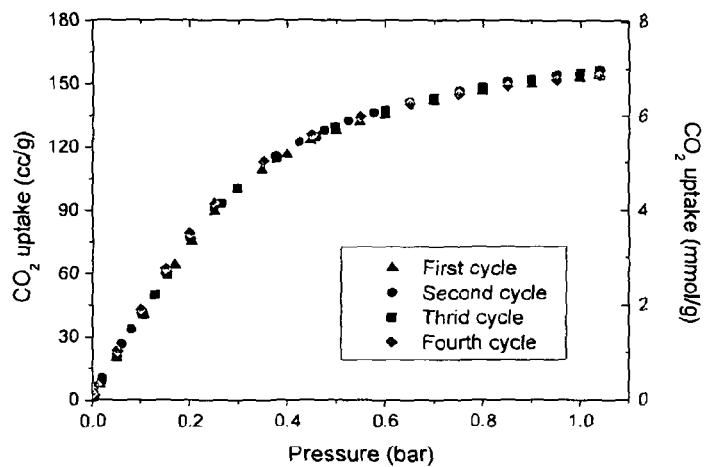
FIG. 53 illustrates CO$_2$ adsorption isotherms at 273 K for NOTT-300(Al) upon cyclic hydration and desolvation process.

The NOTT-300 (Al)-solvate material was loaded into an IGA and degassed at 120° C. and 10$^{-10}$ bar for 24 h to give the fully desolvated NOTT-300 (Al) material. A CO$_2$ adsorption isotherm was then measured at 273 K and up to 1.0 bar (noted as first cycle). The desolvated sample was then exposed to high temperature (90-100° C.) water vapour for 1 h as a humidity treatment. The hydrated sample was then loaded into IGA and degassed again at 120° C. and 10$^{-10}$ bar for 24 h to give desolvated NOTT-300 (Al) material. A second CO$_2$ adsorption isotherm was then measured at 273 K and up to 1.0 bar (noted as the second cycle). The same humidity treatment (hydration), degassing (de-hydration), and $CO_2$ adsorption were repeated twice more (noted as third and fourth cycles). Comparisons of these four $CO_2$ adsorption isotherms confirm that there is no apparent loss of uptake capacity and that the pore surface can be fully regenerated, showing that the framework has good stability upon exposure to the above humidity cycle. FIG. 53 illustrates the $CO_2$ adsorption isotherms at 273 K for NOTT-300 (Al) upon cyclic hydration and desolvation process.

DFT Modelling and Simulations on NOTT-300

The vibrational properties of the NOTT-300 (Al) were calculated using a combination of density functional theory (DFT) and plane-wave pseudopotential methods as implemented in the CASTEP code,[2] using ultra-soft pseudopotentials with a plane-wave energy cutoff of 380 eV. Calculations were performed under the PBE approximation[3] for exchange and correlation. The unit cell used has a volume of 2589.2 Å[3] and contains 144 and 156 atoms for the bare and $CO_2$-loaded materials, respectively. The wave functions were sampled according to the Monkhorst-Pack scheme with a k-points mesh of spacing ~0.05 Å$^{-1}$. The normal modes of the solid were determined from dynamical matrices calculated using finite displacements, by numerical differentiation. The INS spectra was the calculated using the a Climax software.[4]

Figure 29:
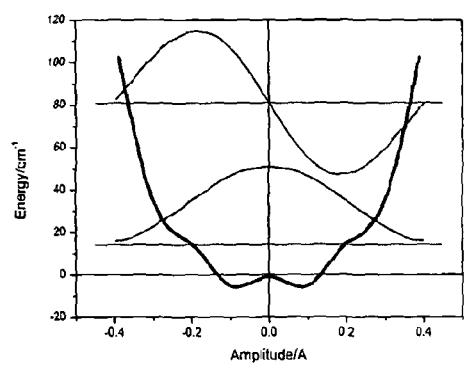
FIG. 29 is a graph showing the potential energy surface along the first vibrational eigenvector of the hydrogen bond between $CO_2$ and an OH group of NOTT-300 (Al)
Figure 30A:
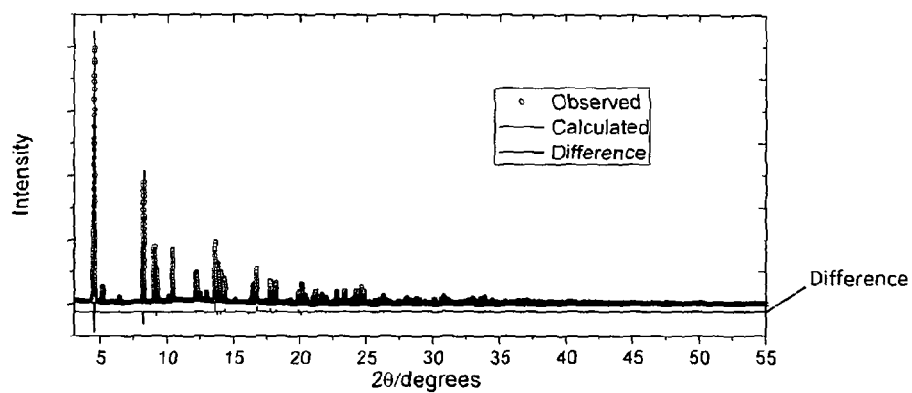
FIG. 30(a) illustrates PXRD patterns for the Rietveld refinement of the as-synthesized NOTT-300 (Al)-solvate [λ=0.826949(2) Å].
Figure 30B:
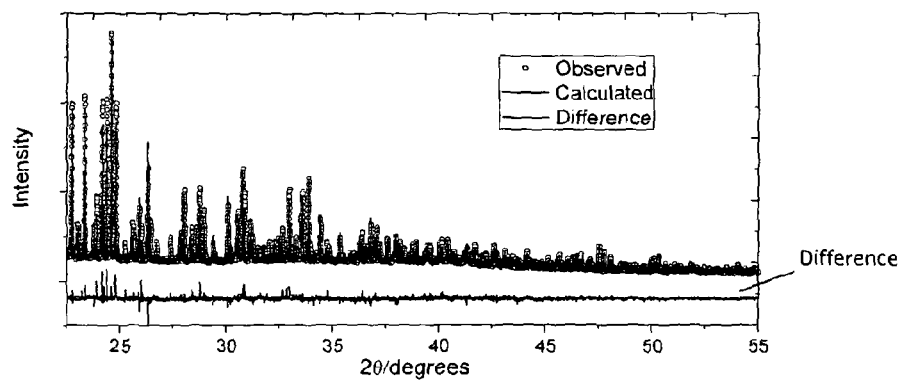
FIG. 30(b) illustrates PXRD patterns for higher angle data (2θ=22.5-55°) scaled up to show the quality of the fit between the observed and the calculated patterns.
Figure 31A:
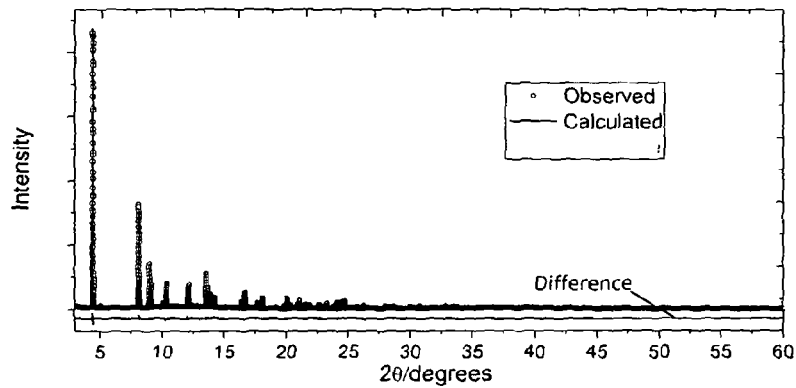
FIG. 31(a) illustrates PXRD patterns for the Rietveld refinement of the $CO_2$-loaded NOTT-300 (Al).3.2$CO_2$ [λ=0.826126(2) Å].
Figure 31B:
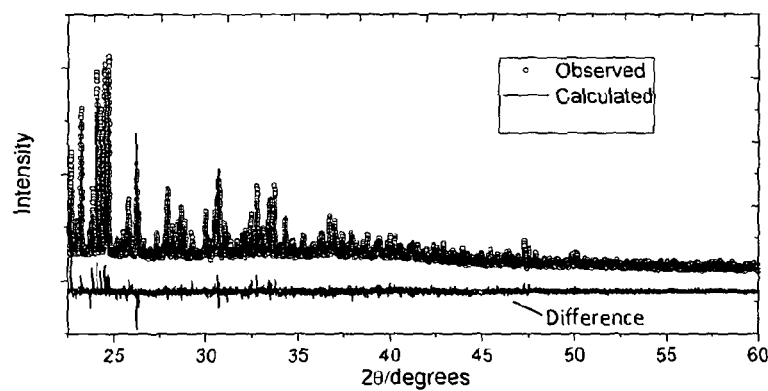
FIG. 31(b) illustrates PXRD patterns for higher angle data (2θ=22.5-60°) scaled up to show the quality of fit between the observed and the calculated patterns.
Figure 32A:
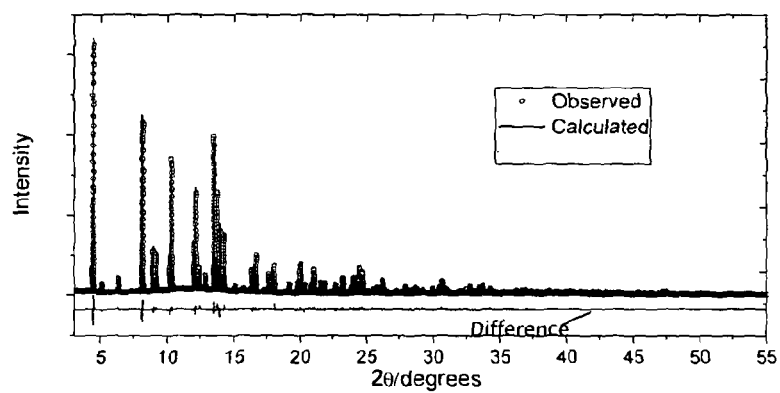
FIG. 32(a) illustrates PXRD patterns for the Rietveld refinement of the $SO_2$-loaded NOTT-300 (Al).4$SO_2$ [λ=0.826126(2) Å].
Figure 32B:
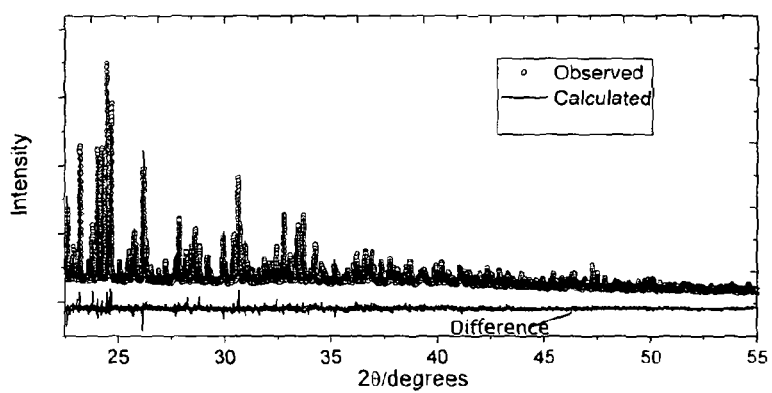
FIG. 32(b) illustrates PXRD patterns for higher angle data (2θ=22.5-55°) scaled up to show the quality of fit between the observed and the calculated patterns.
Figure 33A:
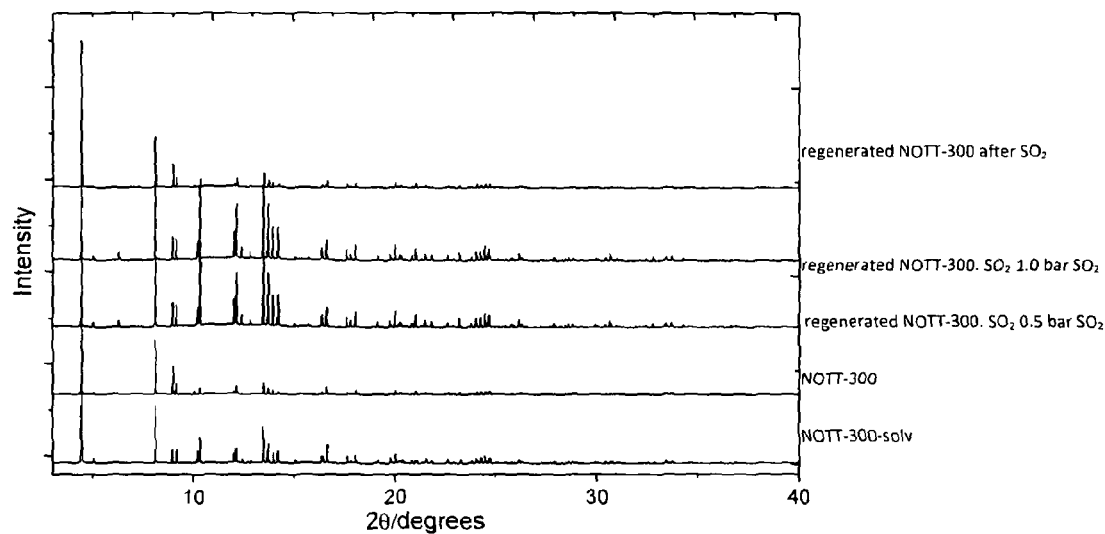
FIG. 33(a) provides a comparison of the powder diffraction patterns for original, evacuated, $SO_2$-loaded, and final desolvated samples at 273 K.
Figure 33B:
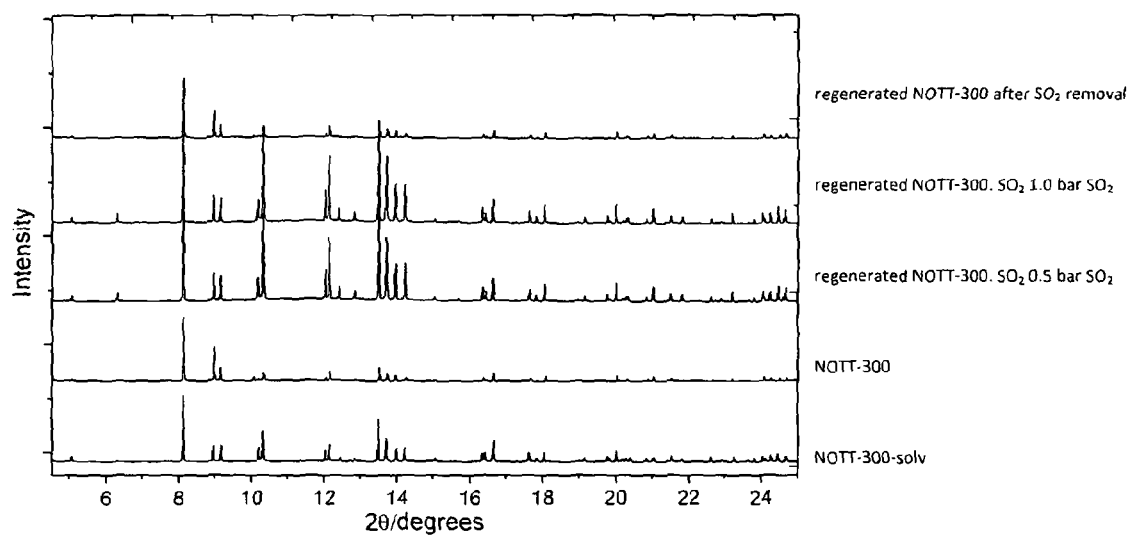
FIG. 33(b) shows the powder diffraction patterns for higher angle data (2θ=4.5-250) has been scaled up to show the changes upon $SO_2$ inclusion. NOTT-300 (Al) retains crystallinity after removal of $SO_2$.
Figure 34A:
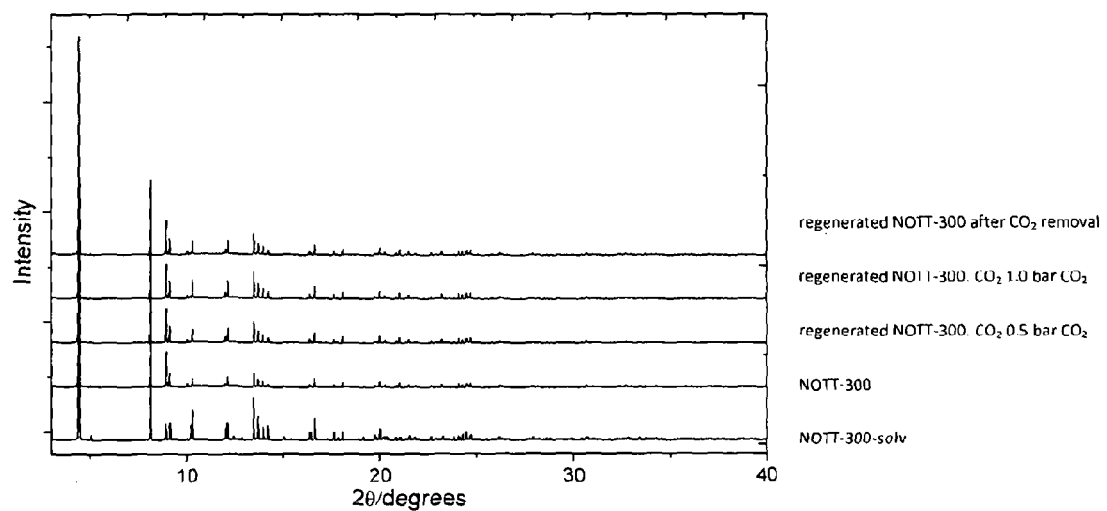
FIG. 34(a) shows powder X-ray diffraction patterns for original, evacuated, $CO_2$-loaded, and final desolvated samples at 273 K.
Figure 34B:
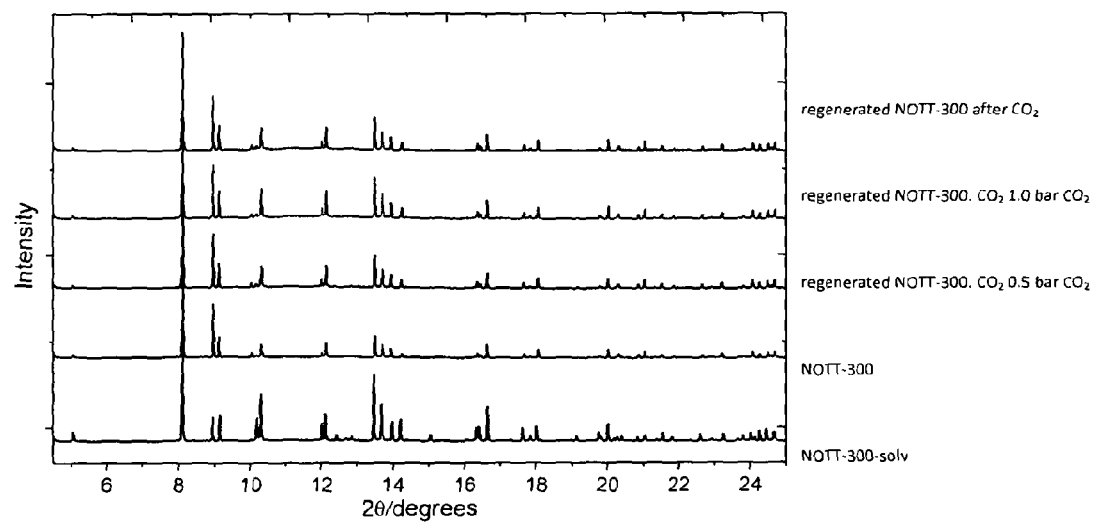
FIG. 34(b) shows powder X-ray diffraction patterns for higher angle data (2θ=4.5-25°) has been scaled up confirming that NOTT-300 (Al) retains crystallinity on removal of $CO_2$.
Figure 35:
FIG. 35 are TEM images for NOTT-300 (Al)-solvate. TEM images confirm that the crystals have uniform morphology (~1 μm plates)
Figure 35:
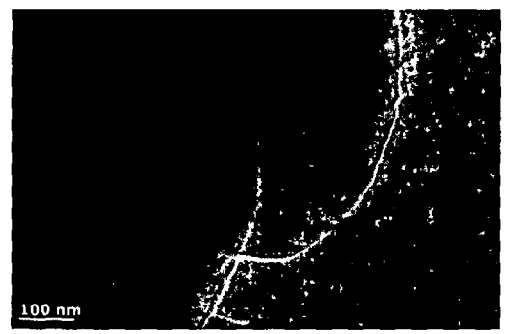
Figure 35:
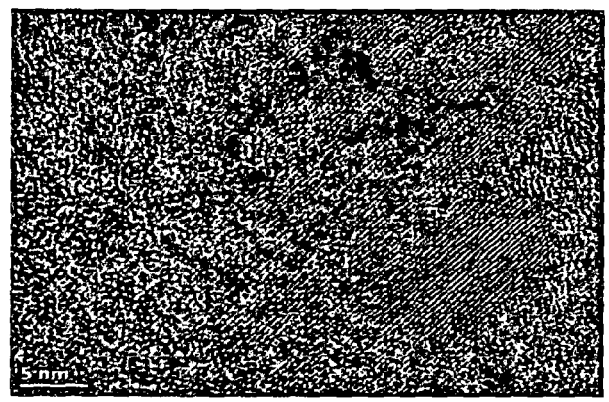
Figure 36:
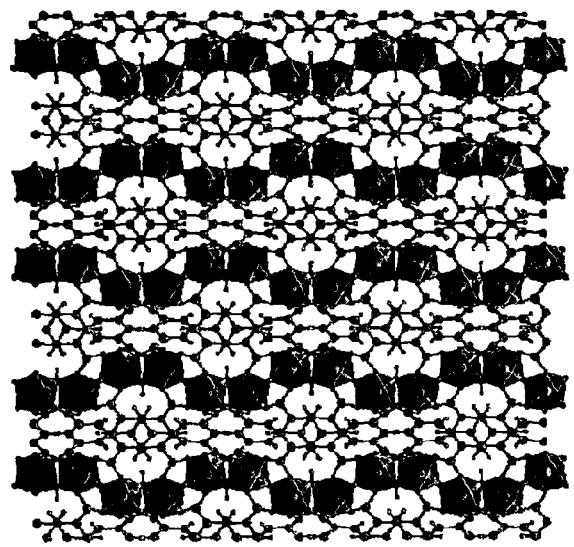
FIG. 36 provides a view of the structure of NOTT-300 (Al)-solvate along the a-axis.
Figure 37A:
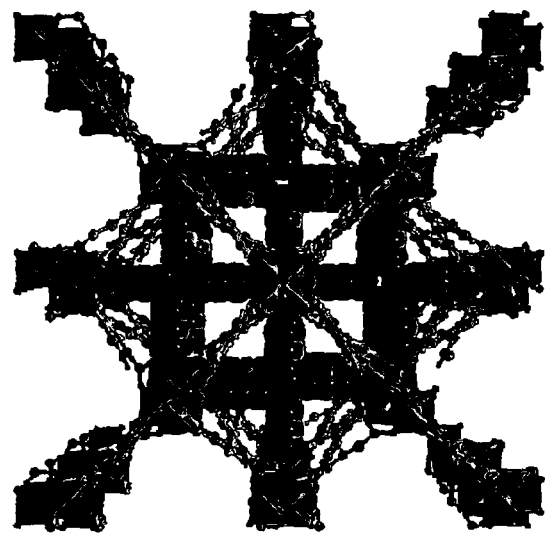
FIGS. 37(a)-37(b) provide a view of the structure of NOTT-300 (Al).1.0$CO_2$ along the c-axis (FIG. 37a) and a-axis (FIG. 37b). The structure was obtained by DFT simulation. The adsorbed $CO_2$ molecules in the pore channel are highlighted by the use of spacing filling style.
Figure 37B:
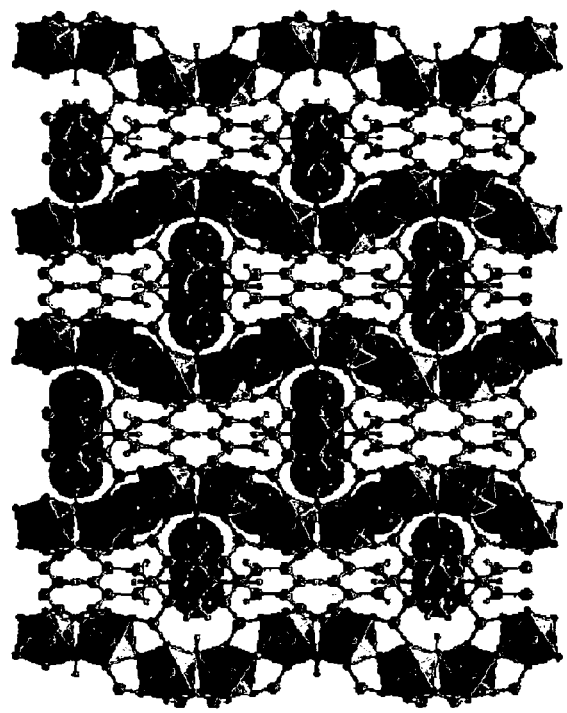
Figure 38A:
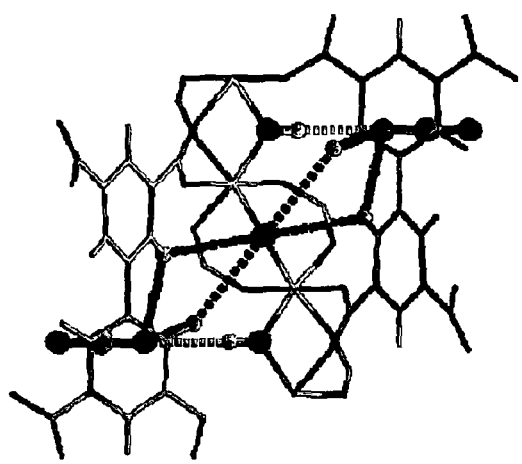
FIGS. 38(a)-38(c) provide detailed views of —OH and —CH groups binding $CO_2$ in the "pocket" cavity of NOTT-300 (Al).1.0$CO_2$. Views along (FIG. 38a) the a-axis, (FIG. 38b), the b-axis and (FIG. 38c) the c-axis. The moderate hydrogen bond between O(δ−) of $CO_2$ and H(δ+) of —OH is shown, [O . . . H=2.335 Å]. The weak cooperative hydrogen bond between O(δ−) of $CO_2$ and H(δ+) from —CH is shown, [O . . . H=3.029, 3.190 Å with each occurring twice]. Therefore, each O(δ−) centre interacts with five different H(δ+) centres.
Figure 38B:
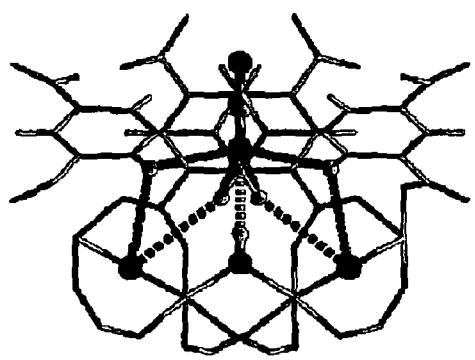
Figure 38C:
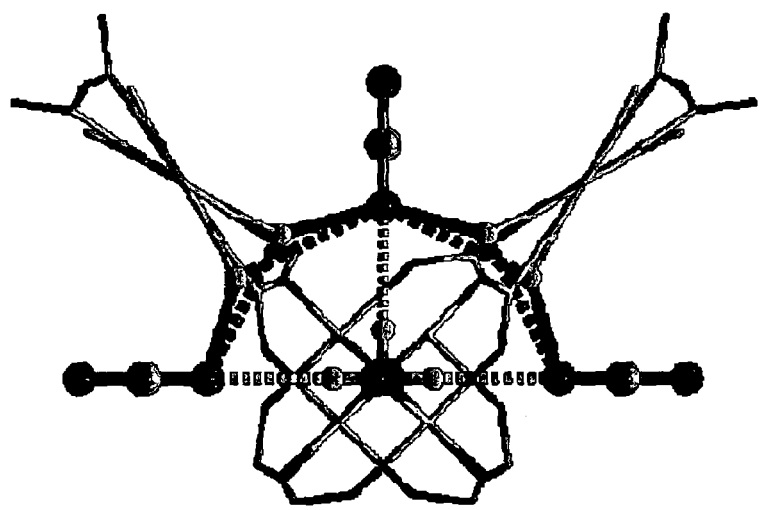
Figure 39A:
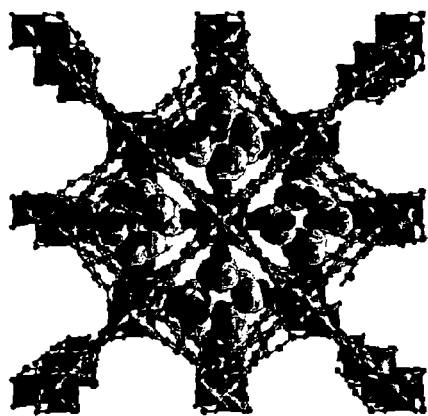
FIGS. 39(a)-39(b) provide a view of the structure of NOTT-300 (Al).4.0SO$_2$ along the c-axis (FIG. 39a) and a-axis (FIG. 39b). The structure was obtained by Rietveld refinement of high resolution powder diffraction data collected for NOTT-300 (Al).4.0SO$_2$. The adsorbed SO$_2$ molecules in the pore channel are highlighted by the use of spacing filling style FIGS. 40(a)-40(c) provide detailed views of —OH and —CH groups binding SO$_2$ in the "pocket" cavity of NOTT-300 (Al).4.0SO$_2$. Views along (FIG. 40a) the a-axis, (FIG. 40b), the b-axis and (FIG. 40c) the c-axis. The modest hydrogen bond between O($\delta$-) of SO$_2$(I) and H($\delta$+) from —OH is shown, [O . . . H=2.376(13) Å]. The weak cooperative hydrogen bond between O($\delta$-) of SO$_2$ and H($\delta$+) from —CH is shown, [O . . . H=2.806(14), 2.841(17), 3.111(16), 3.725(18) Å]. Therefore, each O($\delta$-) centre is interacting with five different H($\delta$+) centres. The bond distance between S($\delta$+) of SO$_2$(I) and O($\delta$-) of SO$_2$(II) is 3.34(7) Å is shown. The S—O bond distances are 1.481(4) and 1.500(8) Å for SO$_2$(I) and SO$_2$(II), respectively. The <O—S—O angles are 117.5(11) and 109.1(9) Å for SO$_2$(I) and SO$_2$(II), respectively.
Figure 39B:
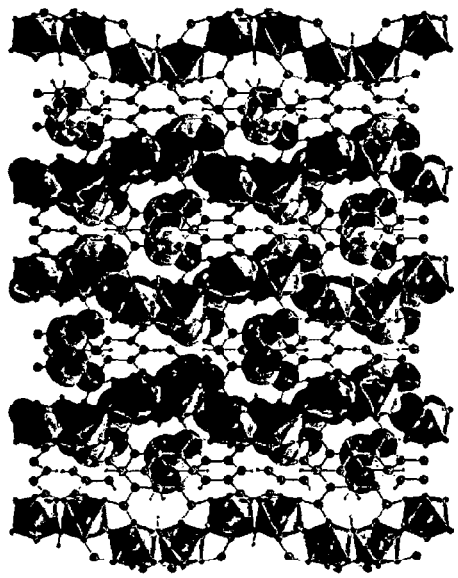
Figure 40A:
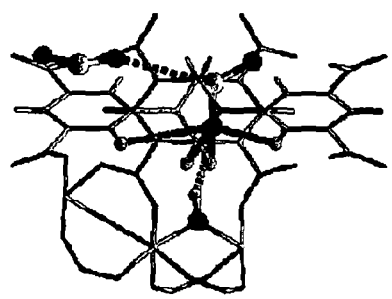
Figure 40B:
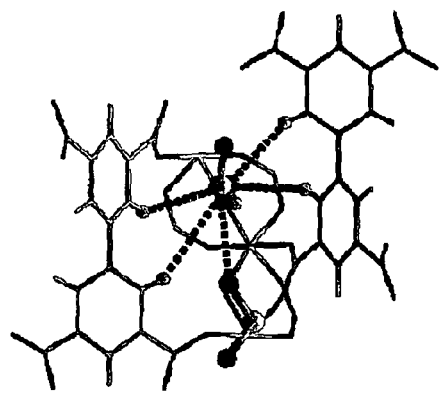
Figure 40C:
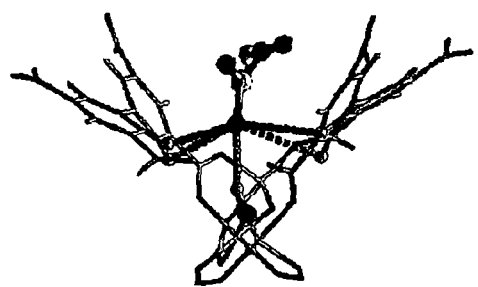

The calculation of the bare material is computationally stable, in the calculation of the vibrational frequencies, all the frequencies are positive. FIG. 29 illustrates the potential energy surface along the first vibrational eigenvector of the hydrogen bond between $CO_2$ and the —OH moieties. At the centre it is clear that the potential would give an unstable configuration from a classical point of view. The calculated solution of the Schrödinger equation gives the energy levels at 14.2 and 81 cm$^{-1}$. The zero point energy is higher than the local maximum so that from a quantum point of view, the system is in a stable equilibrium. In the calculation of the MOF material loaded with four $CO_2$ molecules per unit cell (FIG. 29), corresponding to NOTT-300 (Al).1.0CO$_2$, 8 imaginary frequency modes were found. Following the methodology previously used in MOF modelling,[5] we calculated the potential energy surface (PES) along each of the negative frequency modes (corresponding to the rocking motion of the $CO_2$ unit). FIG. 29 shows the potential energy surface (PES) for the hydrogen bond between CO2 and —OH group of the NOTT-300 (Al).1.0CO$_2$. The obtained PES confirms that the zero-point energy (ZPE) level (the ground state) lies at an energy above the local minimum calculated by DFT. This means that these PES, although corresponding to an unstable structure from a static classical point of view, are indeed stable structures from the quantum mechanical view.

The location of $SO_2$ molecules in NOTT-300 has been optimised by DFT modelling based on the measured INS spectra. The DFT calculation was performed using the same settings as in the case of $CO_2$. Notably, a high symmetry configuration, which does not take into account the disorder of $SO_2$ molecules in the channel, was used.

Analysis and Derivation of the Isosteric Heat of Adsorption for $CO_2$ in NOTT-300 (Al).

To estimate the isosteric enthalpies (AH) for $CO_2$ adsorption, all isotherms at 273-303 K were fitted to the van't Hoff equation (1):

$$\frac{d\ln(p)}{d(1/T)} = -\frac{\Delta H}{R} \quad (1)$$

where p is pressure, T is the temperature, R is the real gas constant. Selected linear fitting plots at 0.5, 1.0, 1.5 and 2.0 mmol g$^{-1}$ are shown in FIG. 53. All linear fittings show $R^2$ above 0.999, indicating consistency of the isotherm data.

FIGS. 57(a)-57(d) provide linear fitting of Van't Hoff plots for the $CO_2$ adsorption isotherms at 0.5, 1.0, 1.5 and 2.0 mmol g$^{-1}$ loadings.

Calculation of Henry's Law Selectivity for Gas Adsorption in NOTT-300.

To estimate the selectivity of $CO_2$ and $SO_2$ over other gases at zero surface coverage, all low pressure isotherm data at 273 K were fitted using a linear virial-type expression (2) employed previously to model gas sorption in MOFs. For the isotherms with overall low uptakes, where a good linear fitting cannot be obtained at low pressure, the non-linear virial type expression (3) was employed to achieve reasonable virial fitting with inclusion of data at relatively high pressure.[6]

$$\ln(n/p) = A_0 + A_1 n \quad (2)$$

$$\ln(n/p) = A_0 + A_1 n + A_2 n^2 + \quad (3)$$

where p is the pressure expressed, n is the amount adsorbed, $A_i$ are virial coefficients, and i represent the number of coefficients required to adequately describe the isotherms with low uptakes. The results of the fitting for all isotherms give $R^2$ greater than 0.99 and the Henry constants for each component were extracted from the virial coefficients (Tables S5).

The Henry's constant ($K_H$) can be extracted from the values of the virial coefficients $A_0$ using expression (4).

$$K_H = \exp(A_0) \quad (4)$$

The Henry's Law selectivity for component i($CO_2$ or $SO_2$) over other gas component j(CO, $CH_4$, $N_2$, $O_2$, Ar or $H_2$) was estimated based on the ratio of their Henry's constants (equation 5). The results are listed in Table S6. The selectivity data from virial fittings and Henry's Law analysis are confined to the zero surface coverage situations.

$$S_{ij} = K_{Hi}/K_{Hj} \quad (5)$$

Table S5 provides virial fitting results and Henry's constants $K_H$ for $CO_2$, $SO_2$, $CH_4$, $N_2$, $H_2$, $O_2$ and Ar in NOTT-300 (Al) from isotherm data at 273 K.

TABLE S5

|  | $CO_2$ | $SO_2$ | CO | $CH_4$ | $N_2$ | $H_2$ | $O_2$ | Ar |
|---|---|---|---|---|---|---|---|---|
| $A_0$/ln(mol g$^{-1}$ Pa$^{-1}$) | −14.11(8) | 6.22(40) | −20.27(3) | −20.34(3) | −20.81(1) | n.a. * | −20.04(2) | −20.57(2) |
| $K_H$/mol g$^{-1}$ Pa$^{-1}$ | 7.45(57) ×10$^{-7}$ | 508(167) | 1.57(5) ×10$^{-9}$ | 1.46(4) ×10$^{-9}$ | 9.14(10) ×10$^{-10}$ |  | 1.98(2) ×10$^{-9}$ | 1.16(2) ×10$^{-9}$ |
| Fitting $R^2$ | 0.990 | 0.996 | >0.999 | >0.999 | >0.999 |  | >0.999 | >0.999 |
| Residual error | 0.00075 | 0.034 | 0.022 | 0.022 | 0.016 |  | 0.011 | 0.030 |

* The uptake of $H_2$ isotherm at 273 K (below 0.01 wt %) is too low to obtain a reasonable virial fitting curve, and the Henry constant is therefore considered to be approximately zero.

Table S6 provides virial fitting results and Henry's constants $K_H$ for $CO_2$, $SO_2$, $CH_4$, $N_2$, $H_2$, $O_2$ and Ar in NOTT-300 (Al) from isotherm data at 283 K.

TABLE S6

|  | $CO_2$ | $SO_2$ | CO | $CH_4$ | $N_2$ | $H_2$ | $O_2$ | Ar |
|---|---|---|---|---|---|---|---|---|
| $A_0$/ln(mol g$^{-1}$ Pa$^{-1}$) | −14.57(5) | 5.75(50) | −20.38(2) | −20.29(2) | −20.84(1) | n.a.* | −20.11(2) | −20.70(3) |
| $K_H$/mol g$^{-1}$ Pa$^{-1}$ | 4.70(24) ×10$^{-7}$ | 314(123) | 1.41(3) ×10$^{-9}$ | 1.54(3) ×10$^{-9}$ | 8.88(9) ×10$^{-10}$ |  | 1.85(4) ×10$^{-9}$ | 1.03(4) ×10$^{-9}$ |
| Fitting $R^2$ | 0.994 | 0.991 | >0.999 | >0.999 | >0.999 |  | >0.999 | >0.999 |
| Residual error | 0.00050 | 0.141 | 0.021 | 0.013 | 0.024 |  | 0.023 | 0.012 |

*The uptake of $H_2$ isotherm at 283 K (below 0.01 wt %) is too low to obtain a reasonable virial fitting curve, and the Henry constant is therefore considered to be approximately zero.

Table S7. Virial fitting results and Henry's constants $K_H$ for $CO_2$, $SO_2$, $CH_4$, $N_2$, $H_2$, $O_2$ and Ar in NOTT-300 (Al) from isotherm data at 293 K.

TABLE S7

|  | $CO_2$ | $SO_2$ | CO | $CH_4$ | $N_2$ | $H_2$ | $O_2$ | Ar |
|---|---|---|---|---|---|---|---|---|
| $A_0$/ln(mol g$^{-1}$ Pa$^{-1}$) | −15.52(3) | 5.46(126) | −20.37(2) | −20.23(3) | −20.78(3) | n.a.* | −19.98(2) | −20.69(2) |
| $K_H$/mol g$^{-1}$ Pa$^{-1}$ | 1.82(6) ×10$^{-7}$ | 235(168) | 1.42(2) ×10$^{-9}$ | 1.63(4) ×10$^{-9}$ | 9.42(22) ×10$^{-10}$ |  | 2.10(5) ×10$^{-9}$ | 1.03(2) ×10$^{-9}$ |
| Fitting $R^2$ | 0.997 | 0.977 | >0.999 | >0.999 | >0.999 |  | >0.999 | >0.999 |
| Residual error | 0.000030 | 0.024 | 0.020 | 0.013 | 0.011 |  | 0.017 | 0.015 |

*The uptake of $H_2$ isotherm at 283 K (below 0.01 wt %) is too low to obtain a reasonable virial fitting curve, and the Henry constant is therefore considered to be approximately zero.

Table S8 provides virial fitting results and Henry's constants $K_H$ for $CO_2$, $SO_2$, $CH_4$, $N_2$, $H_2$, $O_2$ and Ar in NOTT-300 (Al) from isotherm data at 303 K.

TABLE S8

|  | $CO_2$ | $SO_2$ | CO | $CH_4$ | $N_2$ | $H_2$ | $O_2$ | Ar |
|---|---|---|---|---|---|---|---|---|
| $A_0$/ln(mol g$^{-1}$ Pa$^{-1}$) | −16.44(1) | 4.30(100) | −20.27(2) | −20.15(2) | −20.73(1) | n.a.* | −20.03(1) | −20.42(2) |
| $K_H$/mol g$^{-1}$ Pa$^{-1}$ | 7.25(8) ×10$^{-8}$ | 73.7(465) | 1.57(2) ×10$^{-9}$ | 1.77(4) ×10$^{-9}$ | 9.89(10) ×10$^{-10}$ |  | 2.04(1) ×10$^{-9}$ | 1.35(2) ×10$^{-9}$ |
| Fitting $R^2$ | 0.994 | 0.976 | >0.999 | >0.999 | >0.999 |  | >0.999 | >0.999 |
| Residual error | 0.000072 | 0.050 | 0.016 | 0.016 | 0.0048 |  | 0.022 | 0.013 |

*The uptake of $H_2$ isotherm at 283 K (below 0.01 wt %) is too low to obtain a reasonable virial fitting curve, and the Henry constant is therefore considered to be approximately zero.

Table S9 provides a summary of gas adsorption selectivity data obtained by two methods: (i)$^a$ the ratio of slopes of initial adsorption isotherm plot; (ii)$^b$ Henry's Law analysis at 273 K.

TABLE S9

| Selectivity ratio | Isotherm plot slop | Henry's Law analysis |
|---|---|---|
| $CO_2$/CO | 86 | 475 |
| $CO_2$/$CH_4$ | 100 | 510 |
| $CO_2$/$N_2$ | 180 | 815 |
| $CO_2$/$H_2$ | >10$^5$ | >10$^5$ |
| $CO_2$/$O_2$ | 70 | 376 |
| $CO_2$/Ar | 137 | 642 |
| $SO_2$/CO | 3105 | >10$^5$ |
| $SO_2$/$CH_4$ | 3620 | >10$^5$ |
| $SO_2$/$N_2$ | 6522 | >10$^5$ |
| $SO_2$/$H_2$ | >10$^5$ | >10$^5$ |
| $SO_2$/$O_2$ | 2518 | >10$^5$ |
| $SO_2$/Ar | 4974 | >10$^5$ |

$^a$This method represents the selectivity at low pressure region (50-350 mbar) and is close to the situation from the direct comparison of gas uptakes.
$^b$This method represents the extreme selectivity at zero surface coverage of a given material, and therefore is higher than the values from method (i). Selectivity data obtained from method (i) are reported in the main text.

Table S10. Summary of gas adsorption selectivity data obtained by two methods: (i)$^a$ the ratio of slopes of initial adsorption isotherm plot; (ii)$^b$ Henry's Law analysis at 283 K.

TABLE S10

| Selectivity ratio | Isotherm plot slop | Henry's Law analysis |
|---|---|---|
| $CO_2$/CO | 67 | 333 |
| $CO_2$/$CH_4$ | 57 | 305 |
| $CO_2$/$N_2$ | 110 | 529 |

TABLE S10-continued

| Selectivity ratio | Isotherm plot slop | Henry's Law analysis |
|---|---|---|
| $CO_2/H_2$ | >$10^5$ | >$10^5$ |
| $CO_2/O_2$ | 54 | 254 |
| $CO_2/Ar$ | 90 | 456 |
| $SO_2/CO$ | 3586 | >$10^5$ |
| $SO_2/CH_4$ | 3061 | >$10^5$ |
| $SO_2/N_2$ | 5864 | >$10^5$ |
| $SO_2/H_2$ | >$10^5$ | >$10^5$ |
| $SO_2/O_2$ | 2880 | >$10^5$ |
| $SO_2/Ar$ | 4831 | >$10^5$ |

[a]This method represents the selectivity at low pressure region (50-350 mbar) and is close to the situation from the direct comparison of gas uptakes.
[b]This method represents the extreme selectivity at zero surface coverage of a given material, and therefore is higher than the values from method (i).

Table S11. Summary of gas adsorption selectivity data obtained by two methods: (i)[a] the ratio of slopes of initial adsorption isotherm plot; (ii)[b] Henry's Law analysis at 293 K.

TABLE S11

| Selectivity ratio | Isotherm plot slop | Henry's Law analysis |
|---|---|---|
| $CO_2/CO$ | 45 | 128 |
| $CO_2/CH_4$ | 39 | 112 |
| $CO_2/N_2$ | 72 | 193 |
| $CO_2/H_2$ | >$10^5$ | >$10^5$ |
| $CO_2/O_2$ | 39 | 87 |
| $CO_2/Ar$ | 64 | 177 |
| $SO_2/CO$ | 2854 | >$10^5$ |
| $SO_2/CH_4$ | 2464 | >$10^5$ |
| $SO_2/N_2$ | 4545 | >$10^5$ |
| $SO_2/H_2$ | >$10^5$ | >$10^5$ |
| $SO_2/O_2$ | 2490 | >$10^5$ |
| $SO_2/Ar$ | 4070 | >$10^5$ |

[a]This method represents the selectivity at low pressure region (50-350 mbar) and is close to the situation from the direct comparison of gas uptakes.
[b]This method represents the extreme selectivity at zero surface coverage of a given material, and therefore is higher than the values from method (i).

Table S12 provides a summary of gas adsorption selectivity data obtained by two methods: (i)[a] the ratio of slopes of initial adsorption isotherm plot; (ii)[b] Henry's Law analysis at 303 K.

TABLE S12

| Selectivity ratio | Isotherm plot slop | Henry's Law analysis |
|---|---|---|
| $CO_2/CO$ | 32 | 46 |
| $CO_2/CH_4$ | 31 | 41 |
| $CO_2/N_2$ | 46 | 73 |
| $CO_2/H_2$ | >$10^5$ | >$10^5$ |
| $CO_2/O_2$ | 30 | 36 |
| $CO_2/Ar$ | 41 | 54 |
| $SO_2/CO$ | 1586 | >$10^5$ |
| $SO_2/CH_4$ | 1510 | >$10^5$ |
| $SO_2/N_2$ | 2252 | >$10^5$ |
| $SO_2/H_2$ | >$10^5$ | >$10^5$ |
| $SO_2/O_2$ | 1458 | >$10^5$ |
| $SO_2/Ar$ | 2002 | >$10^5$ |

[a]This method represents the selectivity at low pressure region (50-350 mbar) and is close to the situation from the direct comparison of gas uptakes. [b]This method represents the extreme selectivity at zero surface coverage of a given material, and therefore is higher than the values from method (i).

Summary of the Hydrogen Bond Interactions in NOTT-300 (Al).

A hydrogen bond system is conventionally represented as a linear A-H . . . B arrangement of a hydrogen donor (A-H) and an acceptor (B). Relevant properties of the different strengths of hydrogen bonds are given in Table C1. In this system, the hydrogen bond length H . . . O is around 2.3 Å (FIG. 4d), and therefore it can be classed as a moderate-to-weak hydrogen bond. The four C—H supramolecular contacts are likely to be of lower energies. Based on this analysis, we view the observed value of $Q_{st}$ as entirely reasonable and consistent with the likely hydrogen bond energies. In addition, there is the possibility of electrostatic Al(III)/$XO_2$ interactions. The high $CO_2$ uptakes also reflect the relatively narrow pore size of the host which provides strong overlap potentials.

Table S13 provides properties of strong, moderate and weak H-bonds.

| Properties | Strong H-bonds | Moderate H-bonds | Weak H-bonds |
|---|---|---|---|
| Bond energy (kJ $mol^{-1}$) | 4-10 | 1-3 | <1 |
| Bond nature | mostly covalent | mostly electrostatic | electrostatic |
| Bond linearity, A-H . . . B | always linear | mostly linear | sometimes linear |
| Bond length A-H (Å) | 1.2 to 1.5 | ca 1.0 | ca 1.0 |
| Bond length H . . . B (Å) | 1.2 to 1.5 | 1.5 to 2.2 | 2.2 to 3.2 |
| Bond length A . . . B (Å) | 2.2 to 2.5 | 2.5 to 3.2 | 3.2 to 4.0 |

Example 2

Synthesis of NOTT-300 (In)

Biphenyl-3,3',5,5'-tetracarboxylic acid (0.015 g, 0.045 mmol), $In(NO_3).(H_2O)_5$ (0.014 mg, 0.045 mmol) and piperazine (7.0 mg, 0.081 mmol) were mixed and dispersed in DMF/MeCN mixture (1.3 mL, 1:0.3 v/v). The white slurry was acidified with dilute nitric acid (5%, 0.3 mL) and heated to 100° C. Upon reaching 60° C. the white slurry was observed to fully dissolve resulting in a colourless solution followed by precipitation of a white crystalline powder which was washed sequentially with DMF and dried briefly in air. Powder diffraction data (PXRD) confirm that the parent MOF NOTT-300 (In)-solv is iso-structural to NOTT-300(Al)-solv. Yield: 20 mg (75%). Elemental analysis (% calc/found): $[In_2(C_{16}H_6O_8)_2 (DMF)_{0.75}(H_2O)_{1.75}$ (C, 33.02/33.02; H, 2.20/2.53; N, 1.58/1.58). Selected IR(ATR): $v/cm^1$=1705 (s), 1669 (s), 1652 (s), 1612 (m), 1549 (s), 1423 (s), 1367 (s), 1311 (w), 1253 (w), 1226 (w), 974 (m), 799 (s), 709 (s).

Example 3

Synthesis of NOTT-300(Sb)

Biphenyl-3,3',5,5'-tetracarboxylic acid (0.015 g, 0.045 mmol) and $SbCl_3$ (0.010 mg, 0.045 mmol) were mixed and dispersed in DMF/MeCN mixture (1.3 mL, 1:0.3 v/v). The white slurry was acidified with dilute nitric acid (5%, 0.3 mL) and heated to 100° C. Upon reaching 60° C. the white slurry was observed to fully dissolve resulting in a colourless solution followed by precipitation of a white crystalline powder which was washed sequentially with DMF and dried briefly in air. $[Sb_2(C_{16}H_6O_8)\text{-}_2.(DMF)_x.(H_2O)_y$. Colourless block (0.03×0.02×0.01 mm) $I4_122$, a=15.4500(5) c=12.2908(6) Å, V=2933.9(2) Å$^3$, Z=4, $D_{calc}$=1.362 g $cm^{-3}$, μ=14.927 $mm^{-1}$, F(000)=1136. A total of 1473 reflections was collected, of which 1392 were unique, with $R_{int}$=0.0606. Final $R_1$ (w$R_2$)=0.0643 (0.2060) with GOF=1.880. The final difference Fourier extrema were 3.32 and −0.88 e/Å$^3$.

Example 4

Synthesis of NOTT 300 (Cr)

Chromium nitrate, $Cr(NO_3)_3 \cdot 9H_2O$, (0.36 g, 0.9 mmol) was dissolved in water (10 mL), biphenyl-3,3',5,5'-tetracarboxylic acid (0.06 g, 0.18 mmol) was then added. Piperazine (0.1 g) was added followed by addition of 2.8 M nitric acid (2 mL). The reaction mixture was transferred to a 2 mL autoclave which was sealed and heated to 210° C. for 72-96 h. The resulting powder product was separated by filtration and washed with water.

Example 5

Synthesis of NOTT-300(Ga)

NOTT-300($Ga_2$) $\{[Ga_2(OH)_2(C_{16}H_6O_8)]\}$ was synthesised under solvothermal conditions by reacting biphenyl-3,3',5,5'-tetracarboxylic acid (0.02 g, 0.06 mmol) and gallium nitrate, $Ga(NO_3)_3 \cdot xH_2O$, (0.1 g, 0.36 mmol), in a mixture of DMF, THF and water (8 mL, 2:5:1, v/v) which was then acidified with 5-15 drops of hydrochloric acid and heated at 75° C. for 72 h.

Crystal Structure of NOTT-300(Ga)

NOTT-301($Ga_2$)-solv crystallises in a chiral space group $I4_122$ and shows a 3D open framework structure constructed from 1D helical $[Ga(OH)_2O_4]_\infty$ chains bridged by tetracarboxylate ligand. The Ga(III) ion is octahedrally coordinated via six O-donors: four from carboxylate groups and two from bridging hydroxyl groups $\mu_2$-OH which are aligned in cis confirmation.

TABLE 1

Summary of unit cell parameters for ($Ga_2$)-solvated, ($Ga_2$)-desolvated and ($Ga_2$)-CO2 loaded (In situ single crystal)

| Single Crystal | Parameter cell (a = b), Å | Parameter cell (c), Å | Cell volume, Å$^3$ | M |
|---|---|---|---|---|
| ($Ga_2$)-solv | 15.1675(9) | 11.9197(15) | 2742.2(4) | 688.68 |
| ($Ga_2$) | 15.0174(7) | 11.9111(11) | 2686.2(3) | 499.66 |
| $CO_2$-loaded | 15.0535(6) | 11.8737(10) | 2690.7(3) | 596.49 |

TABLE 2

Summary of unit cell parameters for ($Ga_{2-x}Fe_x$)MOF (x = 0, 0.13, 0.21, 0.45)

| | Parameter cell (a = b), Å | Parameter cell (c), Å | Cell volume, Å$^3$ | $R_{Bragg}$ | Rp | Rwp | GOF |
|---|---|---|---|---|---|---|---|
| $Ga_2$ | 15.0071(1) | 11.8814(9) | 2675.9(4) | 0.045 | 0.068 | 0.01 | 4.512 |
| $Ga_{1.87}Fe_{0.13}$ | 15.0439(7) | 11.8767(6) | 2687.9(3) | 0.036 | 0.068 | 0.090 | 2.673 |
| $Ga_{1.79}Fe_{0.21}$ | 14.9980(1) | 11.8938(1) | 2675.4(5) | 0.02 | 0.059 | 0.076 | 1.293 |
| $Ga_{1.55}Fe_{0.45}$ | 15.0684(8) | 11.9111(8) | 2704.5(4) | 0.06 | 0.050 | 0.066 | 1.877 |

Example 6

Synthesis of NOTT-300(GaFe)

A mixed Ga—Fe material was obtained using a similar procedure but incorporating stoichiometric mixtures of gallium nitrate $Ga(NO_3)_3 \cdot xH_2O$ and iron nitrate $Fe(NO_3)_3 \cdot 9H_2O$ in the following ratios: $[Ga_{1.87}Fe_{0.13}(OH)_2(C_{16}H_6O_8)]$: (0.09 g, 0.34 mmol), (0.007 g, 0.18 mmol); $[Ga_{1.79}Fe_{0.21}(OH)_2(C_{16}H_6O_8)]$: (0.083 g, 0.32 mmol), (0.015 g, 0.036 mmol); $[Ga_{1.55}Fe_{0.45}(OH)_2(C_{16}H_6O_8)]$: (0.078 g, 0.31 mmol), (0.022 g, 0.054 mmol), respectively.

Conclusions

Figure 3B:
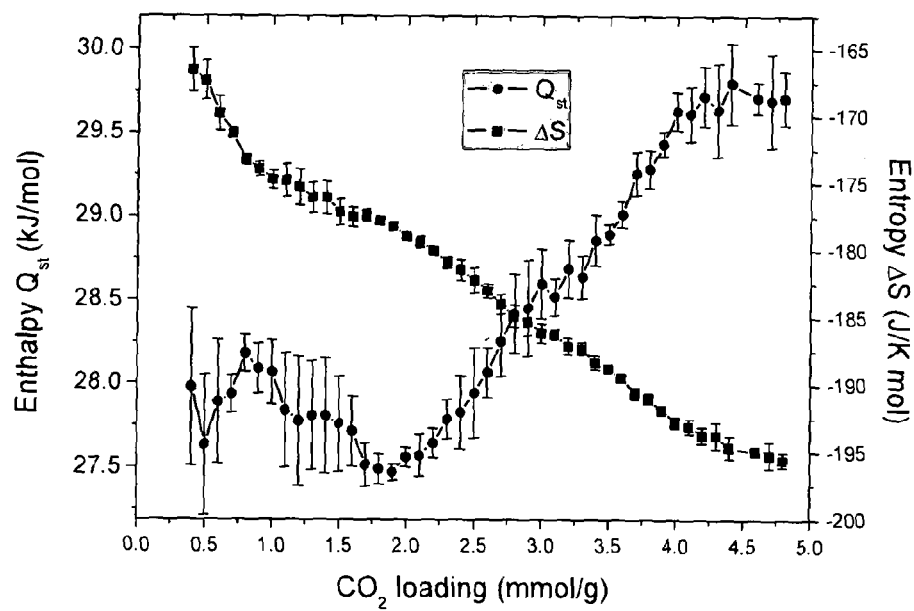

In situ INS and PXRD studies on the non-amine-containing capture material NOTT-300 have led to the same conclusions, for all of the metal (III) complexes, namely that the M-OH groups (M=Al, Cr, Sb, In, Ga, Fe) in the pore cavity can participate in moderate interactions with $XO_2$ (X=C, S, N) and $C_2H_x$ (x=2,4,6), and that these can be supplemented by cooperative interactions with adjacent C—H groups of benzene rings. The binding energy of these moderate-to-weak hydrogen bonds (Table S13) can be viewed as soft binding interactions, quite distinct from the direct bond formation between the N-centre of amine groups and the electro-positive C-carbon centre of $CO_2$. The latter, seen in amine systems, lead to very high isosteric heats of adsorption (40-90 kJ mol$^1$ for physisorption; 85-105 kJ mol$^{-1}$ for chemisorption) and result in a substantial energy penalty to release adsorbed $CO_2$. The moderate isosteric heat of adsorption in NOTT-300 [eg 27-30 kJ mol$^{-1}$ for NOTT-300-(Al) (FIG. 3b)] confirms that the relatively weak hydrogen bonding interactions within this OH— decorated system are sufficiently strong to selectively bind $CO_2$ and $SO_2$. The weak interaction is also evidenced by the fully reversible desorption isotherms observed for these gases. This offers great promise not only for the efficient capture of $CO_2$ $SO_2$, and $NO_2$ but also for their facile, low-energy and therefore economic release subsequently; moreover this "easy-on"/"easy-off" soft binding model is achieved without any reduction in either selectivity or capacity.

Gas Capture Apparatus

Figure 27:
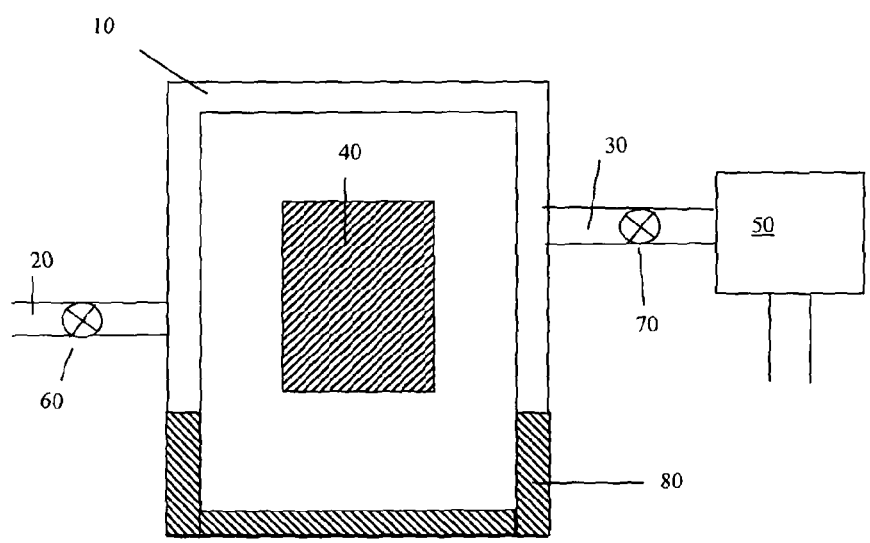
FIG. 27 is a schematic illustration of an apparatus for gas storage.

FIG. 27 illustrates a gas capture apparatus comprising a container 10 in which the MOF 40 is contained. The container 10 may have one or more inlets 20 in which gases may enter the container 10. The gases may be flue gases produced be a power station or from some other combustion or industrial processes for example in the production of iron, steel, ammonia and cement. In such applications the MOF 40 may be regenerated. In this case the MOF 40 in container 10 may be heated using a heater 80 so as drive-off adsorbed gases and regenerate the MOF 40 for its re-use. Alternatively desorption of gasses from the MOF 40 may proceed through the application of vacuum to the vessel containing the MOF.

In such applications the container 10 may be in fluid connection with a vacuum pump 50 configured to draw off the gases (eg. $XO_2$ (X=C, S, N) or hydrocarbons such as $C_2H_2$, $C_2H_4$, $C_2H_6$), that have been trapped and subsequently released by the MOF, for subsequent storage, handling and/or transportation, for example the gases may be compressed or liquefied before subsequent handling or transportation. An inlet valve 60 may be closed and an outlet valve 70 may be opened whilst the MOF 40 is being heated so that the captured are not released back into the flue. Or a vacuum may be applied through valve 70 to desorb the gas from MOF 40 where heating is not used. Whilst the apparatus is being used to capture gases the inlet valve 60 will be open and the outlet valve 60 may be closed.

Figure 28A:
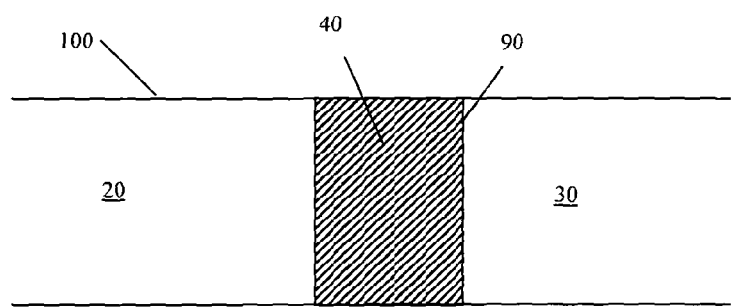
FIG. 28(a) illustrates a cartridge placed within a gas stream.
Figure 28B:
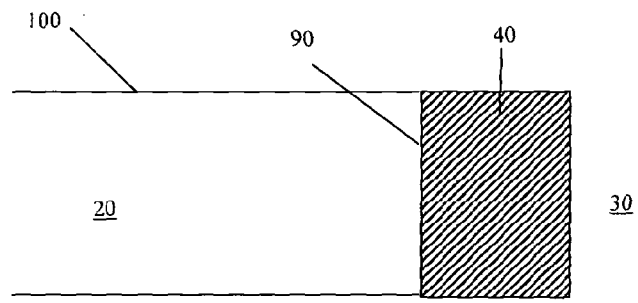
FIG. 28(b) illustrates a cartridge at the end of a flue or exhaust pipe.

The MOF may also be used as part of a cartridge system in which a cartridge 90 (or other container/mechanism to support or hold the MOF) is placed in the gas stream to be processed. The cartridge 90 may then be removed from the gas stream so as to be regenerated off-line from the gas stream. FIG. 28(*a*) illustrates such a cartridge 90 placed within a gas stream. The cartridge 90 may cover the majority of the cross section of a conduit 100 carrying the gas stream or may be adapted to cover substantially all of the conduit cross section as illustrated in FIG. 28(*a*). When the cartridge 90 is in the conduit 100, the conduit 100 may form both the inlet 20 and the outlet 30 (as illustrated in FIG. 28(*a*)). Such a cartridge system may be useful for anaesthetic systems and exhausts systems from combustion. FIG. 28(*b*) illustrates a cartridge at the end of a flue or exhaust pipe. In this case the side or sides of the cartridge distal from the flue may act as the outlet 30.

Experimental Information—Physical Characterisation

All reagents were used as received from commercial suppliers without further purification. Analyses for C, H and N were carried out on a CE-440 elemental analyzer (EAI Company). Thermal gravimetric analyses (TGA) were performed under $N_2$ flow (100 ml/min) with a heating rate of 2° C./min using a TA SDT-600 thermogravimetric analyzer (TA Company). IR spectra were recorded using a Nicolet Avatar 360 FT-IR spectrophotometer. High-resolution transmission electron microscopy (TEM) imaging was performed using a Jeol 2100F transmission electron microscope using an accelerating voltage of 100 kV. TEM samples were prepared by casting several drops of a suspension of the NOTT-300 solvate complex in water onto copper-grid mounted lacy carbon film before drying under a stream of nitrogen. Variable temperature powder X-ray diffraction data (PXRD) were collected over the 2θ range 4-50° on a Bruker Advance D8 diffractometer using Cu-K$\alpha_1$ radiation ($\lambda$=1.54056 Å, 40 kV/40 mA), and the temperature was controlled by an Oxford Cryosystems open-flow cryostat operating at 100-483 K.

$CO_2$, $SO_2$, $CH_4$, CO, $N_2$, $O_2$, $H_2$ and Ar sorption isotherms were recorded at 77 K (liquid nitrogen), 87 K (liquid argon) or 273-303 K (temperature-programmed water bath from Hiden Company) on an IGA-003 system at the University of Nottingham under ultra-high vacuum from a diaphragm and turbo pumping system. All gases used were ultra-pure research grade (99.999%) purchased from BOC or AIRLIQUIDE. The density of the desolvated NOTT-300 sample used in buoyancy corrections was 1.80 g cm$^{-3}$ and was estimated from the crystallographic density of the desolvated sample derived from the PLATON/SOLV[1] results. In a typical gas adsorption experiment, ~100 mg of NOTT-300 (Al)-solvate was loaded into the IGA, and degassed at 120° C. and high vacuum (10-10 bar) for 1 day to give fully desolvated NOTT-300 (Al).

INS spectra were recorded on the TOSCA spectrometer at the ISIS Facility at the Rutherford Appleton Laboratory (UK) for energy transfers between ~-2 and 500 meV. In this region TOSCA has a resolution of ~1% ΔE/E. The desolvated NOTT-300 (Al) sample was loaded into a cylindrical vanadium sample container with an annealed copper vacuum seal and connected to a gas handling system. The sample was degassed at $10^{-7}$ mbar and 140° C. for 1 day to remove any remaining trace guest water molecules. The temperature during data collection was controlled using a helium cryostat (7±0.2 K). The loading of $CO_2$ was performed at room temperature in order to ensure that $CO_2$ was present in the gas phase when not adsorbed and also to ensure sufficient mobility of $CO_2$ inside the crystalline structure of NOTT-300 (Al). The loading of $H_2$ was performed at 40-50 K in order ensure that $H_2$ was adsorbed into NOTT-300 (Al). Subsequently, the temperature was reduced to below 10 K in order to perform the scattering measurements with the minimum achievable thermal motion for $CO_2$ or $H_2$. Background spectra (sample can plus NOTT-300 (Al)) were subtracted to obtain the difference spectra. INS was used to study the binding interaction and structure dynamics in this case, because it has several unique advantages:

- INS spectroscopy is ultra-sensitive to the vibrations of hydrogen atoms, and hydrogen is ten times more visible than other elements due to its high neutron cross-section.
- The technique is not subject to any optical selection rules. All vibrations are active and, in principle, measurable.
- INS observations are not restricted to the centre of the Brillouin zone (gamma point) as is the case for optical techniques.
- INS spectra can be readily and accurately modelled: the intensities are proportional to the concentration of elements in the sample and their cross-sections, and the measured INS intensities relate straightforwardly to the associated displacements of the scattering atom. Treatment of background correction is also straightforward.
- Neutrons penetrate deeply into materials and pass readily through the walls of metal containers making neutrons ideal to measure bulk properties of this material.
- INS spectrometers cover the whole range of the molecular vibrational spectrum, 0-500 meV (0-4000 cm$^{-1}$)
- INS data can be collected at below 10 K, where the thermal motion of the MOF material and adsorbed $CO_2$ molecules can be significantly reduced.

The invention claimed is:

1. A metal organic framework comprising metal ions (M) and an organic ligand wherein more than one hydroxy ligand are present, wherein the metal ions are octahedrally coordinated as $MO_4(OH)_2$ units, wherein four of the oxygen atoms are from the organic ligands and a coordination sphere is completed by hydroxy ligands, wherein bridging —OH groups are linked to each other in a cis-configuration.

2. The metal organic framework of claim 1 wherein hydroxy ligands point into the channels of the framework.

3. The metal organic framework of claim 1, wherein the metal ion is a metal (III) ion.

4. The metal organic framework of claim 1, wherein the metal ion is selected from the group consisting of Al(III), Cr(III), Sb(III), In(III), Ga(III), and Fe(III).

5. The metal organic framework of claim 1 wherein the metal organic framework is synthesised using a metal (III) ion.

6. The metal organic framework of claim 5 wherein the metal organic framework is synthesised using one metal (III) ion selected from the group consisting of Al(III), In(III), Sb(III), Ga(III), Cr(III), Fe(III) and Co(III).

7. The metal organic framework of claim 1 comprising two or more different types of metal(III) ions.

8. The metal organic framework of claim 1, wherein the metal organic framework comprises a polycarboxylate ligand.

9. The metal organic framework of claim 8, wherein the polycarboxylate ligand is a tetracarboxylate ligand.

10. The metal organic framework of claim 9 wherein the tetracarboxylate ligand is a phenyltetracarboxylate ligand.

11. The metal organic framework of claim 10 wherein the phenyltetracarboxylate ligand has the formula:

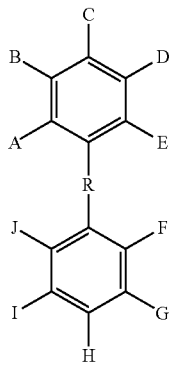

wherein R is one of

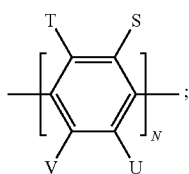

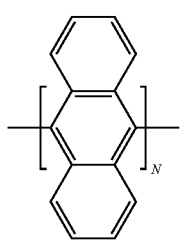

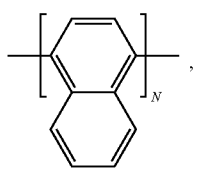

wherein A, B, C, D, E, F, G, H, I, and J are selected from the group consisting of H, F, Cl, Br, I, $CH_3$, $CH_2CH_3$, $CH(CH_3)_2$, $C(CH_3)_3$, $NH_2$, $NHR'$, $NR'R''$, OH, $OR'$, CO2H, $CO_2R'$, $CF_3$, $NHCOR'$, $NHCONHR'$, $NHSO_2R'$, $SO_3H$; and
wherein S, T, U and V are selected from the group consisting of H, F, Cl, Br, I, $CH_3$, $CH_2CH_3$, $CH(CH_3)_2$, $C(CH_3)_3$, $NH_2$, $NHR'$, $NR'R''$, OH, $OR'$, $CO_2H$, $CO_2R'$, $CF_3$, $NHCOR'$, $NHCONHR'$, $NHSO_2R'$, $SO_3H$ and

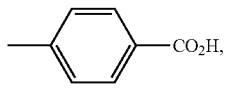

wherein R' and R'' are each independently a $C_1$ to $C_5$ alkyl.

12. The metal organic framework of claim 11 wherein, two of A,B,C,D, or E are —COOH and two of F,G,H,I or J are —COOH.

13. The metal organic framework of claim 11 wherein one of A,B,C,D, or E is —COOH and one of F,G,H,I or J is —COOH, and two of T, S, U and V are —COOH or

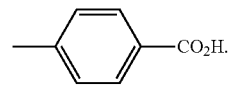

14. The metal organic framework of claim 1 wherein the organic ligand is selected from the group consisting of:

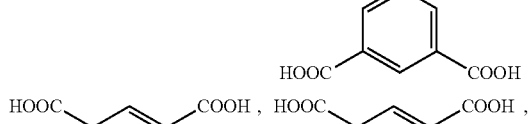

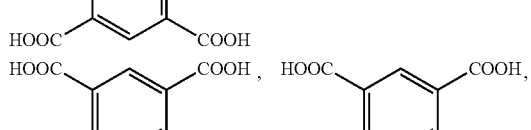

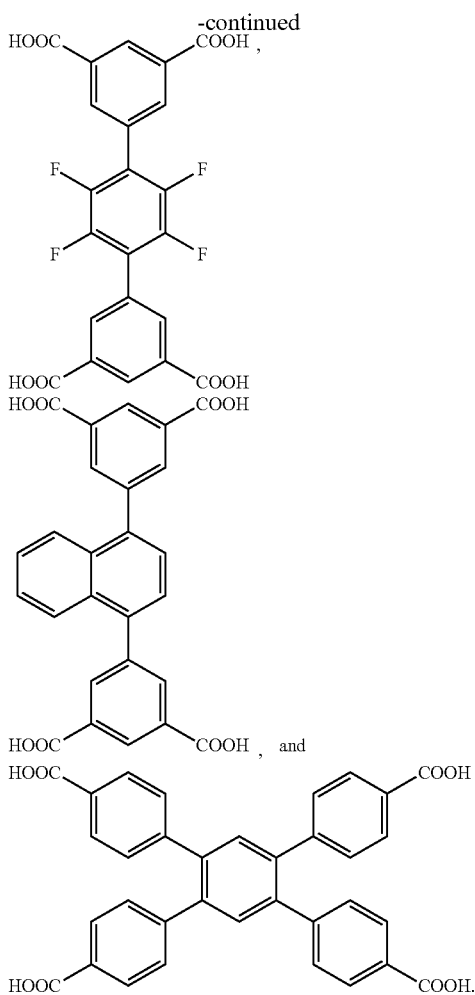

15. The metal organic framework of claim 1, wherein the metal organic framework has the formula:

$$M_2(OH)_2(C_{16}O_8H_6);$$

where M=Al, In, Sb, Ga, or Cr.

16. The metal organic framework of claim 15, wherein the metal organic framework comprises a biphenyl-3, 3',5',5' tetracarboxylate ligand.

17. The metal organic framework of claim 1, wherein the metal organic framework contains two or more different types of metal (III) ion and wherein said two or more different types of metal (III) ion are selected from the group consisting of Al(III), Cr(III), Sb(III), In(III), Ga(III), and Fe(III).

18. The metal organic framework of claim 17, wherein the metal organic framework comprises both gallium and iron and has the formula $(Ga_{2-x} Fe_x)(OH)_2(C_{16}O_8H_6)$ wherein x is greater than zero.

19. A metal organic framework comprising a metal ion (M) and an organic ligand wherein more than one hydroxy ligand are present, wherein the metal organic framework comprises a polycarboxylate ligand which is a tetracarboxylate ligand.

20. A metal organic framework comprising a metal ion (M) and an organic ligand wherein more than one hydroxy ligand are present, wherein the metal organic framework has the formula: $M_2(OH)_2(C_{16}O_8H_6)$; where M=Al, In, Sb, Ga, or Cr.

* * * * *